(12) United States Patent
Yangyuenthanasan et al.

(10) Patent No.: US 11,471,314 B2
(45) Date of Patent: Oct. 18, 2022

(54) TRUNK SUPPORTING EXOSKELETON AND METHOD OF USE

(71) Applicant: The Regents of the University of California, Oakland, CA (US)

(72) Inventors: Theerapat Yangyuenthanasan, Berkeley, CA (US); Wayne Tung, Berkeley, CA (US); Homayoon Kazerooni, Berkeley, CA (US)

(73) Assignees: The Regents of the University of California, Oakland, CA (US); U.S. Bionics, Inc., Emeryville, CA (US)

( * ) Notice: Subject to any disclaimer, the term of this patent is extended or adjusted under 35 U.S.C. 154(b) by 511 days.

(21) Appl. No.: 16/360,969

(22) Filed: Mar. 21, 2019

(65) Prior Publication Data

US 2019/0216630 A1    Jul. 18, 2019

Related U.S. Application Data

(60) Division of application No. 15/654,929, filed on Jul. 20, 2017, now Pat. No. 10,285,843, which is a
(Continued)

(51) Int. Cl.
*A61H 3/00*      (2006.01)
*A61F 5/02*      (2006.01)
(Continued)

(52) U.S. Cl.
CPC ............ *A61F 5/026* (2013.01); *A61F 5/028* (2013.01); *A61H 1/0244* (2013.01);
(Continued)

(58) Field of Classification Search
CPC ...... A61H 1/0244; A61H 1/0292; A61H 3/00; A61H 2003/007; A61F 5/026; A61F 5/028; A61F 2005/0179; B25J 9/0006
See application file for complete search history.

(56) References Cited

U.S. PATENT DOCUMENTS 1,202,851 A    10/1916   Kelly
1,409,326 A    3/1922   Williamson
(Continued)

FOREIGN PATENT DOCUMENTS

CN    201934433 U    8/2011
CN    108471865 A    8/2018
(Continued)

OTHER PUBLICATIONS

"International Application Serial No. PCT/US15/61284, dated Apr. 11, 2016", 14 pages.
(Continued)

*Primary Examiner* — Timothy A Stanis
(74) *Attorney, Agent, or Firm* — Sterne, Kessler, Goldstein & Fox P.L.L.C.

(57) ABSTRACT

A trunk supporting exoskeleton comprises: a supporting trunk; thigh links configured to move in unison with a wearer's thighs; and first and second torque generators located on both left and right halves of the wearer substantially close to the wearer's hip. The torque generators couple the supporting trunk to the thigh links, and generate torque between the thigh links and the supporting trunk. When the wearer bends forward such that a predetermined portion of the supporting trunk passes beyond a predetermined angle from vertical, a torque generator(s) imposes a resisting torque between the supporting trunk and the thigh link(s), causing the supporting trunk to impose a force against the wearer's trunk, and the thigh link(s) to impose a force onto the wearer's thigh. When the predetermined portion does not pass beyond the predetermined angle, the torque generators impose no resisting torques between said supporting trunk and respective thigh links.

19 Claims, 68 Drawing Sheets

Related U.S. Application Data continuation-in-part of application No. 14/944,635, filed on Nov. 18, 2015, now Pat. No. 9,744,066, which is a continuation-in-part of application No. 14/125,117, filed as application No. PCT/US2012/041891 on Jun. 11, 2012, now Pat. No. 9,655,762.

(60) Provisional application No. 61/495,484, filed on Jun. 10, 2011.

(51) Int. Cl.
*A61H 1/02* (2006.01)
*A61F 5/01* (2006.01)

(52) U.S. Cl.
CPC ........... *A61H 1/0292* (2013.01); *A61H 3/008* (2013.01); *A61F 2005/0179* (2013.01); *A61H 2003/007* (2013.01); *A61H 2201/1246* (2013.01); *A61H 2201/1261* (2013.01); *A61H 2201/164* (2013.01); *A61H 2201/165* (2013.01); *A61H 2201/1619* (2013.01)

(56) References Cited

U.S. PATENT DOCUMENTS

| | | | |
|---|---|---|---|
| 3,790,209 | A | 2/1974 | Littmann |
| 4,256,098 | A | 3/1981 | Swan et al. |
| 4,342,140 | A | 8/1982 | Lacey |
| 4,745,911 | A | 5/1988 | Bender |
| 4,829,989 | A | 5/1989 | Deamer et al. |
| 5,127,897 | A | 7/1992 | Roller |
| 5,152,730 | A | 10/1992 | Hoffman |
| 5,176,622 | A | 1/1993 | Anderson et al. |
| 5,207,635 | A | 5/1993 | Richards et al. |
| 5,248,293 | A | 9/1993 | Hubbard et al. |
| 5,259,833 | A | 11/1993 | Barnett |
| 5,275,426 | A * | 1/1994 | Tankersley ............ A61H 3/008 135/67 |
| 5,314,404 | A | 5/1994 | Boughner et al. |
| 5,799,847 | A * | 9/1998 | Sandor .................... A45F 5/02 224/197 |
| 5,951,591 | A | 9/1999 | Roberts |
| 6,056,673 | A | 5/2000 | Arrecis |
| 6,283,348 | B1 | 9/2001 | Wang |
| 6,436,065 | B1 | 8/2002 | Mitchell |
| 7,553,266 | B2 | 6/2009 | Abdoli-Eramaki |
| 7,744,552 | B1 | 6/2010 | Babcock |
| 8,033,518 | B2 | 10/2011 | Schuchman |
| 8,060,945 | B2 | 11/2011 | Adarraga |
| 8,568,344 | B2 | 10/2013 | Ferguson et al. |
| 9,022,956 | B2 | 5/2015 | Kazerooni et al. |
| 9,655,762 | B2 | 5/2017 | Kazerooni et al. |
| 9,744,066 | B2 | 8/2017 | Kazerooni et al. |
| 10,285,843 | B2 | 5/2019 | Yangyuenthanasan et al. |
| 10,357,392 | B2 | 7/2019 | Kazerooni et al. |
| 2004/0232180 | A1 | 11/2004 | Badillo |
| 2005/0130815 | A1 | 6/2005 | Abdoli-Eramaki |
| 2005/0158117 | A1 | 7/2005 | Arnold et al. |
| 2006/0113147 | A1* | 6/2006 | Harris ................. A62B 35/0093 182/3 |
| 2007/0090143 | A1 | 4/2007 | Clayton et al. |
| 2008/0161738 | A1 | 7/2008 | Giesen |
| 2008/0228121 | A1 | 9/2008 | Hughes |
| 2009/0292369 | A1 | 11/2009 | Kazerooni et al. |
| 2010/0094185 | A1 | 4/2010 | Amundson et al. |
| 2010/0125230 | A1 | 5/2010 | Hurley |
| 2010/0298746 | A1 | 11/2010 | Shimizu et al. |
| 2011/0098617 | A1 | 4/2011 | Ferguson et al. |
| 2011/0105966 | A1 | 5/2011 | Kazerooni et al. |
| 2011/0111932 | A1 | 5/2011 | Hoffmann et al. |
| 2011/0266323 | A1 | 11/2011 | Kazerooni et al. |
| 2012/0136292 | A1 | 5/2012 | Pepin |
| 2014/0121573 | A1 | 5/2014 | Kazerooni et al. |
| 2014/0331457 | A1 | 11/2014 | Perreault |
| 2015/0142130 | A1 | 5/2015 | Goldfarb et al. |
| 2016/0206498 | A1 | 7/2016 | Kazerooni et al. |
| 2017/0196712 | A1 | 7/2017 | Kazerooni et al. |
| 2019/0231574 | A1 | 8/2019 | Kazerooni et al. |

FOREIGN PATENT DOCUMENTS

| | | |
|---|---|---|
| DE | 19652516 A1 | 6/1998 |
| DE | 202009000076 U1 | 4/2010 |
| EP | 3376895 A1 | 9/2018 |
| JP | H01274758 A | 11/1989 |
| JP | H03165765 A | 7/1991 |
| JP | H09552 A | 1/1997 |
| JP | 2007020672 A | 2/2007 |
| JP | 2007097636 A | 4/2007 |
| JP | 2007130234 A | 5/2007 |
| JP | 2007282991 A | 11/2007 |
| JP | 2009011818 A | 1/2009 |
| JP | 2015163180 A | 9/2015 |
| JP | 6571869 B2 | 9/2019 |
| KR | 102083035 B1 | 2/2020 |
| WO | 2010011848 A1 | 1/2010 |
| WO | 2019017949 A1 | 1/2019 |

OTHER PUBLICATIONS

"Int'l Application Serial No. PCT/US15/61284, ISRWO dated Apr. 11, 2016", 26 pages.

"Int'l Application Serial No. PCT/US17/43057, Int'l Search Report and Written Opinion dated Nov. 2, 2017", 10 pages.

"U.S. Appl. No. 14/125,117, Examiner Interview dated Jan. 12, 17", 4 pages.

"U.S. Appl. No. 14/125,117, Examiner Interview Summary dated Mar. 23, 2016", 4 pages.

"U.S. Appl. No. 14/125,117, Final Office Action dated Aug. 12, 2016", 19 pages.

"U.S. Appl. No. 14/125,117, Non Final Office Action dated Jan. 11, 2016", 20 pages.

"U.S. Appl. No. 14/125,117, Notice of Allowance dated Feb. 10, 2017", 8 pages.

"U.S. Appl. No. 14/944,635, Examiner Interview Summary dated Apr. 27, 2017", 1 page.

"U.S. Appl. No. 14/944,635, Examiner Interview Summary dated Mar. 21, 2017", 3 pages.

"U.S. Appl. No. 14/944,635, Non Final Office Action dated Nov. 4, 2016", 24 pages.

"U.S. Appl. No. 14/944,635, Notice of Allowance dated Apr. 27, 2017", 11 pgs.

"U.S. Appl. No. 14/944,635, Restriction Requirement dated Jun. 27, 2016", 8 pages.

U.S. Appl. No. 15/654,929, Non Final Office Action dated May 16, 2018, 27 pgs.

U.S. Appl. No. 15/654,929, Notice of Allowance dated Dec. 19, 2018, 13 pgs.

U.S. Appl. No. 15/654,929, Restriction Requirement dated Nov. 2, 2017, 6 pgs.

\* cited by examiner

TRUNK SUPPORTING EXOSKELETON AND METHOD OF USE

CROSS-REFERENCE TO RELATED APPLICATIONS

This application is a divisional of U.S. Ser. No. 15/654,929, file Jul. 20, 2017, which is a continuation-in-part of U.S. patent application Ser. No. 14/944,635, filed Nov. 18, 2015 and issued as U.S. Pat. No. 9,744,066 on Aug. 29, 2017, which is a continuation-in-part of U.S. patent application Ser. No. 14/125,117, filed on Dec. 11, 2013 and issued as U.S. Pat. No. 9,655,762 on May 23, 2017, which claims priority to PCT application PCT/US12/41891, filed Jun. 11, 2012, which claims the benefit of U.S. patent application 61/495,484, filed Jun. 10, 2011, all of which are incorporated by reference in their entirety and for all purposes along with all other references cited in this application.

GOVERNMENT LICENSE RIGHTS

This invention was made with government support under Grant No. 1317978 and Grant No. 1456369 awarded by the National Science Foundation (NFS). The government has certain rights in the invention.

BACKGROUND

The present disclosure relates generally to exoskeletons, and more particularly, to trunk supporting exoskeletons to reduce muscle forces in a wearer's back.

In general, back support devices, which are configured to assist a wearer in bending, lifting and/or standing upright, are known in the art. U.S. Pat. Nos. 6,436,065, 5,951,591, 5,176,622, and 7,744,552. U.S. Pat. Nos. 1,409,326 and 4,829,989 describe devices where moment is created during a bend to counteract the moments from a wearer's trunk gravity weight. Conventional systems utilize a passive, spring resistance to create a torque between the wearer's torso and legs. By creating a restorative moment at the hip, the probability of injury of the L5/S1 area of the spine is greatly reduced. Once the angle between torso and leg reaches a predetermined angle during stooping, squatting, or walking, the devices provide resistance. However, none of the devices differentiate between walking and bending or sitting and bending. This means the wearer cannot walk comfortably, using these passive devices since the wearer's legs must push against the devices during walking. Similarly, the wearer cannot sit comfortably using these passive devices since the wearer's legs must push against the devices during sitting. This is uncomfortable and hazardous, preventing the wearer from moving around unrestricted, and is the most important reason to avoid the use of these systems in various industrial settings.

SUMMARY

The present disclosure is directed to a trunk supporting exoskeleton, which is configured to be worn by a wearer to reduce the muscle forces in the wearer's back during forward lumbar flexion. In general, the trunk supporting exoskeleton comprises: a supporting trunk which is configured to be coupled to the wearer's trunk; two thigh links which are configured to move in unison with the wearer's thighs in a manner resulting in flexion and extension of respective thigh links relative to the supporting trunk; and two torque generators located on both left and right halves of the wearer substantially close to the wearer's hip. The torque generators couple the supporting trunk to the respective thigh links and are configured to generate torque between the thigh links and the supporting trunk. In operation when the wearer bends forward in the sagittal plane such that a predetermined portion of the supporting trunk passes beyond a predetermined angle from the vertical gravity line, at least one of the first or second torque generators imposes a resisting torque between the supporting trunk and at least one of the thigh links. This causes the supporting trunk to impose a force against the wearer's trunk and at least one of the thigh links to impose a force onto the wearer's thigh. When the predetermined portion of the supporting trunk does not pass beyond the predetermined angle from the vertical gravity line, the first and second torque generators, during the entire range of motion of the thigh links, impose no resisting torques between the supporting trunk and the respective thigh links.

Other objects, features, and advantages of the present disclosure will become apparent upon consideration of the following detailed description and the accompanying drawings, in which like reference designations represent like features throughout the figures.

DETAILED DESCRIPTION

Figure 1:
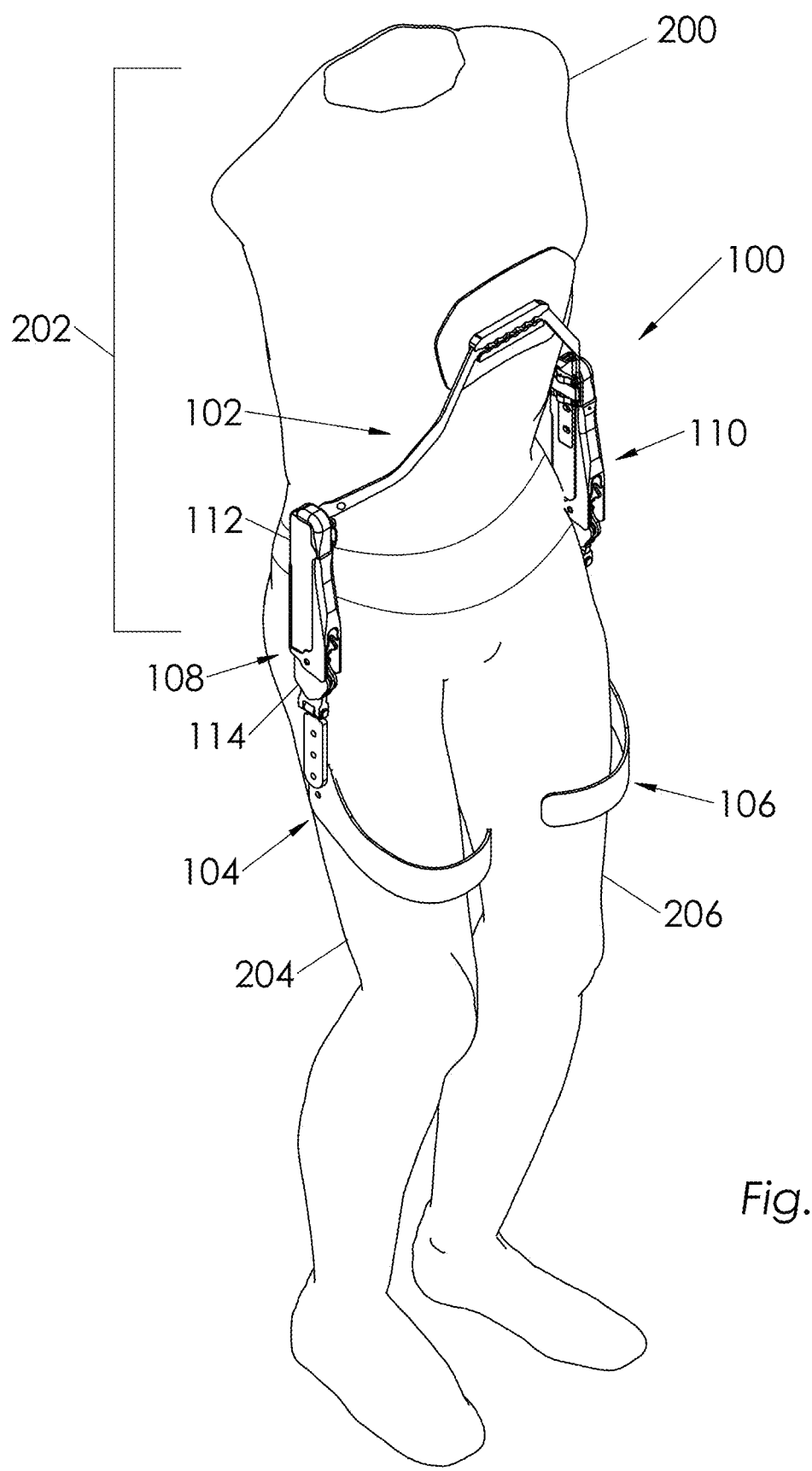
FIG. 1 shows a trunk supporting exoskeleton of the present disclosure.
Figure 2:
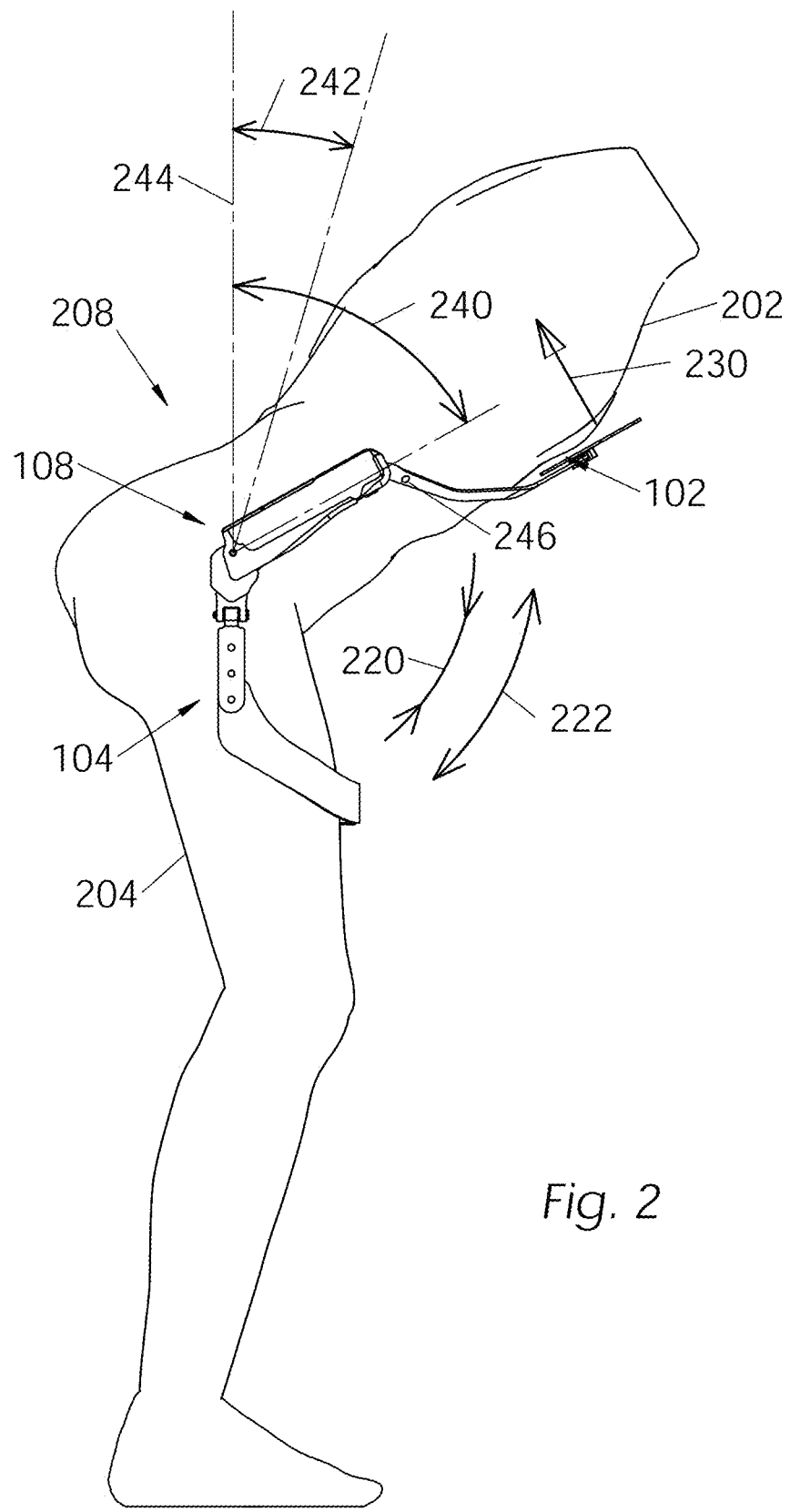
FIG. 2 shows a trunk supporting exoskeleton of the present disclosure on a forward leaning wearer.

FIG. 1 shows an embodiment of Trunk Support Exoskeleton 100. It is configured to be worn by a wearer 200 to reduce the muscle forces in the wearer's back during forward lumbar flexion. FIG. 2 shows wearer 200 during forward lumbar flexion. Trunk Support Exoskeleton 100 comprises a supporting trunk 102 which is configured to be coupled to wearer's trunk 202. Wearer's trunk 202 is defined as the central part of the human from which the neck and limbs extend. The trunk includes the thorax and the abdomen.

Trunk Support Exoskeleton 100 further comprises a first thigh link 104 and a second thigh link 106 which are configured to couple to respective thighs 204 and 206 of wearer 200. As shown in FIG. 1, first thigh link 104 and second thigh link 106 are configured to move in unison with wearer's thighs 204 and 206, respectively, in a manner resulting in flexion and extension of respective first and second thigh links 104 and 106 relative to supporting trunk 102. Flexion of first thigh link 104 relative to supporting trunk 102 is defined as when first thigh link 104 and supporting trunk 102 rotate towards to each other. This is shown by arrow 220 in FIG. 2. Flexion of second thigh link 106 relative to supporting trunk 102 is defined similarly. Extension of first thigh link 104 relative to supporting trunk 102 is defined as when first thigh link 104 and supporting trunk 102 rotate away from each other. This is shown by arrow 222 in FIG. 2. Extension of second thigh link 106 relative to supporting trunk 102 is defined similarly.

Trunk support exoskeleton 100 further comprises a first torque generator 108 and a second torque generator 110. First torque generator 108 is configured to generate a torque between first thigh link 104 and supporting trunk 102. Second torque generator 110 is configured to generate a torque between second thigh link 106 and supporting trunk 102. In some embodiments, first and second torque generators 108 and 110 are located on the left and right halves of wearer 200 substantially close to wearer's hip.

In operation, when wearer 200 bends forward in the sagittal plane such that a predetermined portion of supporting trunk 102 passes beyond a predetermined angle 242 from vertical 244, at least one of the first or second torque generators 108 and 110 imposes a resisting torque between supporting trunk 102 and at least one of the first and second thigh links 104 and 106. This causes supporting trunk 102 to impose a supporting trunk force 230 against wearer's trunk 202. In the embodiment of FIG. 2, supporting trunk force 230 is generally imposed on wearer's chest area 210. At the same time, at least one of the first and second thigh links 104 and 106 impose a force onto wearer's thighs 204 and 206. Supporting trunk force 230 imposed by supporting trunk 102 against wearer's trunk 202 helps reduce the muscle forces at the wearer's lower back at the general area of 208.

Figure 3:
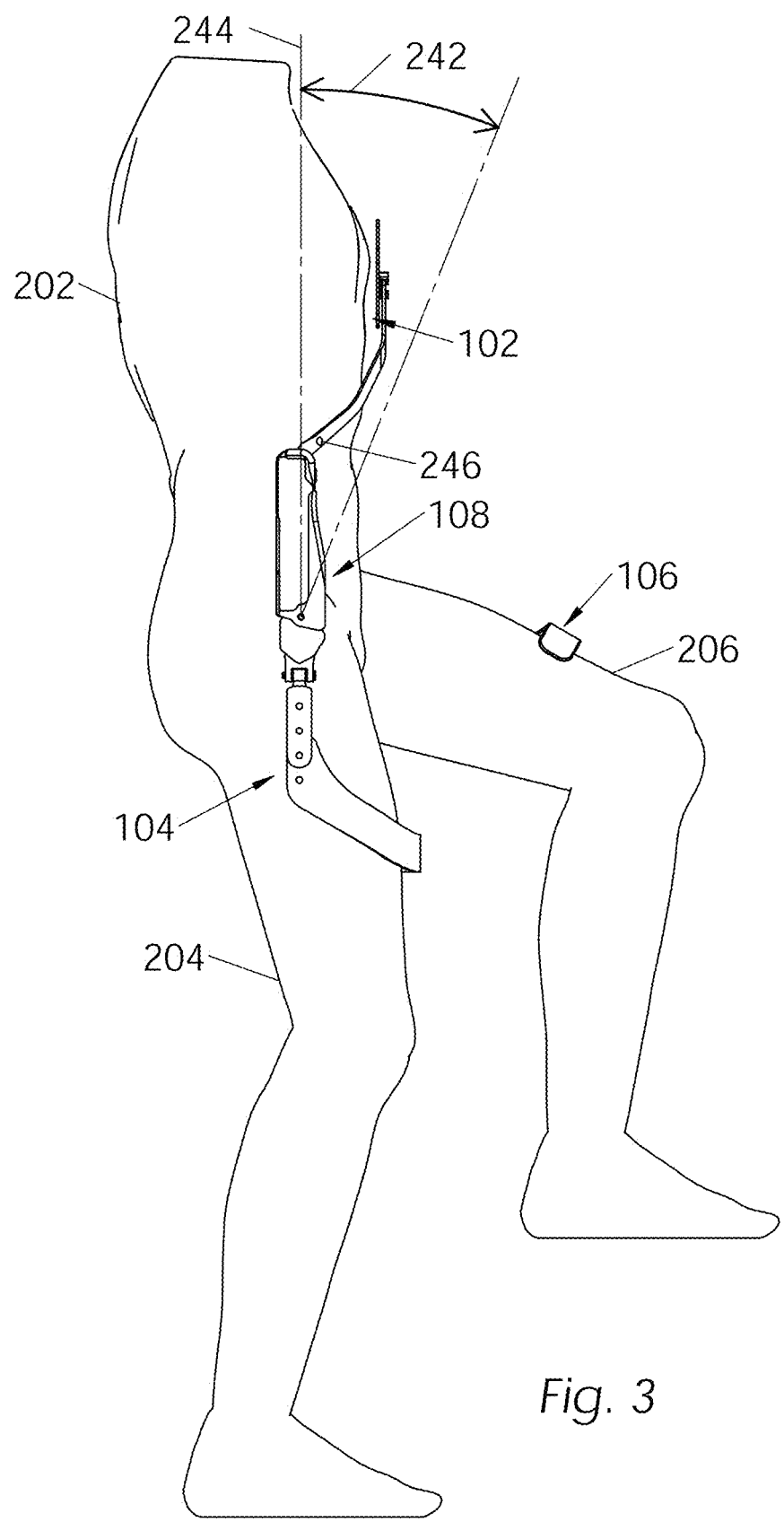
FIG. 3 depicts a trunk supporting exoskeleton of the present disclosure.

As shown in FIG. 3, when wearer 200 is not in a bent position (i.e. when a predetermined portion of supporting trunk 102 does not pass beyond predetermined angle 242 from vertical), first and second torque generators 108 and 110, during the entire range of motion of first and second thigh links 104 and 106, impose no resisting torques between supporting trunk 102 and the respective first and second thigh links 104 and 106. This means as long as wearer 200 is not in a bent position (i.e. when a predetermined portion of supporting trunk 102 does not pass beyond predetermined angle 242 from vertical 244 as shown in FIG. 3), wearer 200 can walk, ascend and descend stairs and ramps without any force imposed on wearer 200 from supporting trunk 102. However, if wearer 200 bends forward in the sagittal plane (i.e. when a predetermined portion of supporting trunk 102 passes beyond predetermined angle 242 from vertical 244 as shown in FIG. 2), supporting trunk force 230 from supporting trunk 102 will help support wearer's trunk 202. FIG. 2 shows an example where wearer 200 is bent. FIG. 3 shows an example where wearer 200 is not bent. FIG. 2 also shows an embodiment where predetermined angle from vertical is shown by 242. In this embodiment, a predetermined portion of supporting trunk 102 is shown by 246. Since wearer 200 has bent in FIG. 2 and predetermined portion 246 has passed beyond predetermined angle 242, as represented by arrow 240, supporting trunk force 230 is imposed on wearer's trunk 202. Examples of predetermined angle 242 can be 5, 10 or 15 degrees. In some embodiments, predetermined angle 242 can be zero. Since wearer 200 has not bent in FIG. 3, predetermined portion 246 has not passed beyond predetermined angle 242 and no force is imposed on wearer's trunk 202.

Figure 4:
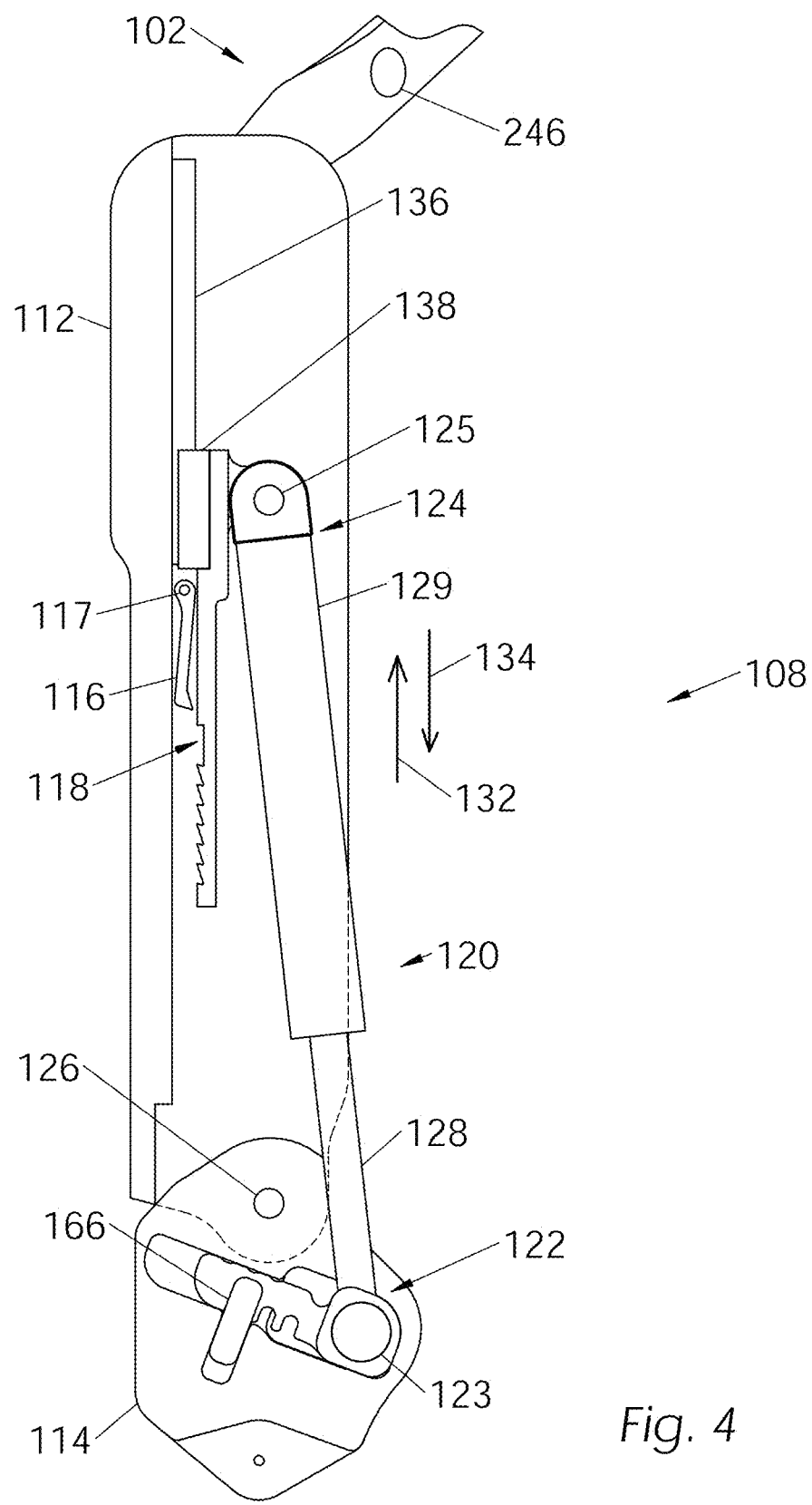
FIG. 4 depicts an embodiment of the torque generator.

FIG. 4 shows an embodiment of first torque generator 108. Second torque generator 110 is a mirrored body of first torque generator 108 thus only first torque generator 108 is described here. In embodiments, first torque generator 108, in addition to other components, comprises an upper bracket 112 configured to be coupled to supporting trunk 102. Supporting trunk 102 is not shown in FIG. 4, but this coupling is shown in FIGS. 1 and 2. First torque generator 108 further comprises a lower bracket 114 which is configured to be coupled to first thigh link 104, and rotatably coupled to upper bracket 112 around exoskeleton joint 126. In some embodiments, upper bracket 112 and lower bracket 114 rotate relative to each other round exoskeleton joint 126. First torque generator 108 further comprises pendulum 116 which is rotatably coupled to upper bracket 112 around pendulum joint 117. First torque generator 108 also comprises an engagement bracket 118 which is slidingly coupled to upper bracket 112. Arrows 132 and 134 show the sliding motion between engagement bracket 118 and upper bracket 112. In the embodiment of FIG. 4, the sliding motion is provided by rail 136 and carriage 138. Rail 136 is mounted on upper bracket 112. Carriage 138 is mounted on engagement bracket 118. First torque generator 108 additionally comprises a compression spring 120 which is rotatably coupled to lower bracket 114 from its first end 122 around first end joint 123. Compression spring 120 is also rotatably coupled to engagement bracket 118 from its second end 124 around second end joint 125. In some embodiments as shown in FIG. 4, compression spring 120 is a gas spring comprised of a rod 128 and a cylinder 129. In embodiments, first torque generator 108 also includes locking pin 166 is used to lock the position of sliding block 162 in channel 160.

In operation, when a predetermined portion 246 of supporting trunk 102 passes beyond predetermined angle 242 (as shown FIG. 5), pendulum 116 comes into contact with engagement bracket 118. This prevents engagement bracket 118 from sliding, causing compression spring 120 to be able to provide a resisting torque between upper bracket 112 and lower bracket 114. Further, when a predetermined portion of supporting trunk 102 does not pass beyond predetermined angle 242 (as shown in FIG. 6), pendulum 116 is not in contact with engagement bracket 118. This causes engagement bracket 118 to be free to slide on upper bracket 112. This means in this configuration, compression spring 120 is uncompressed and does not provide resisting torque between upper bracket 112 and lower bracket 114. In this situation, wearer 200 can walk, ascend and descend stairs and ramps freely.

Figure 5:
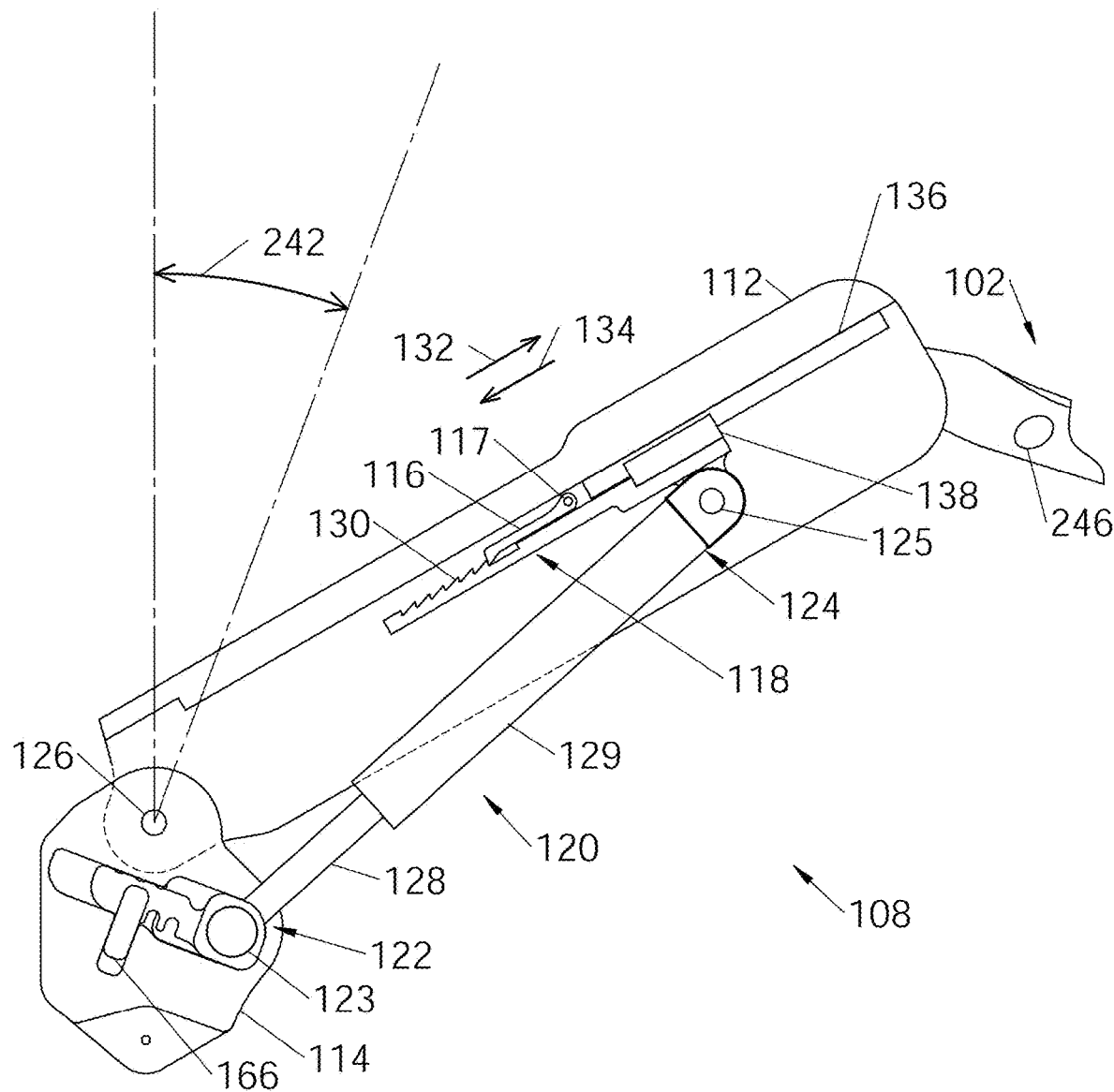
FIG. 5 depicts an embodiment of the torque generator.
Figure 6:
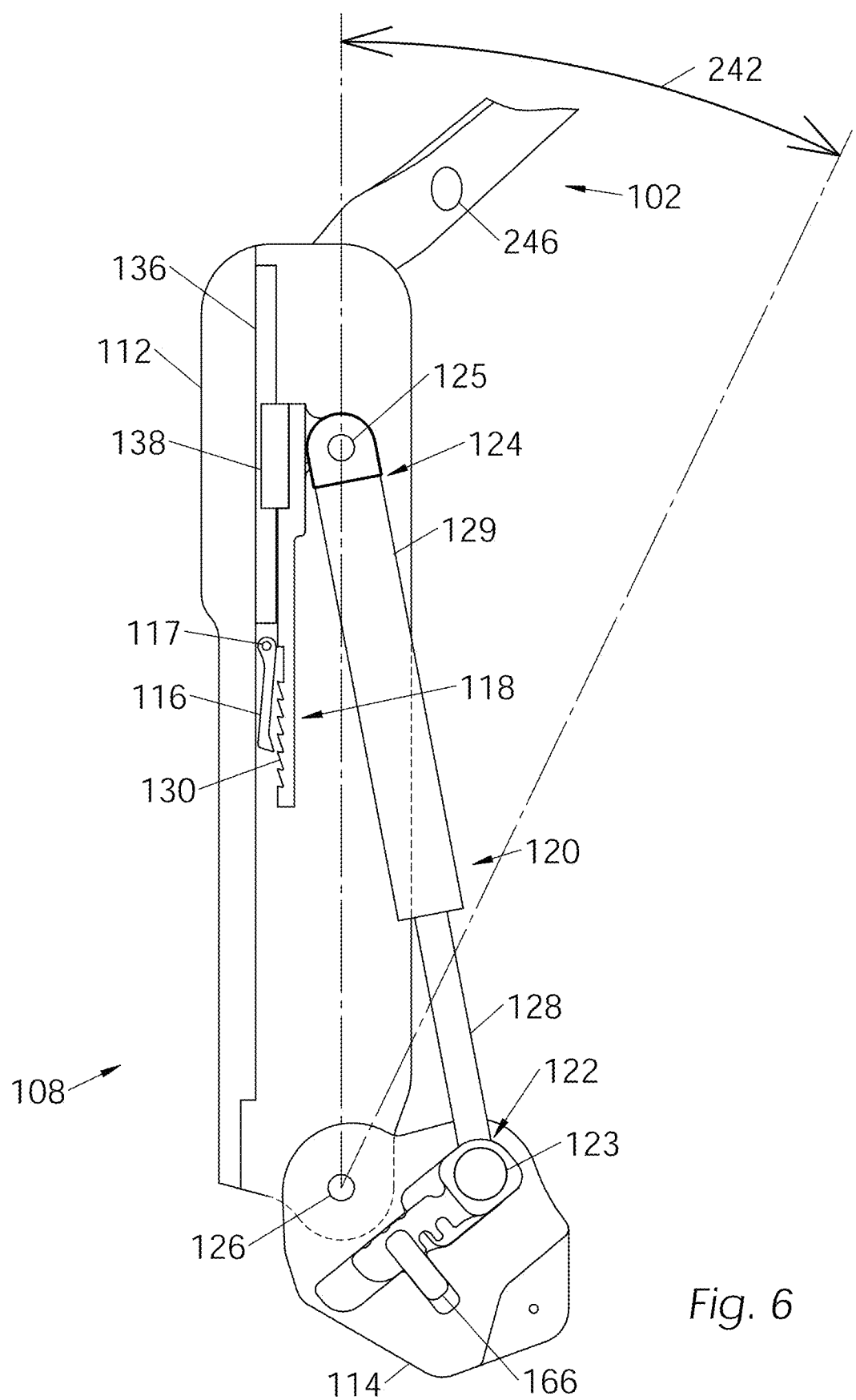
FIG. 6 depicts an embodiment of the torque generator.

FIGS. 5 and 6 show an embodiment of engagement bracket 118. In this embodiment, engagement bracket 118 comprises a few teeth 130. Engagement bracket 118 and pendulum 116 form a ratchet mechanism. A ratchet mechanism is a mechanical device that allows continuous linear or rotary motion in only one direction while preventing motion in the opposite direction. When pendulum 116 is in contact with engagement bracket 118, engagement bracket 118 cannot slide relative to pendulum 116 and upper bracket 112 along first direction 132, but is free to move along second direction 134. FIG. 5 shows a situation where a predetermined portion of supporting trunk 102 has passed beyond predetermined angle 242. Pendulum 116 has come into contact with engagement bracket 118 due to its weight force (i.e. under the force of gravity the weight of pendulum 116 causes it to swing into contact with engagement bracket 118). This prevents engagement bracket 118 from sliding along direction 132. This causes compression spring 120 to be compressed and to provide a resisting torque between upper bracket 112 and lower bracket 114.

Figure 7:
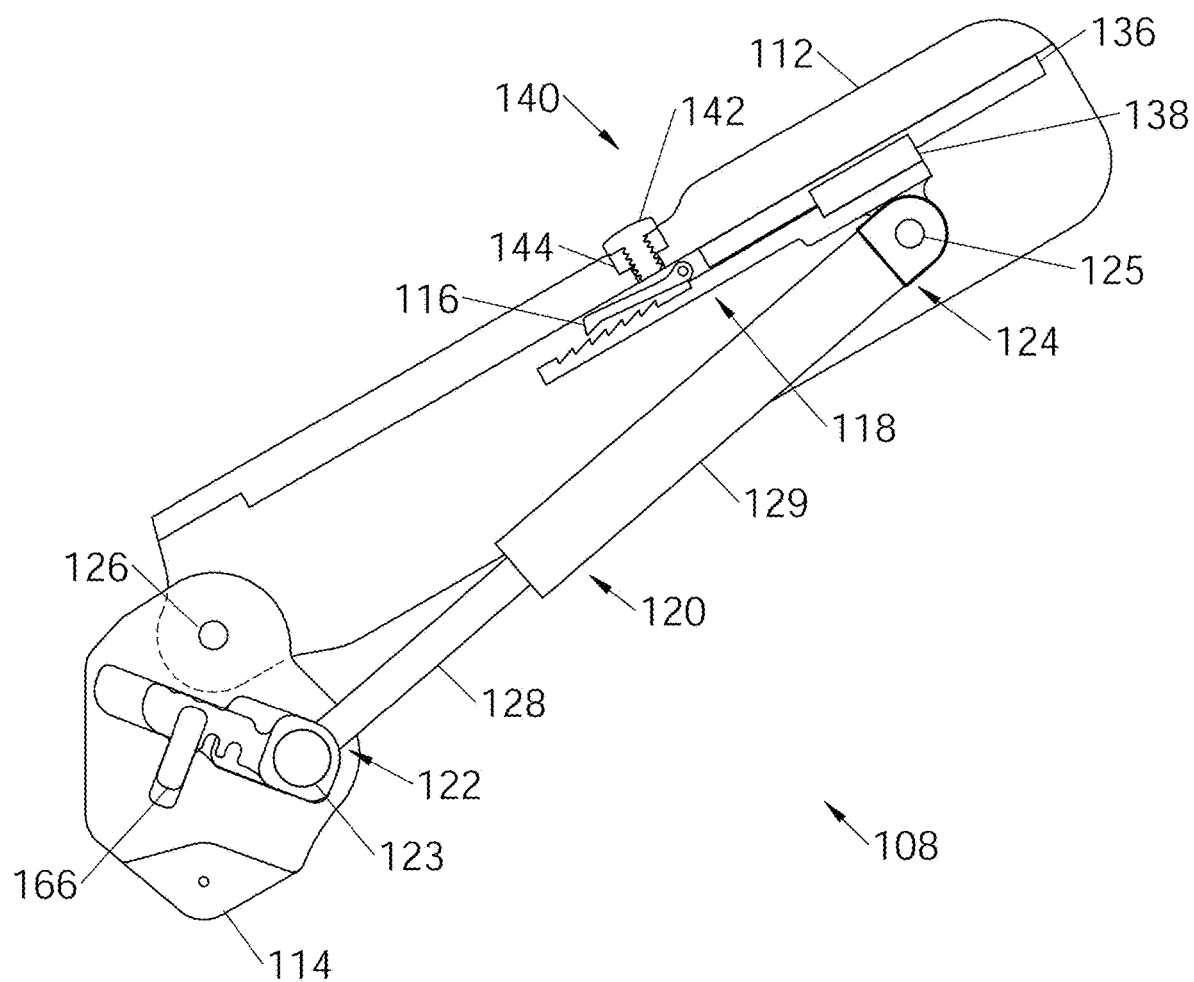
FIG. 7 depicts an embodiment of the torque generator.
Figure 8:
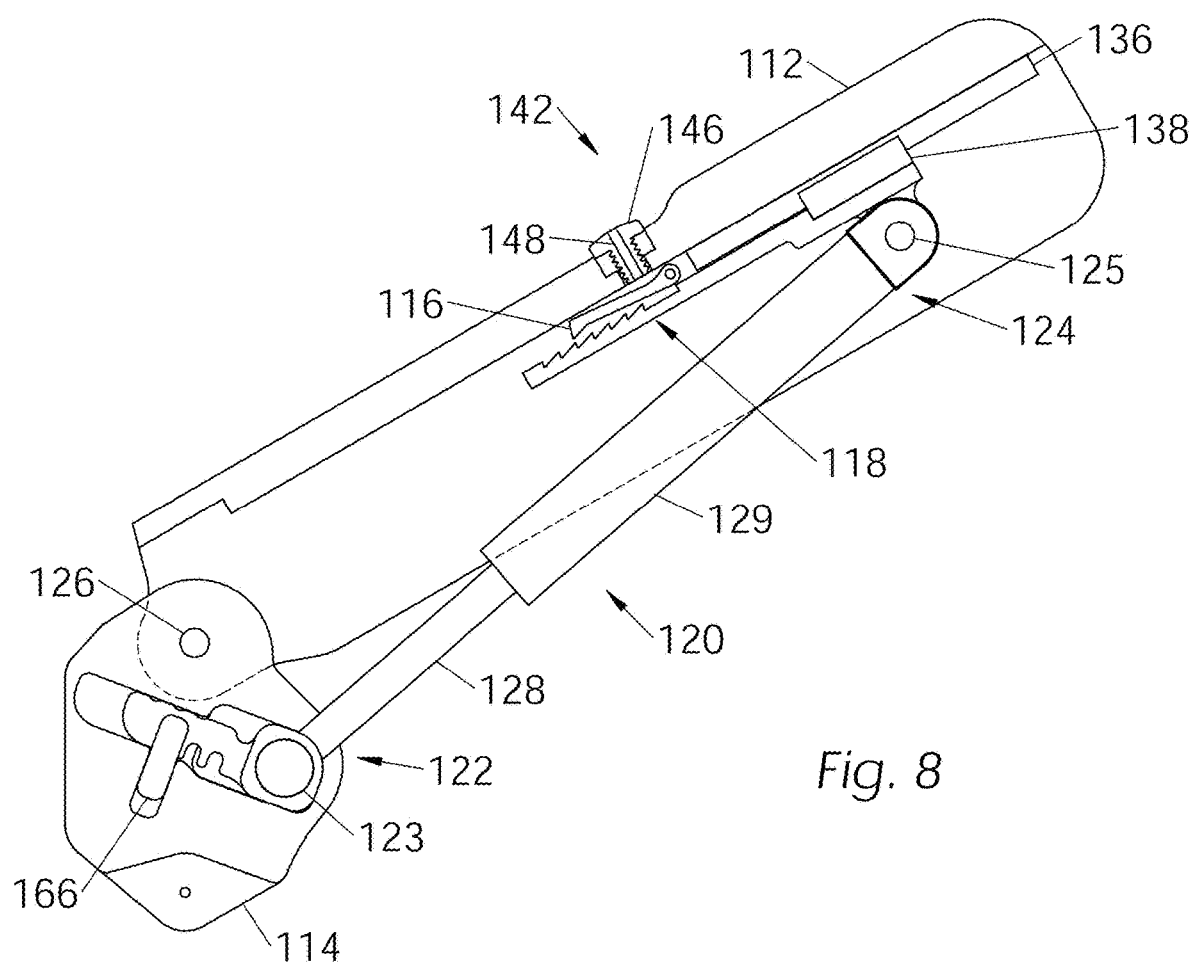
FIG. 8 depicts an embodiment of the torque generator.

FIG. 7 shows an embodiment of first torque generator 108. In this embodiment, first torque generator 108 further comprises of an angle adjustment mechanism 140 that allows the adjustment of predetermined angle 242. Adjustment mechanism 140 can be used to modify predetermined angle 242. In some embodiments as shown in FIG. 7 pendulum 116 is magnetic. Angle adjustment mechanism 140 further comprises a magnetic adjustment screw 142 located in an adjustment screw hole 144 on upper bracket 112 in close proximity to pendulum 116. In operation, when magnetic adjustment screw 142 is turned to change its position relative to pendulum 116, predetermined angle 242 changes. The closer magnetic adjustment screw 142 is to pendulum 116, the larger predetermined angle 242 would be. This is true because when magnetic adjustment screw 142 gets closer to pendulum 116, supporting trunk 102 and consequently upper bracket 112 have to bend more in order for the gravity force acting on pendulum 116 to overcome the magnetic force attracting pendulum 116 to magnetic adjustment screw 142. Adjustment mechanism 140 can be used to set predetermined angle 242 at desired angle. FIG. 8 shows an embodiment of magnetic adjustment screw 142. In this embodiment, magnetic adjustment screw 142 is comprised of an adjustment fastener 146 and an adjustment magnet 148 where adjustment magnet 148 is coupled to adjustment fastener 146. In some embodiments, as shown in FIG. 8, adjustment magnet 148 is inserted into adjustment fastener 146.

Figure 9:
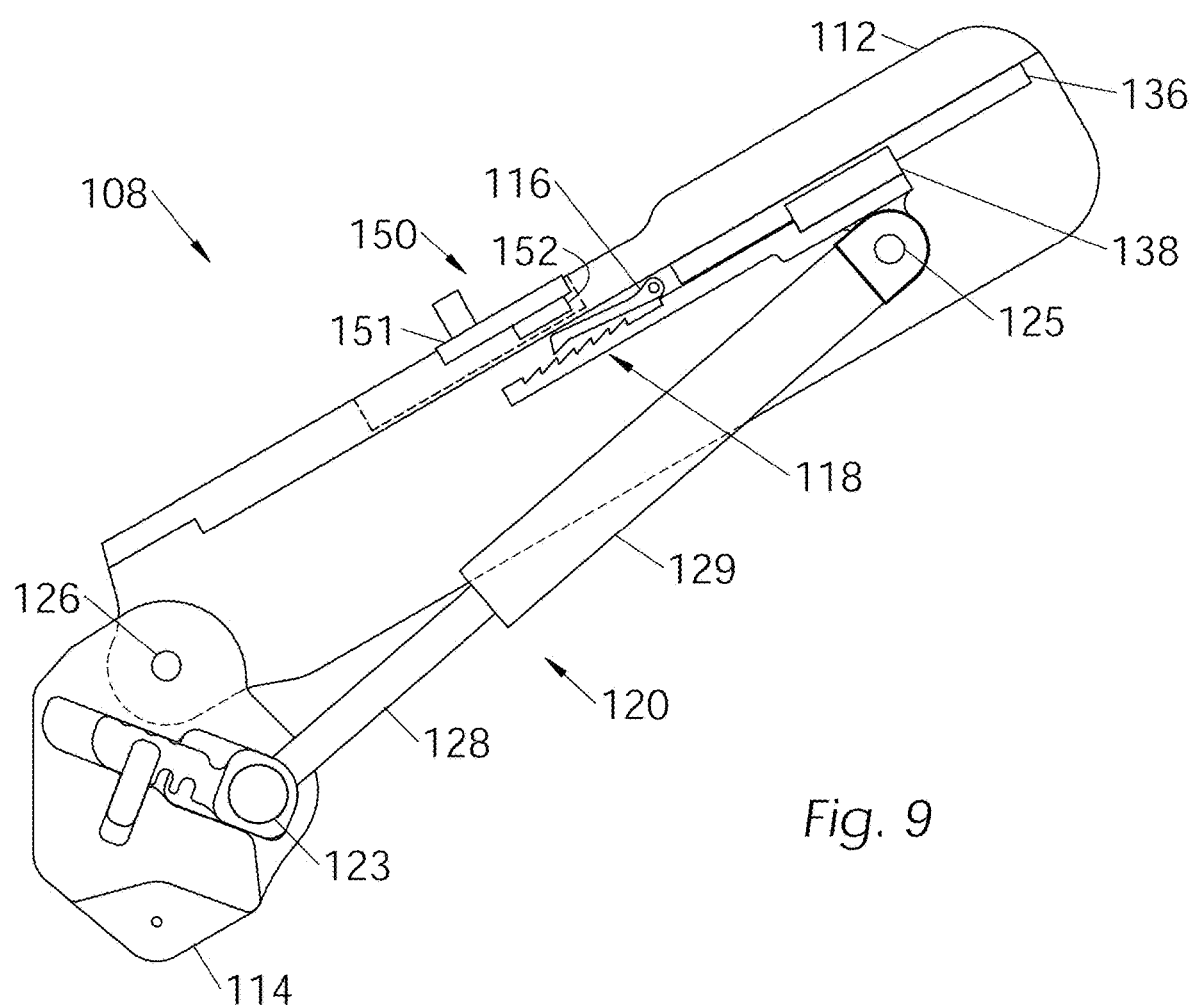
FIG. 9 depicts an embodiment of the torque generator.
Figure 10:
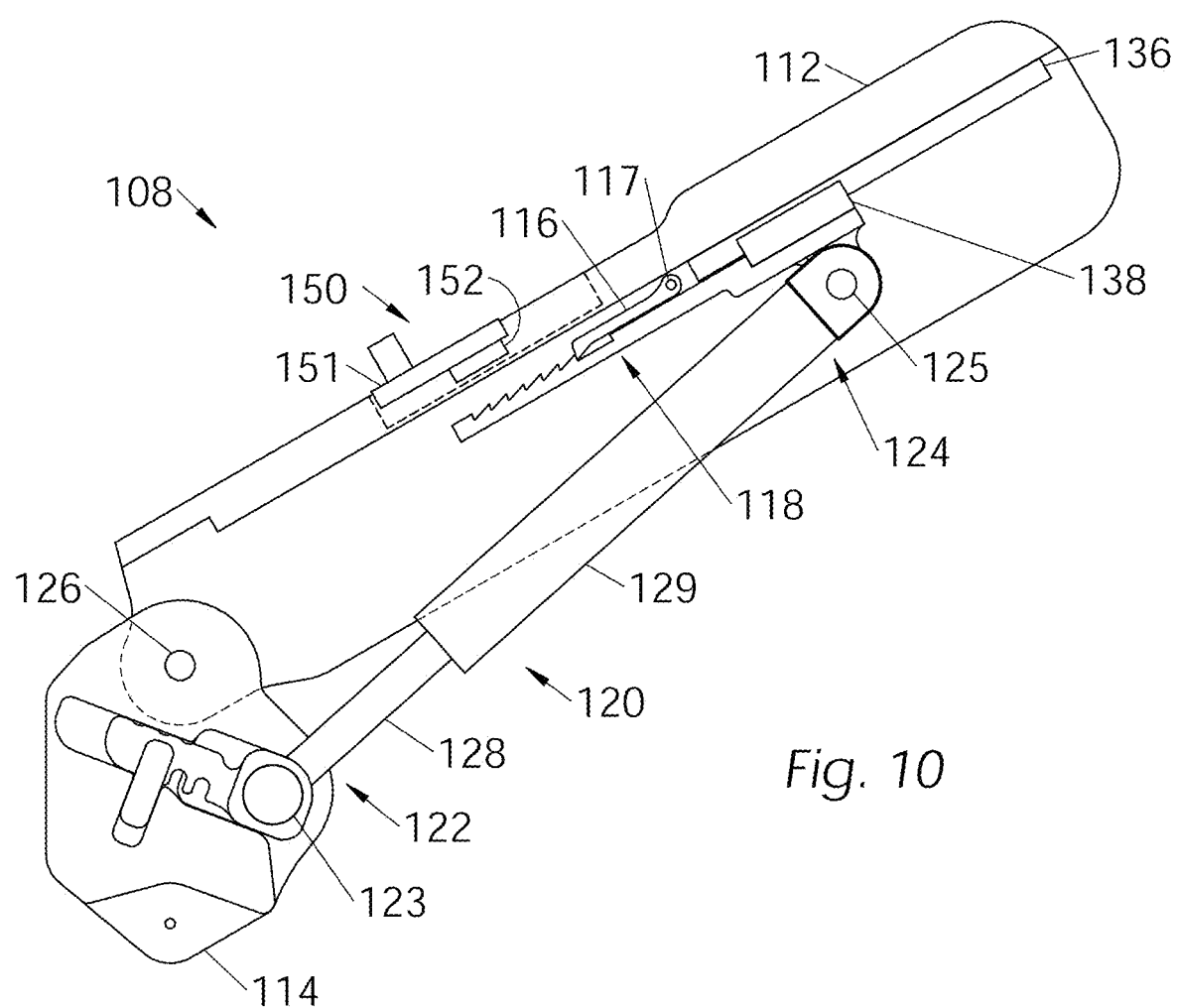
FIG. 10 depicts an embodiment of the torque generator.

FIG. 9 shows an embodiment of torque generator 108 where a manually manipulated override mechanism 150 is used to completely prevent pendulum 116 from contacting engagement bracket 118, and hence deactivate torque generator 108. In some embodiments, as shown in FIG. 9, pendulum 116 is magnetic and override mechanism 150 comprises of an override slider 151 sliding on upper bracket 112, and an override magnet 152 coupled to override slider 151. In operation, when a wearer shifts override slider 151 to its override position as shown in FIG. 9, override magnet 152 attracts pendulum 116 to its non-contacting position allowing engagement bracket 118 to move freely. When override slider 151 is moved to its non-override position as shown in FIG. 10, override magnet 152 does not attract pendulum 116 to its non-contacting position, allowing pendulum 116 to come into contact with engagement bracket 118 when a predetermined portion of supporting trunk 102 passes beyond predetermined angle 242. An ordinary wearer in the art would understand that there can be other methods of preventing pendulum 116 from contacting engagement bracket 118.

Figure 11:
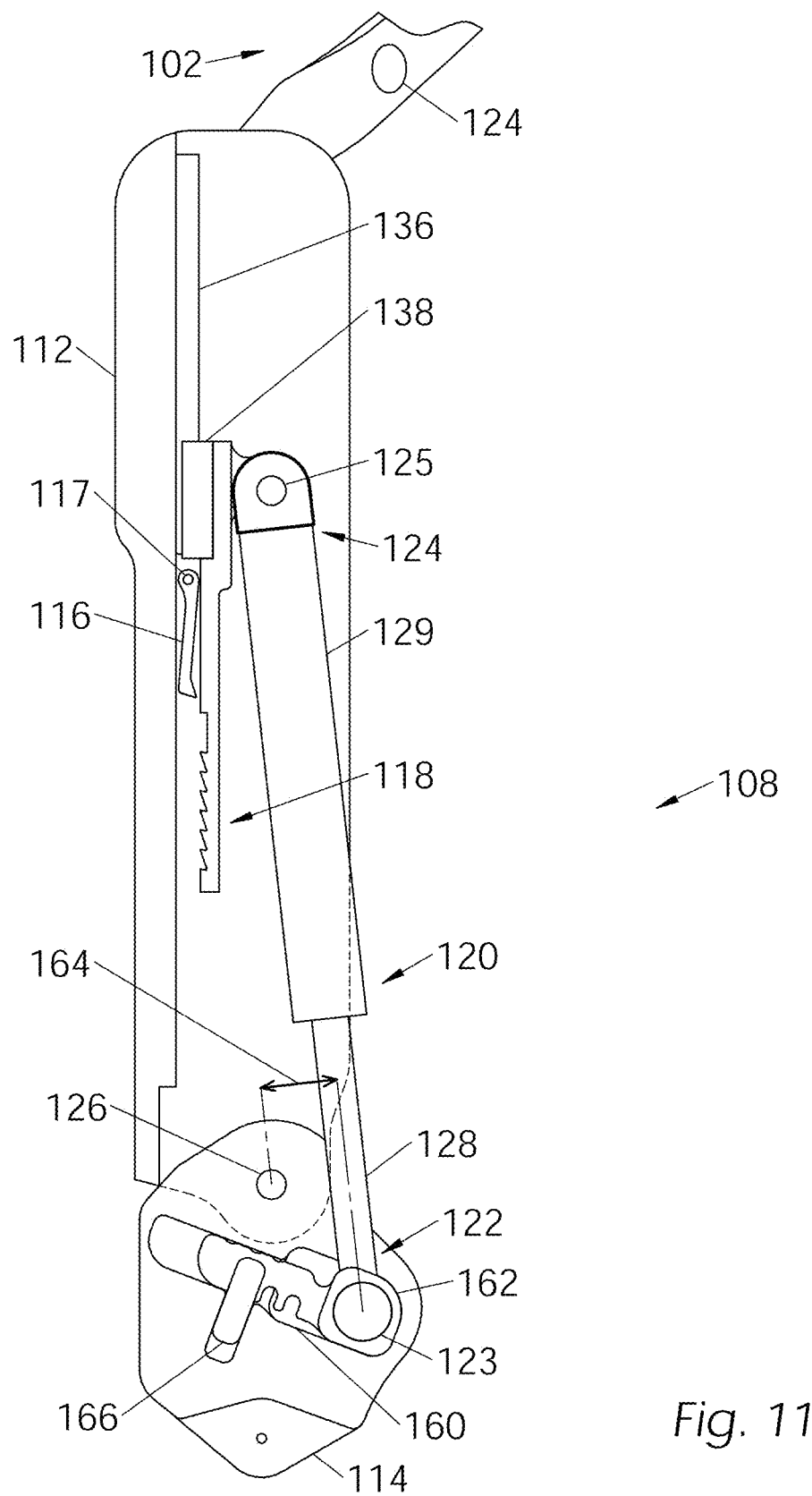
FIG. 11 depicts an embodiment of the torque generator.
Figure 12:
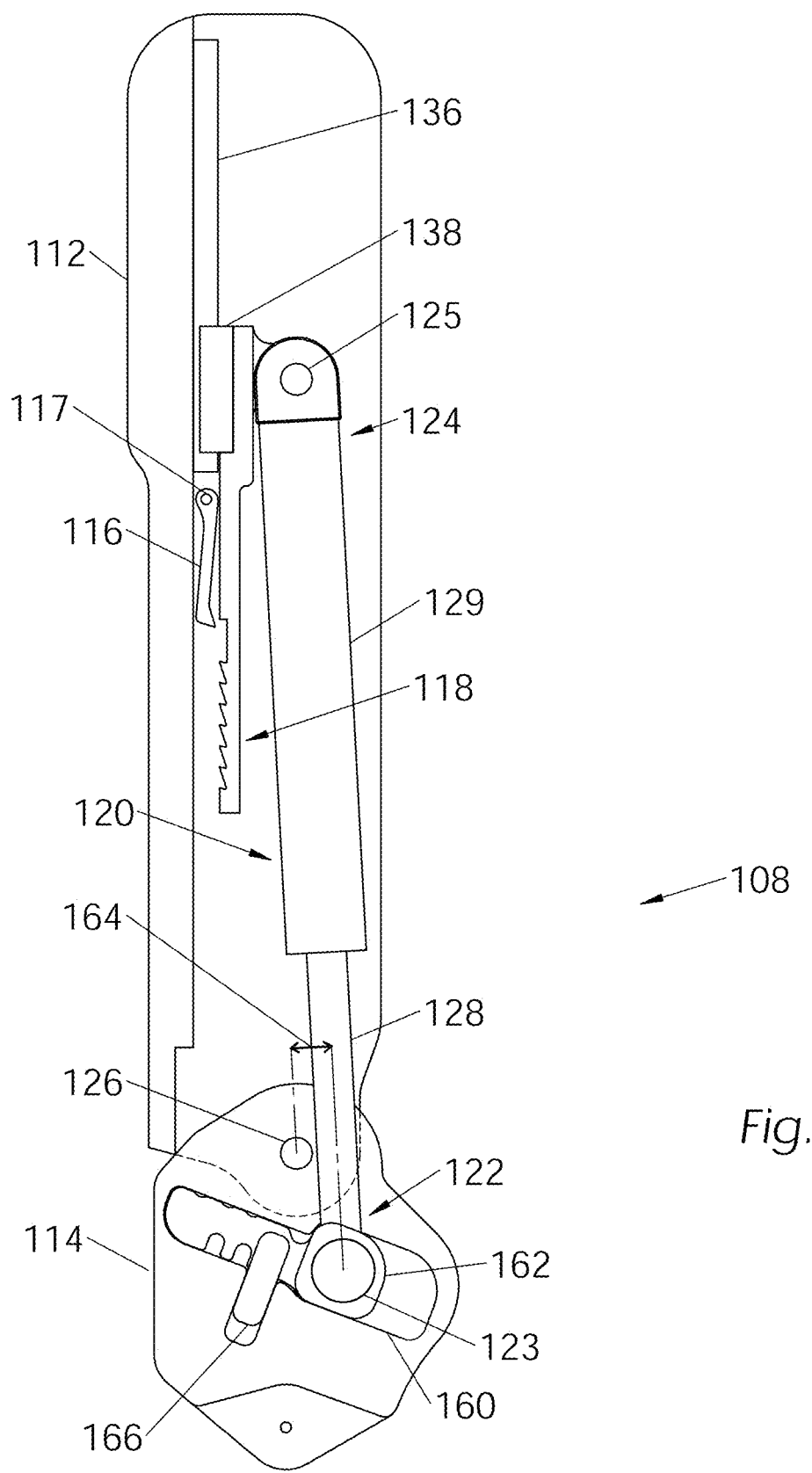
FIG. 12 depicts an embodiment of the torque generator.

The location of compression spring 120 relative to exoskeleton joint 126 determines the magnitude of torque output of torque generator 108. One can change the location of first end 122 of compression spring 120 to produce various torques. FIG. 11 shows a situation where the location of first end 122 of compression spring 120 is at a distance 164 from exoskeleton joint 126 which is farther than the distance 164 in FIG. 12, allowing for more torque. Accordingly, FIG. 12 shows the situation where the first end 122 of compression spring 120 is located closer to exoskeleton joint 126, wherein it produces less torque. A comparison of spring distance 164 in FIGS. 11 and 12 shows more torque can be provided when spring distance 164 is larger. In some embodiments, this torque adjustment is accomplished by changing the position of sliding block 162 inside a channel 160. Sliding block 162 is rotatably coupled to first end 122 of compression spring 120 and is capable of having several positions in channel 160. Channel 160 is formed inside lower bracket 114. In operation, adjusting the position of sliding block 162 in channel 160 allows for various positions of compression spring 120 relative to exoskeleton joint 126 thus various torque levels. Locking pin 166 is used to lock the position of sliding block 162 in channel 160. As can be seen in FIGS. 11 and 12 sliding block 162 has three positions. These positions are determined by three notches in sliding block 162. By positioning sliding block 162 in various locations and locking it by locking pin 166, one can provide various level of torque.

Figure 13:
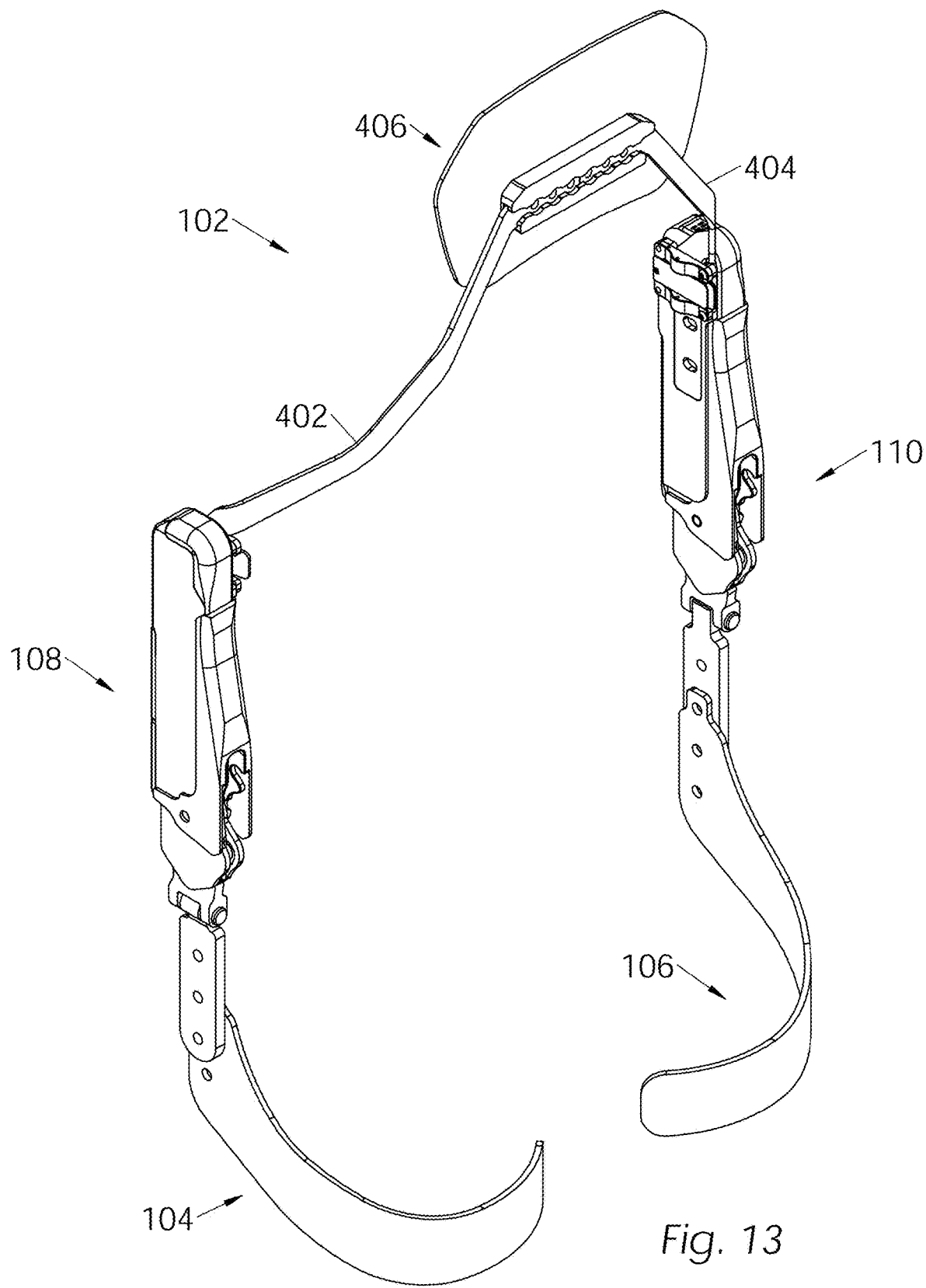
FIG. 13 depicts an embodiment of the supporting trunk.
Figure 14:
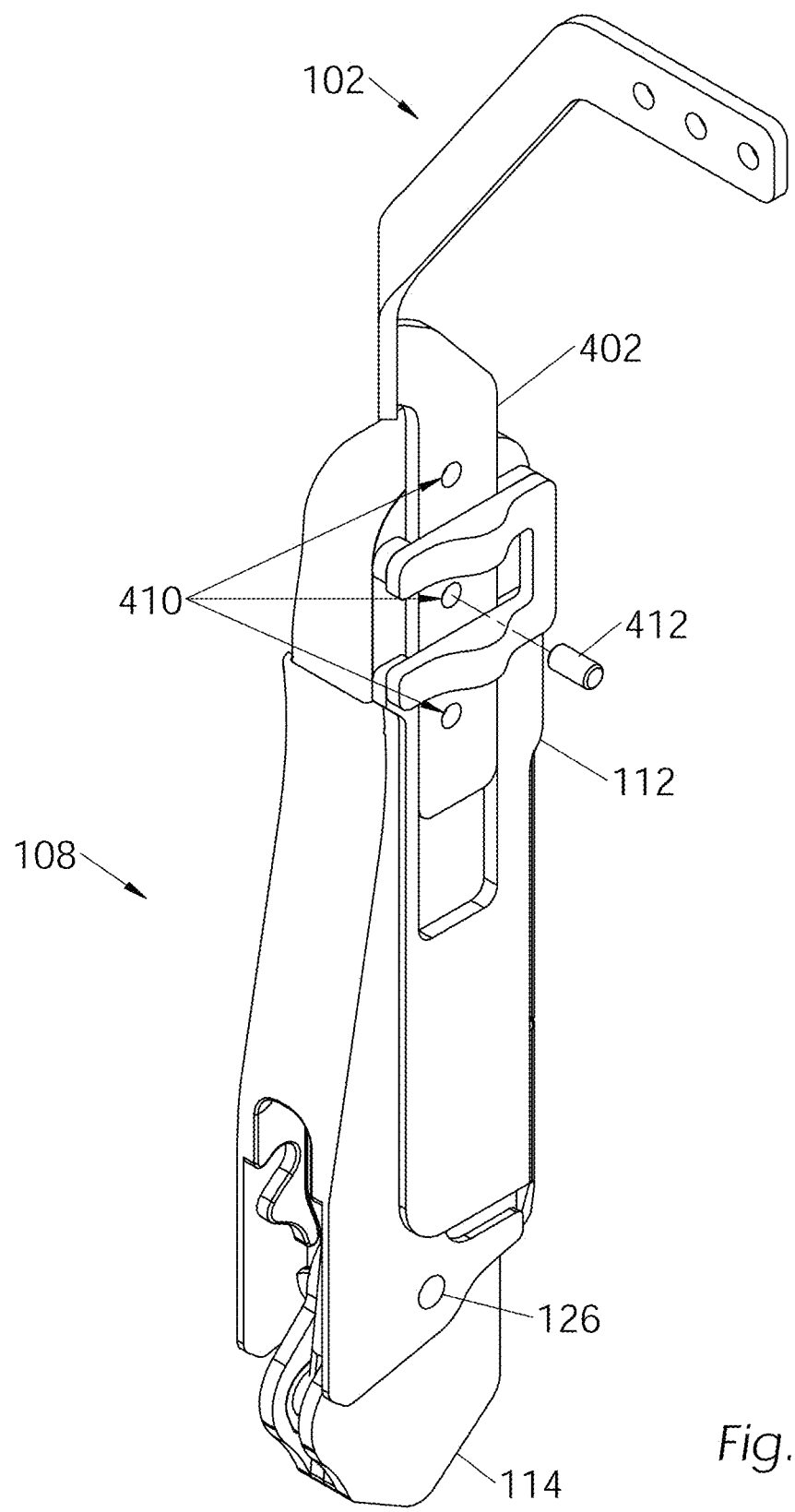
FIG. 14 depicts an embodiment of the adjustment of supporting trunk.
Figure 15:
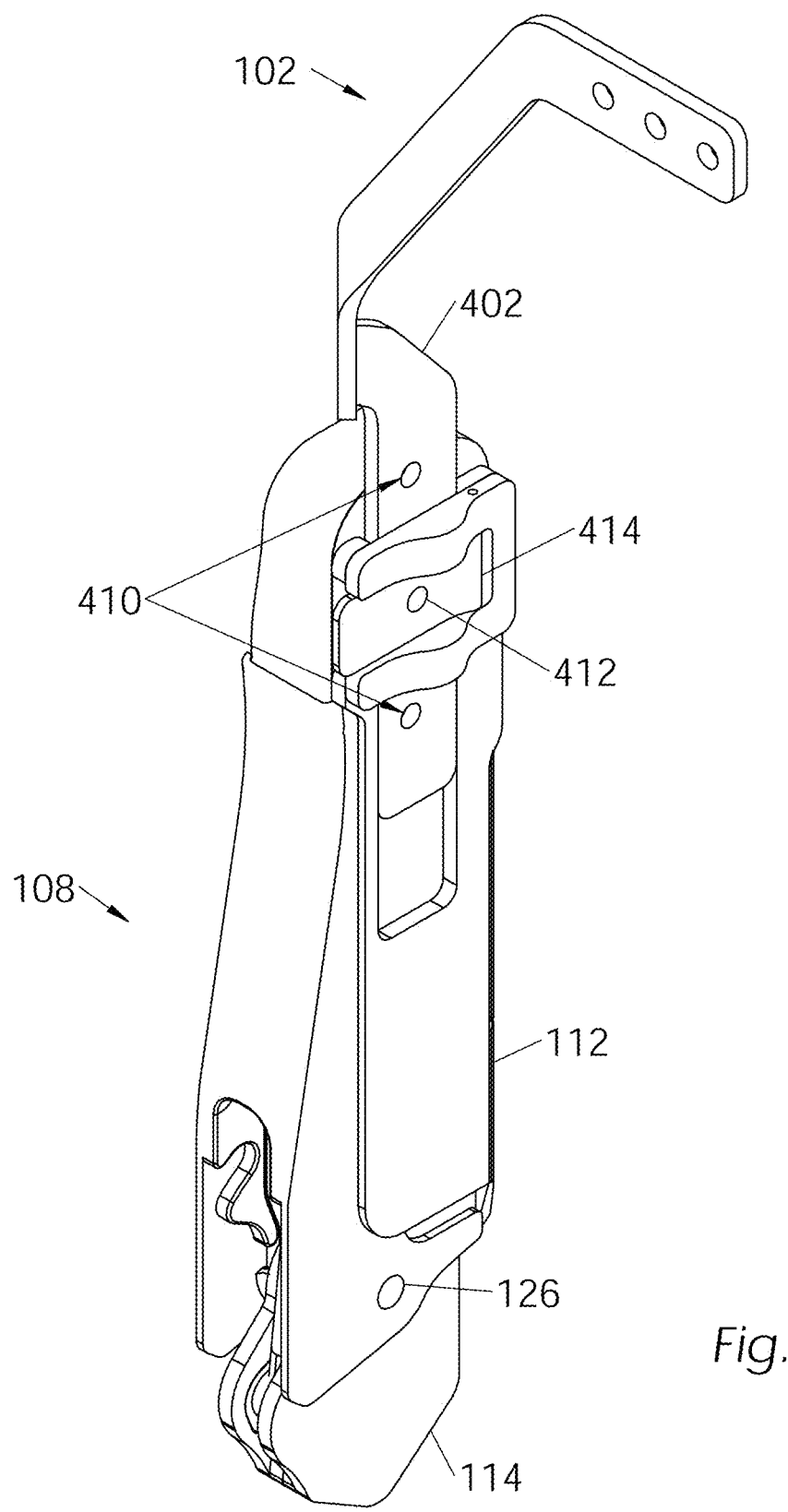
FIG. 15 depicts an embodiment of the adjustment of supporting trunk.
Figure 16:
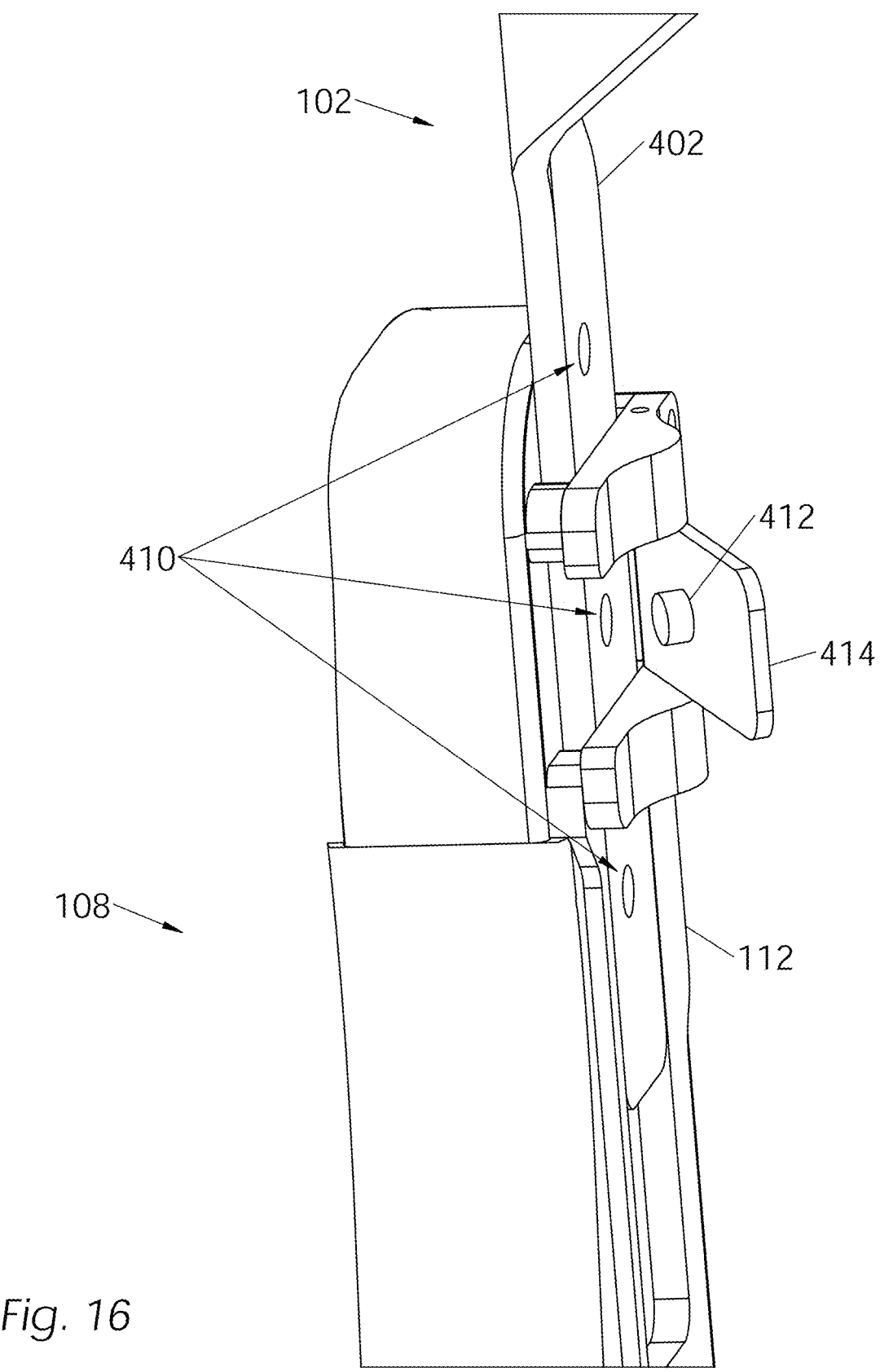
FIG. 16 depicts an embodiment of the adjustment of supporting trunk.

FIG. 13 shows an embodiment of supporting trunk 102. In this embodiment, supporting trunk 102 comprises first and second side brackets 402 and 404 which are coupled to first and second torque generators 108 and 110. Supporting trunk 102 further comprises a chest plate 406 which is in contact with wearer 200. In particular, chest plate 406 is in contact with the front of wearer's trunk 202 in the general area of said wearer's chest 210 to impose supporting trunk force 230, as depicted in FIG. 2. In operation, when wearer 200 bends forwardly and torque generators 108 and 110 are engaged, chest plate 406 of supporting trunk 102 imposes supporting trunk force 230 against the wearer's trunk 202 and onto the wearer's chest area. As shown in the embodiment of FIG. 13, the location of two side brackets 402 and 404 can be adjusted relative to first and second torque generators 108 and 110 to hold chest plate 406 in proper position. FIG. 13 shows an embodiment where the position of side brackets 402 and 404 can be adjusted. As can be seen in FIG. 14, side bracket 402 comprises several side bracket holes 410, and torque generator 108 comprises at least one pin 412. The choice of one of the side bracket holes 410 which at least one pin 412 can be inserted assigns the location of side bracket 402 relative to torque generator 108. FIGS. 15 and 16 show in some embodiments, pin 412 is coupled to torque generator 108 through a spring loaded plate 414. Spring loaded plate 414 has two positions. In operation, when spring loaded plate 414 is in its first position, pin 412 will pass through one of the side bracket holes 410 and side bracket 402 is not free to slide. When spring loaded plate 414 is in its second position as shown in FIG. 16, pin 412 is not inserted in any side bracket hole 410 and side bracket 402 is free to slide in torque generator 108.

Figure 17:
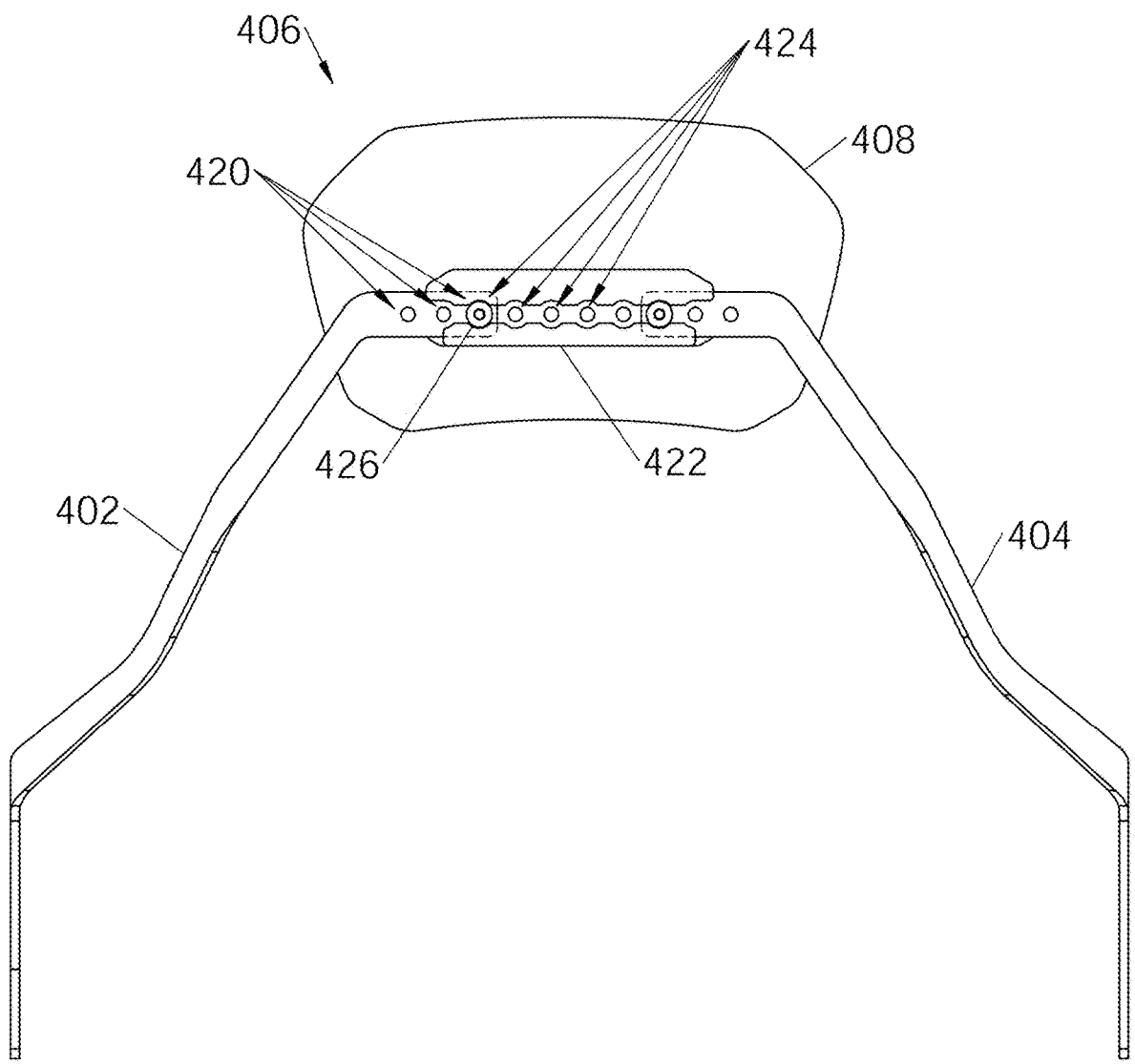
FIG. 17 depicts an embodiment of supporting trunk.

FIG. 17 shows an embodiment wherein the horizontal distance between side brackets 402 and 404 can be adjusted through adjusting the coupling locations of side brackets 402 and 404 relative to chest plate 406. In this embodiment, side bracket 402 comprises width adjustment holes 420. Chest plate 406 comprises a chest channel 422. Chest channel 422 comprises several chest plate holes 424. The connection of chest plate 406 to side bracket 402 with the help of fasteners 426 passing through width adjustment holes 420 and chest plate holes 424 results in adjustment of the width of supporting trunk 102. FIG. 17 shows an embodiment where chest plate 406 further comprises a chest pad 408. Chest pad 408 is capable of moving and rotating relative to said chest channel 422. In some embodiments, the motion and rotation of chest pad 408 relative to chest channel 422 are limited in magnitude. These rotations allow for minor movement of wearer 200 relative to chest plate 406. During operation, when wearer 200 bends supporting trunk force 230 is applied by chest plate 406 onto wearer's chest 210, as depicted in FIG. 2. It is important that supporting trunk force 230 is distributed on an area where the force distribution remains rather normal to the wearer chest. To this end, chest pad 408 has all the possible degrees of freedom relative to chest channel 422. These degrees of freedom ensure force distributions remain rather normal to the wearer's chest contour. Additionally, no rubbing forces will take place between wearer's chest 210 and chest pad 408.

Figure 21:
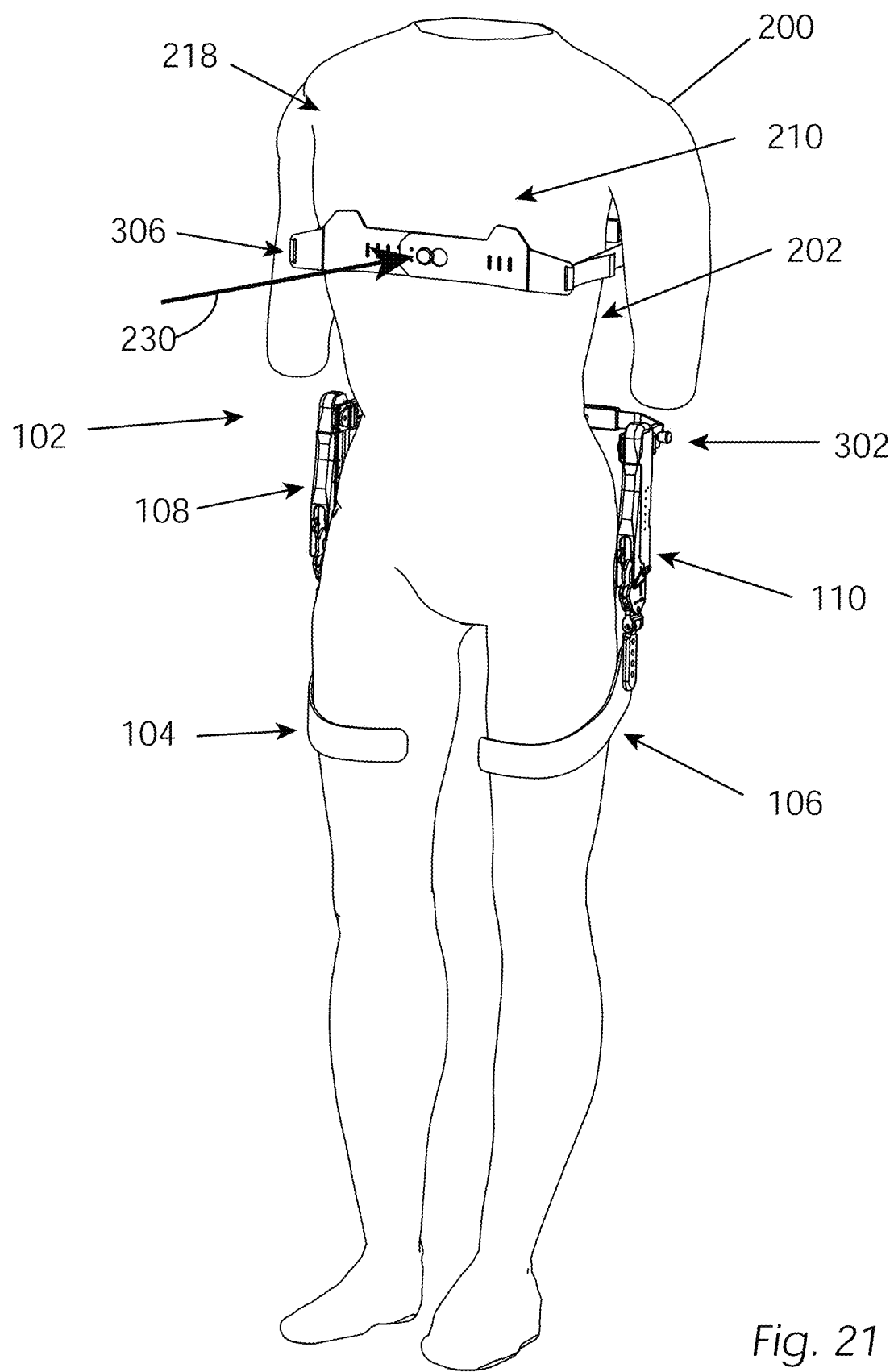
FIG. 21 depicts an anterior three-quarters view showing an embodiment of the trunk supporting exoskeleton worn by a wearer.
Figure 22:
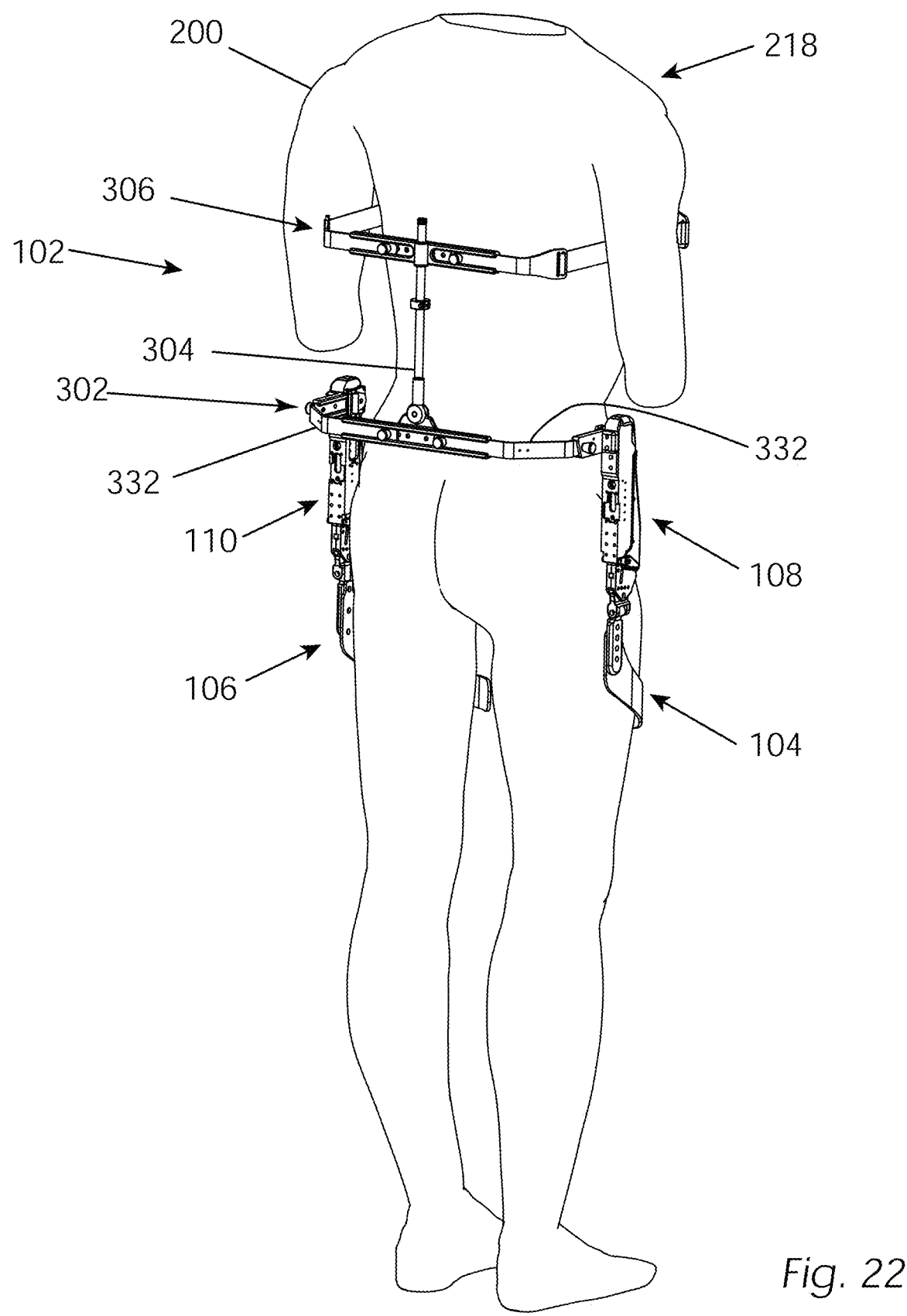
FIG. 22 depicts a posterior three-quarters view showing the trunk supporting exoskeleton in FIG. 21 worn by a wearer.
Figure 23:
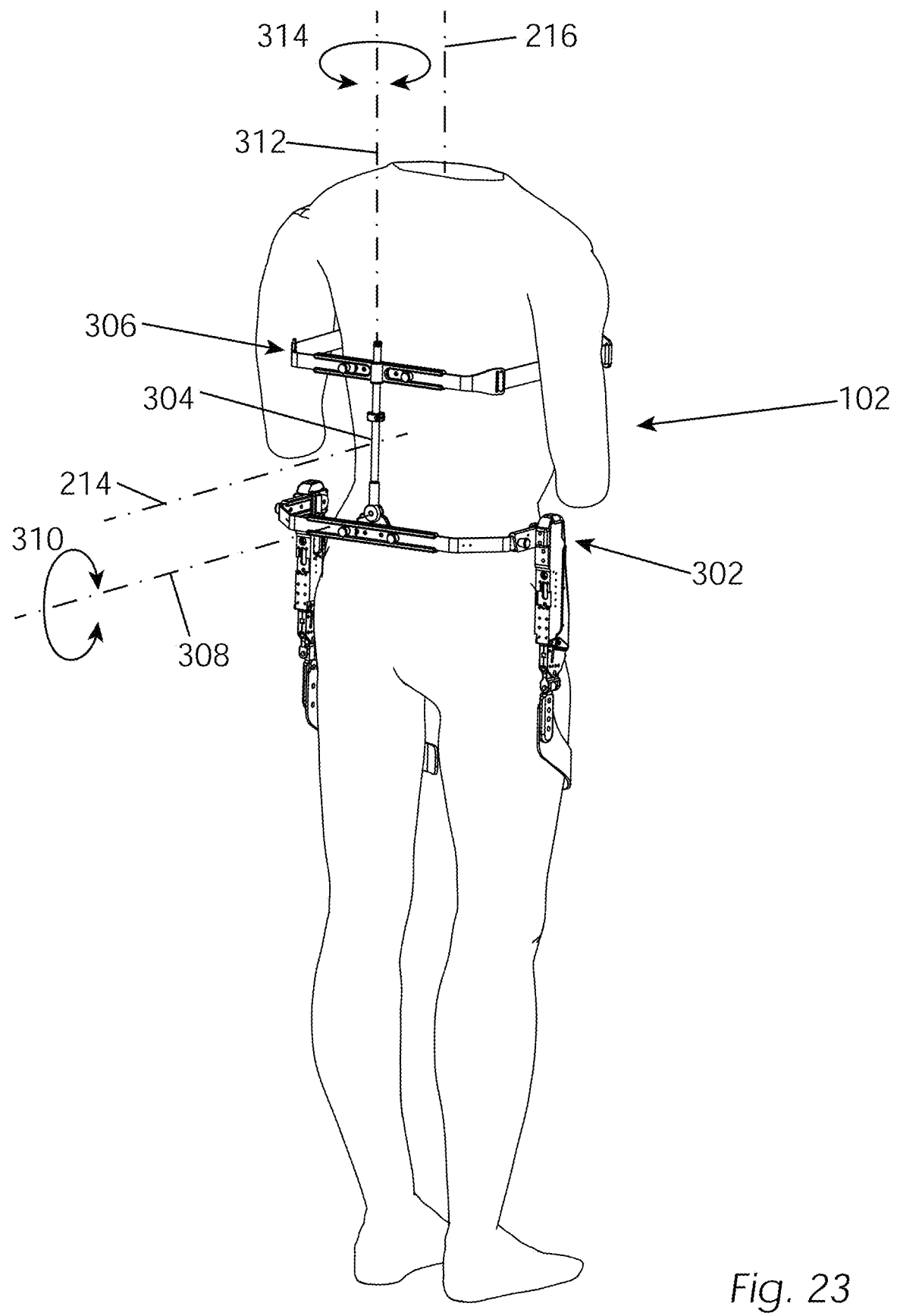
FIG. 23 depicts a posterior three-quarters view showing an embodiment of the trunk supporting exoskeleton with spine rotation capabilities being worn by a wearer.

FIGS. 21 and 22 show two views of another embodiment of supporting trunk 102 worn by wearer 200. Supporting trunk 102 comprises a lower frame 302 which is substantially located behind wearer 200. Lower frame 302 is configured to partially surround wearer's trunk 202 and is coupled to first and second torque generators 108 and 110 from two sides of wearer 200. Supporting trunk 102 further comprises a spine frame 304 which is located behind wearer 200, as depicted in FIG. 22. Spine frame 304, in some embodiments, is rotatably coupled to lower frame 302. Supporting trunk 102 additionally comprises an upper frame 306 which is coupled to spine frame 304. In some embodiments, upper frame 306 is configured to be in contact with the general area of wearer's trunk 202 to impose force 230 on front part of wearer's trunk 202. In some embodiments, upper frame 306 is in contact with the general chest area 210 of wearer's trunk 202 to impose force 230. In some embodiments, upper frame 306 is in contact with the general shoulder area 218 of wearer's trunk 202 to impose force 230. Spine frame 304 in some embodiments rotates relative to lower frame 302 along an axis substantially parallel to one of the wearer's lumbar spine mediolateral flexion and extension axes 214. As shown in FIG. 23, spine frame 304 rotates about axis 308 with respect to lower frame 302. Axis 308 is substantially parallel to one of the wearer's lumbar spine mediolateral flexion and extension axes 214. Arrow 310 shows the direction of rotation of spine frame 304 relative to lower frame 302 about axis 308. In some embodiments, spine frame 304 rotates relative to lower frame 302 along an axis 312 substantially parallel to wearer's cranial-caudal axis 216. Arrow 314 shows the direction of this rotation about axis 312.

Figure 24:
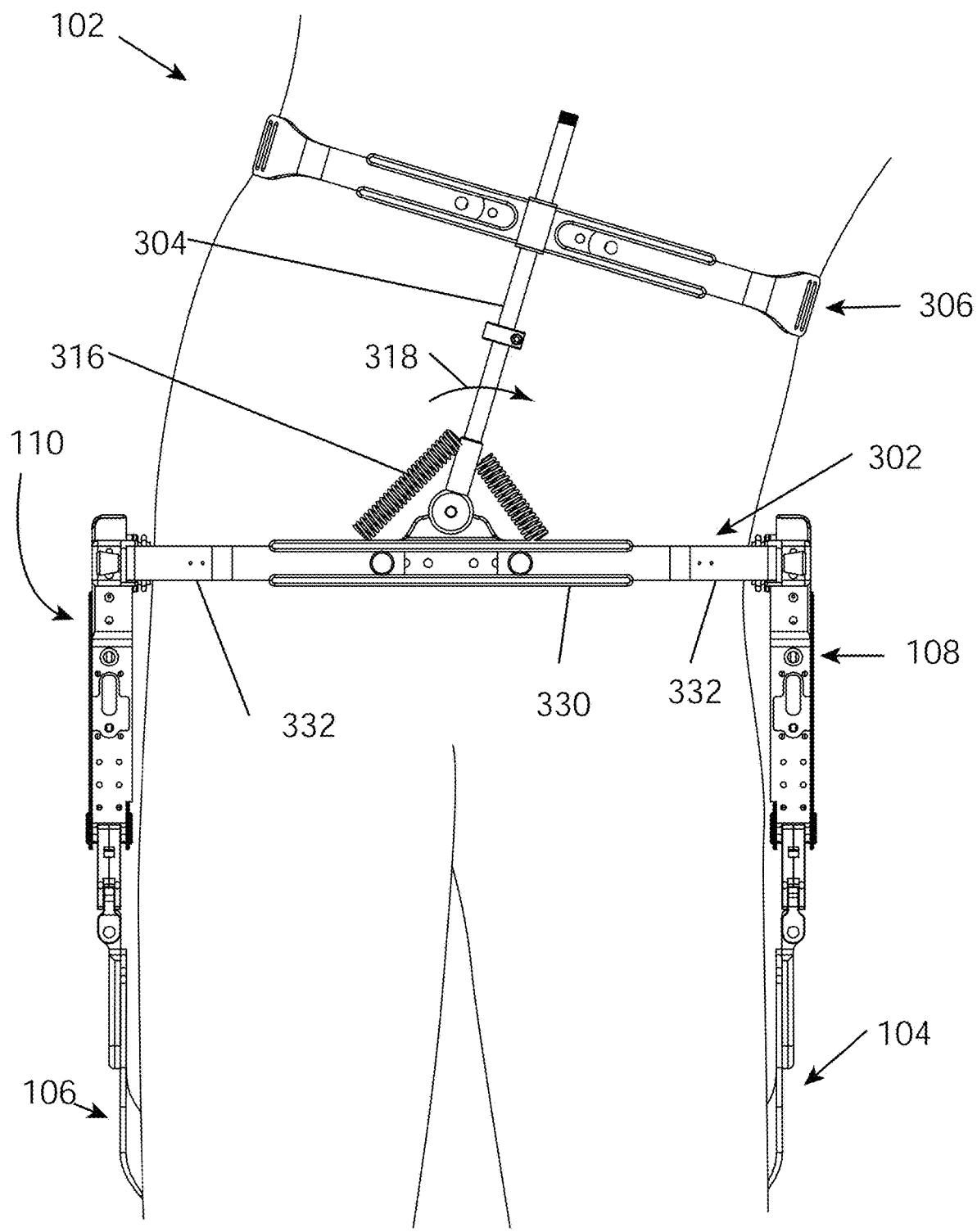
FIG. 24 depicts a posterior view showing the trunk supporting exoskeleton of FIG. 23 worn by a wearer with resistive elements to resist lateral spine rotation.
Figure 25:
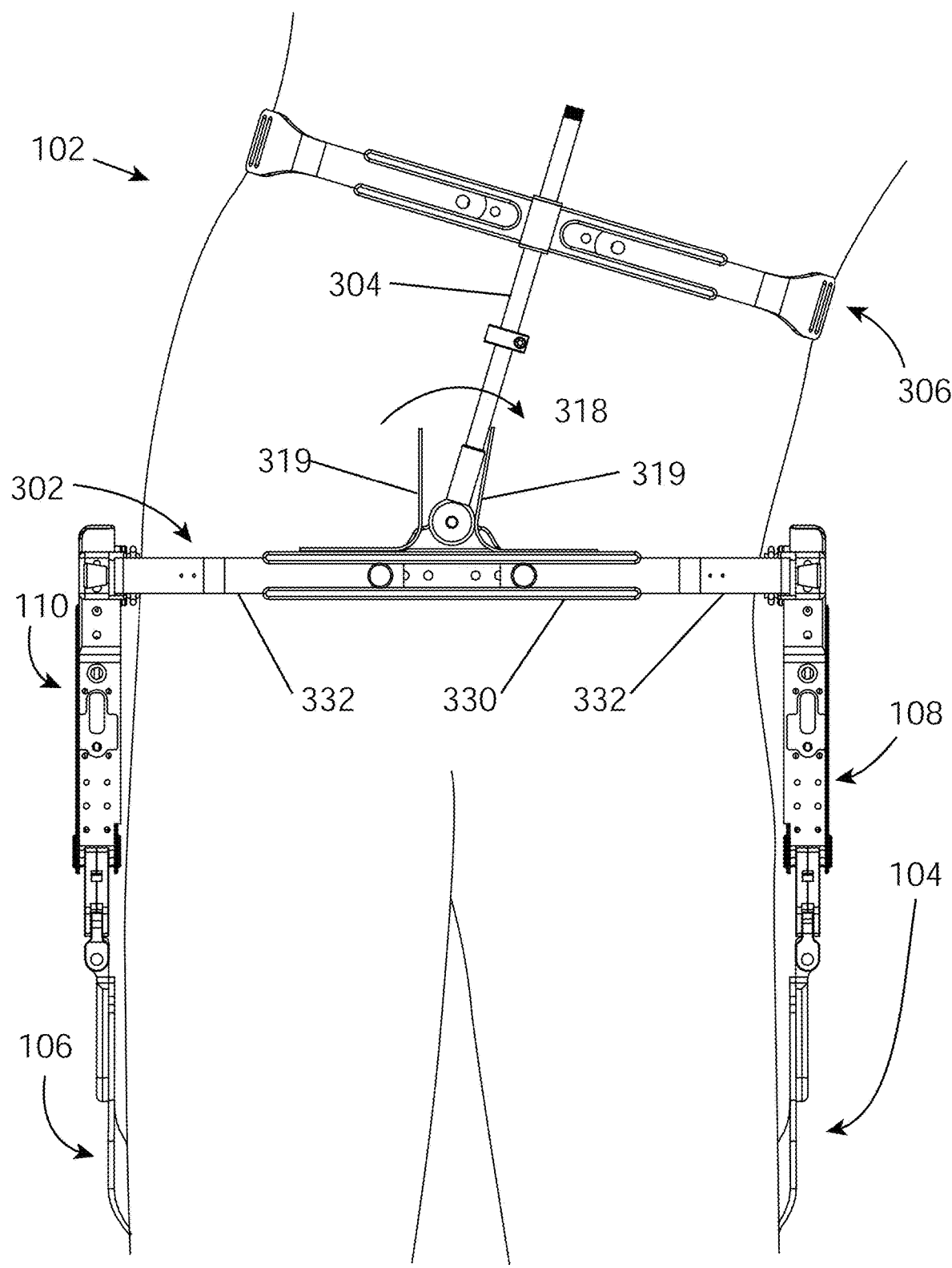
FIG. 25 depicts a posterior view showing the embodiment of FIG. 24 being worn by a wearer wherein the resistive elements are leaf springs.
Figure 26:
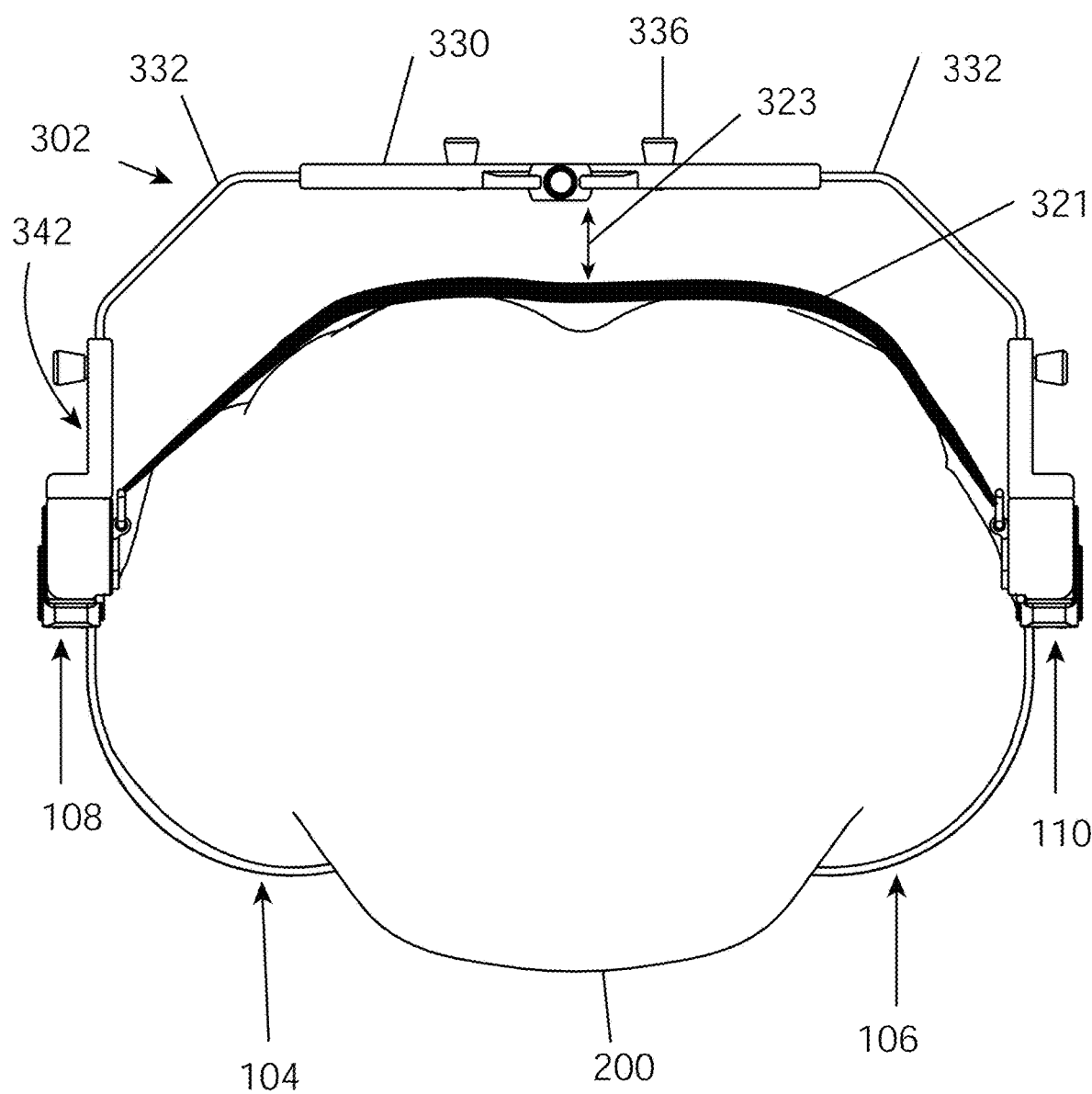
FIG. 26 depicts a top-down view at waist height showing an embodiment of the trunk supporting exoskeleton worn by a wearer, with a suspension harness coupled to the torque generators.
Figure 27:
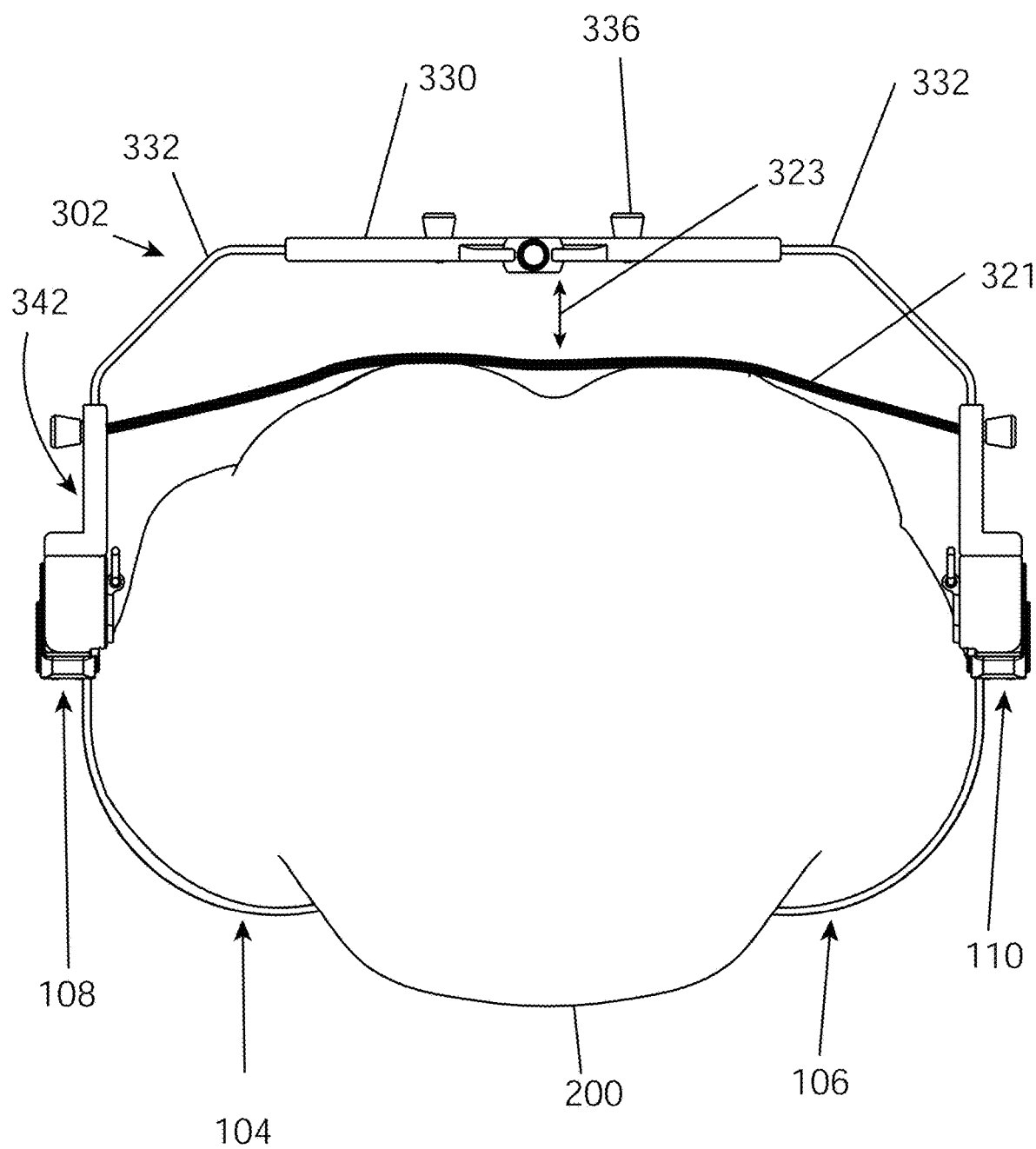
FIG. 27 depicts a top-down view at waist height showing the embodiment of FIG. 27 worn by a wearer, wherein the suspension harness is coupled to the lower frame.

FIG. 24 shows an embodiment where supporting trunk 102 further comprises at least one resisting element 316 to provide resistance against the rotational motion 318 of spine frame 304 relative to lower frame 302. In some embodiments, resisting element 316 is selected from a group consisting of gas springs, leaf springs, tensile springs, compression springs, and combinations thereof. FIG. 25 shows an embodiment where the resisting element are leaf springs 319. In some embodiments, as shown in FIG. 25, resisting elements 319 do not resist the rotational motion for a limited range of motion of spine frame 304 relative to lower frame 302. FIG. 26 shows a top view of an embodiment wherein lower frame 302 comprises a suspension harness 321. Suspension harness 321 is coupled to trunk support exoskeleton 100 on each side of wearer 200. Suspension harness 321 is configured in such a manner to provide a distance 323 between wearer 200 and lower frame 302 to prevent contact between wearer 200 and lower frame 302. As can be seen in FIG. 26, in some embodiments, suspension harness 321 is coupled to torque generators 108 and 110. As can be seen in FIG. 27, in some embodiments, suspension harness 321 is coupled to lower frame 302.

Figure 28:
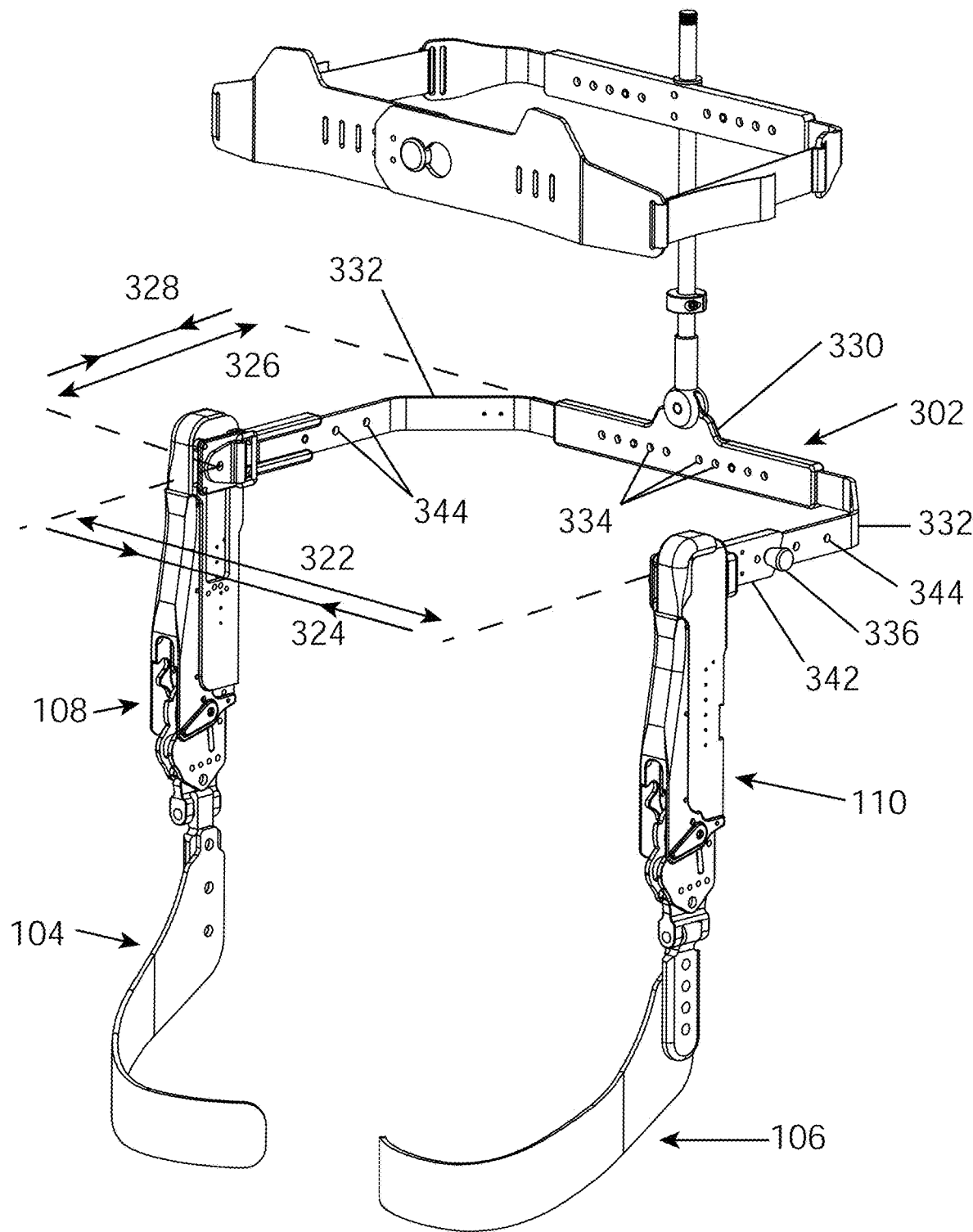
FIG. 28 depicts an anterior three-quarters view showing the trunk supporting exoskeleton of FIG. 21 with the wearer's body removed for clarity.

FIG. 28 shows an embodiment wherein lower frame 302 is adjustable in width to fit various people. Arrows 322 and 324 indicate directions of increasing and decreasing width, respectively. In some embodiments, the lower frame 302 is adjustable in depth to fit various people. Arrows 326 and 328 indicate directions of increasing and decreasing depth, respectively. In some embodiments as shown in NG. 28, lower frame 302 comprises a lower middle bar 330 and two lower corner bars 332. Lower corner bars 332 can be coupled to lower middle bar 330 at various locations 334 on lower middle bar 330 to provide desirable width adjustment for lower frame 302 to fit various people.

Figure 29:
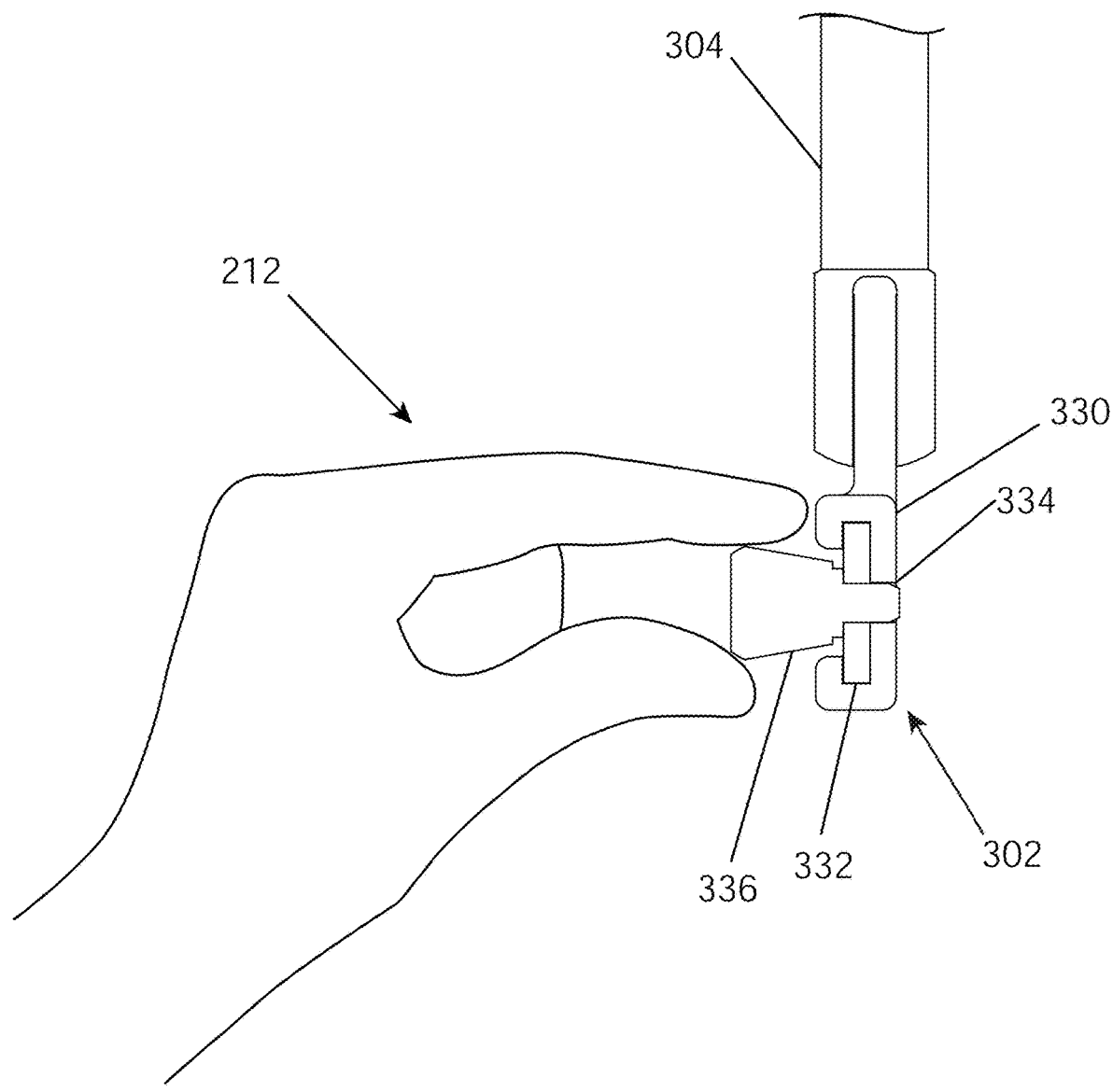
FIG. 29 depicts a cross-sectional view showing an embodiment of the lower frame where lower corner bars are locked by retractable pins.
Figure 30:
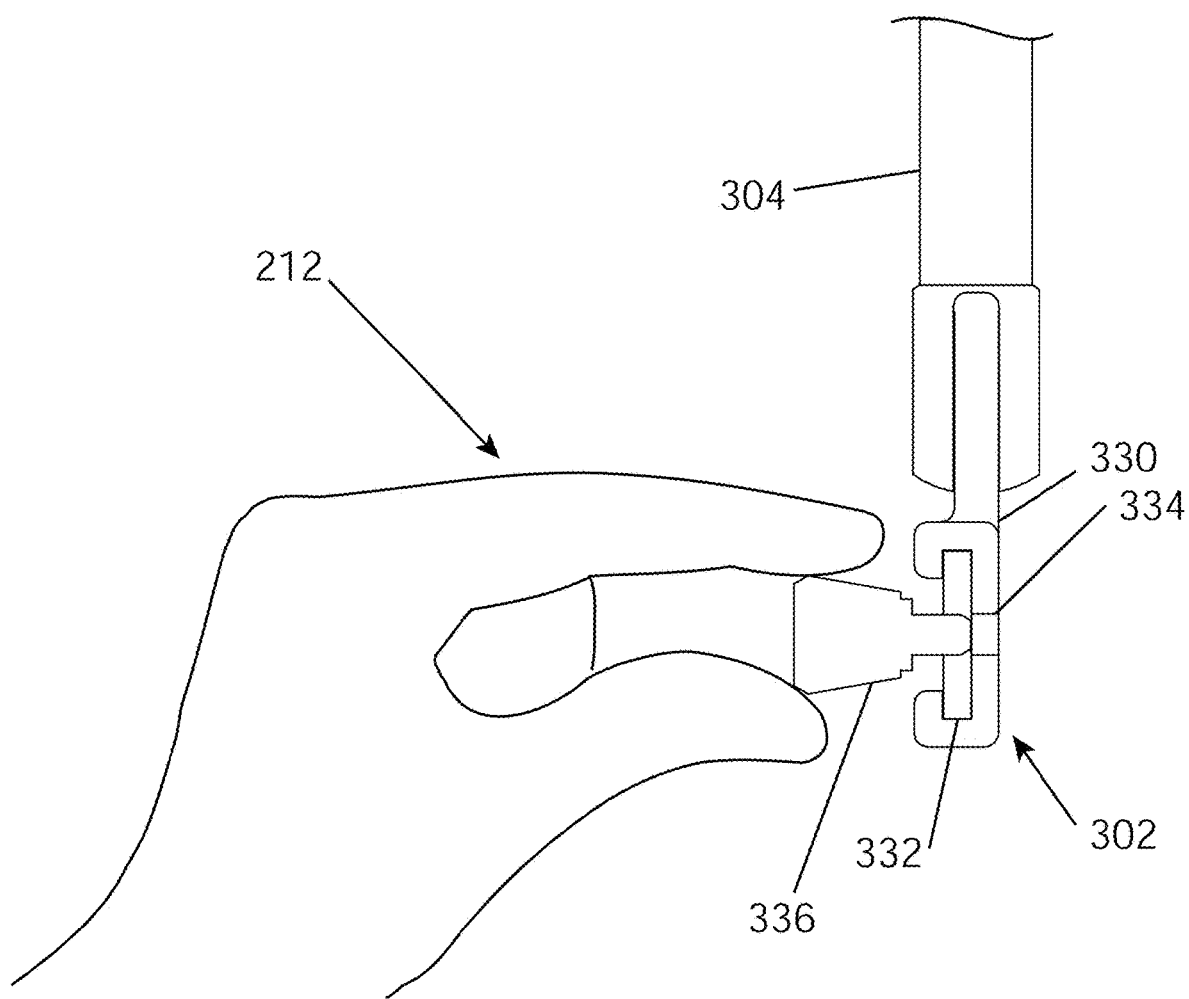
FIG. 30 depicts the embodiment of FIG. 29 where retractable pins have been retracted and lower corner bars are free to slide.

FIGS. 28 and 29 show a cross section of an embodiment of lower frame 302 where hand-retractable pins 336 are used to couple lower corner bars 332 to lower middle bar 330 at various locations 334. As can be seen in FIG. 29, lower middle bar 330 has a channel cross section and corner bars have rectangular cross sections to provide the sliding motion along arrows 322 and 324 for adjustment. FIG. 29 shows the configuration wherein retractable pin 336 is inserted in lower frame 302. FIG. 30 shows that the retractable pin 336 is retracted from location 334, thus lower corner bars 332 are free to slide within lower middle bar 330.

Figure 31:
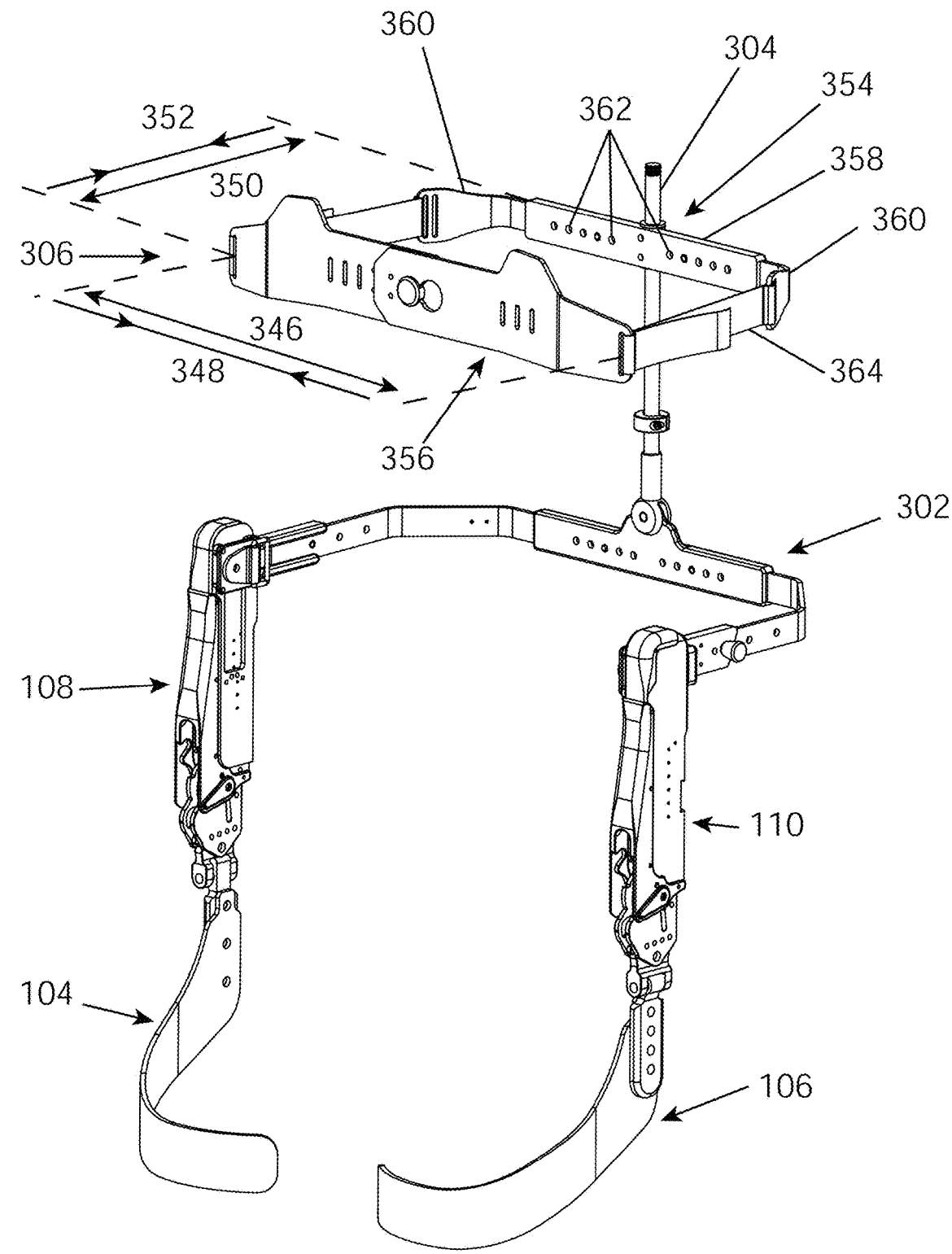
FIG. 31 depicts the trunk supporting exoskeleton of FIG. 28 illustrating upper frame adjustment capability.

In some embodiments, as illustrated in FIG. 28, lower frame 302 further comprises two opposing side brackets 342. Each side bracket 342 can be coupled to the rest of lower frame 302 at various locations 344 on lower frame 302 to provide desirable depth adjustment for lower frame 302 to fit various people. In some embodiments, similar to adjustment procedure for width of lower frame, hand-retractable pins 336 have been used to couple respective side bracket 342 to lower frame 302 at various locations 344. FIG. 31 shows an embodiment wherein upper frame 306 of supporting trunk 102 is adjustable in width to fit various people. Arrows 346 and 348 indicate directions of increasing and decreasing width, respectively. In some embodiments, upper frame 306 of supporting trunk 102 is adjustable in depth to fit various people. Arrows 350 and 352 indicate directions of increasing and decreasing depth, respectively.

Figure 32:
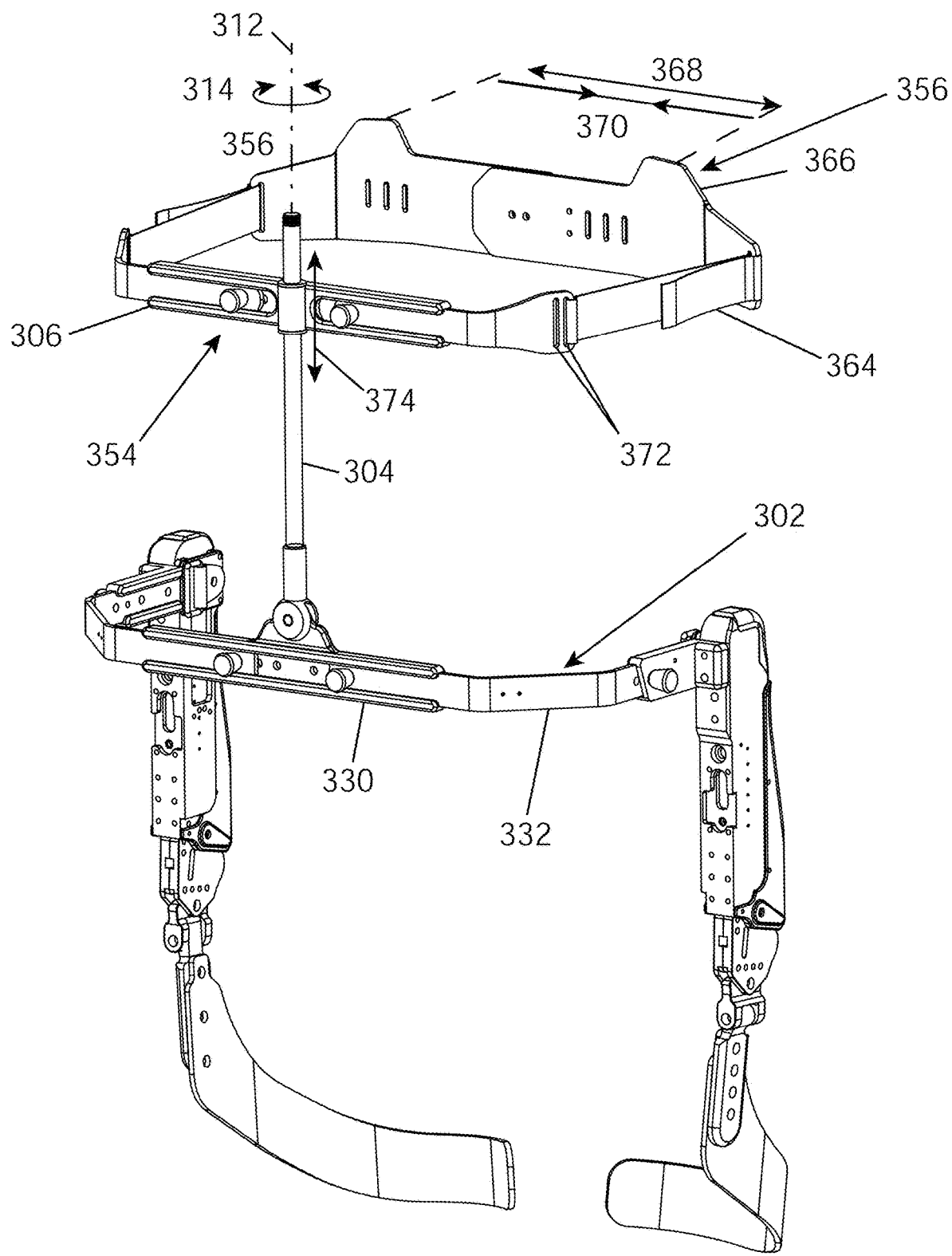
FIG. 32 depicts a posterior three-quarters view of the trunk supporting exoskeleton in FIG. 28 illustrating upper front frame adjustment capability.

Upper frame 306 comprises an upper rear frame 354 coupled to spine frame 304. Upper frame 306 further comprises an upper front frame 356 coupled to upper rear frame 354. Upper front frame 356 is configured to be in contact with the front of said wearer's trunk 202 such as general area of chest 210 and shoulder 218, as depicted in FIG. 21, for example. In some embodiments as shown in FIG. 31, upper rear frame 354 comprises an upper middle bar 358 and two upper corner bars 360. Upper corner bars 360 can be coupled to upper middle bar 358 at various locations 362 on upper middle bar 358 to provide desirable width adjustment for upper frame 306 to fit various people. In some embodiments, as shown in FIG. 32, similar to adjustment procedure for width of lower frame 302, hand-retractable pins 336 have been used to couple upper corner bars 360 to upper middle bar 358 at various locations 362. In some embodiments as shown in FIG. 32, upper front frame 356 comprises two connecting members 364 which are coupled to upper rear frame 354. Upper front frame 356 further comprises at least one chest plate 366 coupled to connecting members 364. At least one chest plate 366 is in contact with the front of said wearer's trunk such as the general area of chest 210 and shoulder 218. Connecting members 364 can be selected from a group consisting of rigid members, semi-rigid members, straps, adjustable-length strap loops and combinations thereof.

Figure 33:
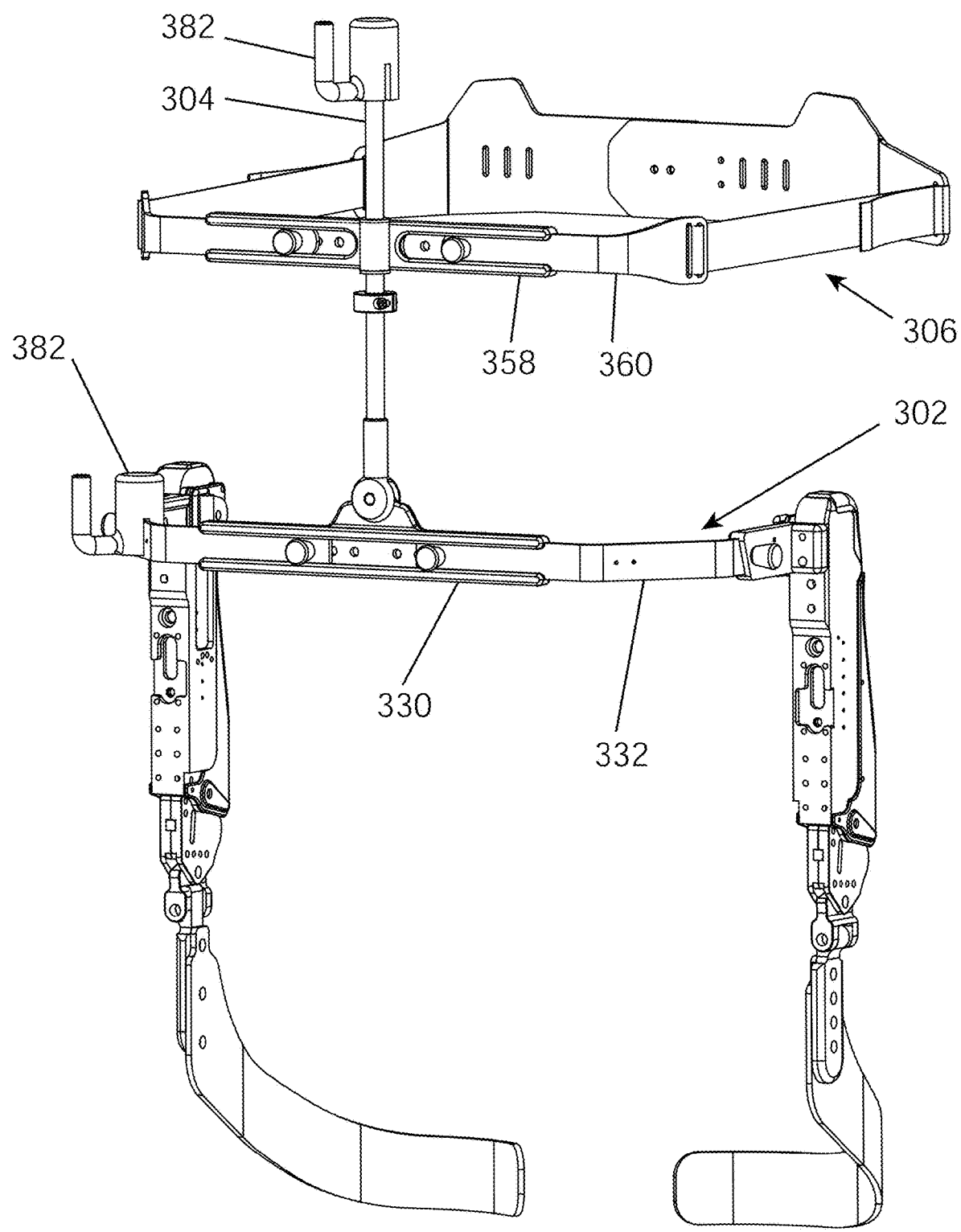
FIG. 33 depicts a posterior three-quarters view of the trunk supporting exoskeleton in FIG. 28 with external objects coupled to the spine frame and lower frame.
Figure 34:
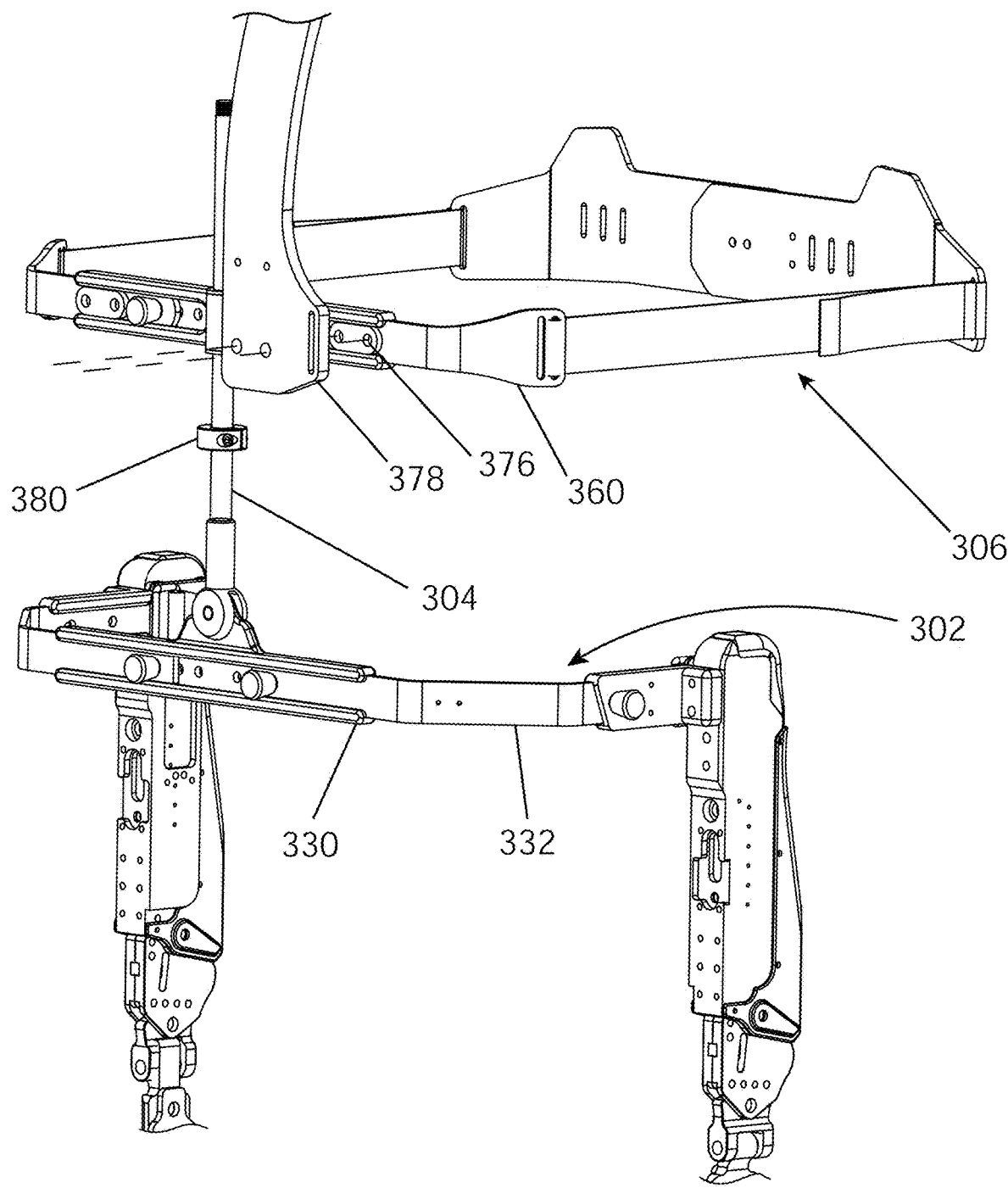
FIG. 34 depicts a posterior three-quarters view of an embodiment of the trunk supporting exoskeleton illustrating attachment of an external object to the upper frame.

FIG. 32 shows an embodiment in which the width of upper front frame 356 is adjustable to fit various people. Arrows 368 and 370 indicate directions of increasing and decreasing width, respectively. As shown in FIG. 32, in some embodiments, connecting members 364 can be coupled to the rest of upper rear frame 354 at various locations 372 to provide desirable depth adjustment for upper frame 306 to fit various people. In the embodiment of FIG. 32, various locations 32 are formed as slots to accommodate connecting elements 364 (e.g. straps). In some embodiments, upper frame 306 is configured to slide linearly along spine frame 304. Arrow 374 in FIG. 32 indicates directions of linear sliding motion along spine frame 304. In some embodiments, as shown in FIG. 32, upper frame 306 is configured to rotate on spine frame 304 along the major axis 312 of spine frame 304. Arrow 314 indicates this rotation. In some embodiments, trunk supporting exoskeleton 100 can also be employed to carry external objects. In some embodiments, external object holders 382 such as carrying hooks, as shown in FIG. 33, can be mounted on trunk supporting exoskeleton 100 to couple external objects to trunk supporting exoskeleton 100. External object holder 382, as shown in FIG. 33, can be mounted on spine frame 304. External object holder 382 can also be mounted on lower frame 302, also shown in FIG. 33. External objects could be backpack, boxes and other heavy objects. FIG. 34 shows an exploded view of an embodiment in which an external object 378 can directly be coupled to upper frame 306. In this situation, trunk supporting exoskeleton 100 further comprises a locking element 380 that restricts the sliding movement of upper frame 306 along spine frame 304. FIG. 34 shows an embodiment of upper frame 306 wherein upper corner bars 360 have several coupling features such as threaded holes 376 for coupling external object 378 to upper frame 306.

Figure 35:
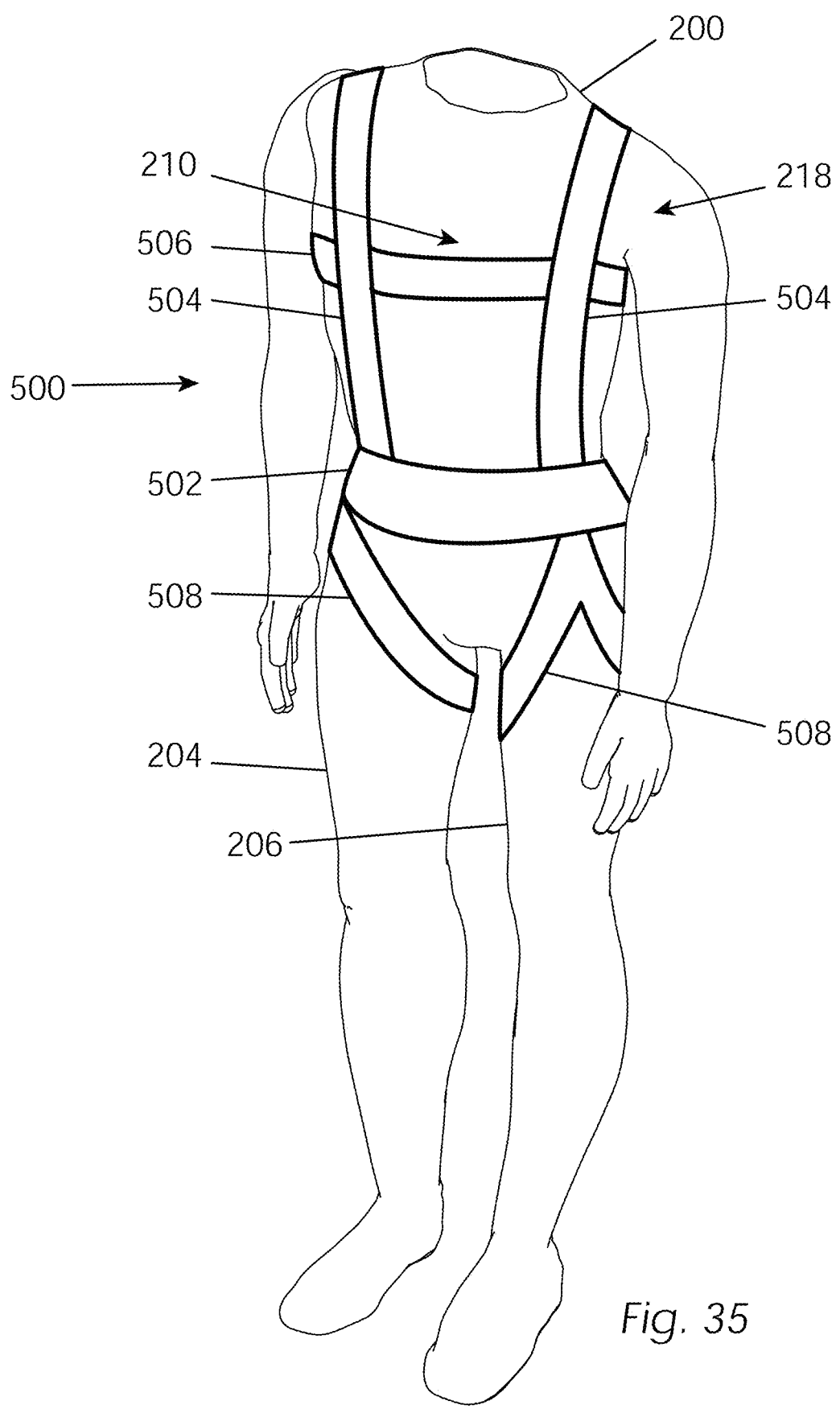
FIG. 35 depicts an anterior three-quarters view of the human machine interface worn by a wearer.
Figure 36:
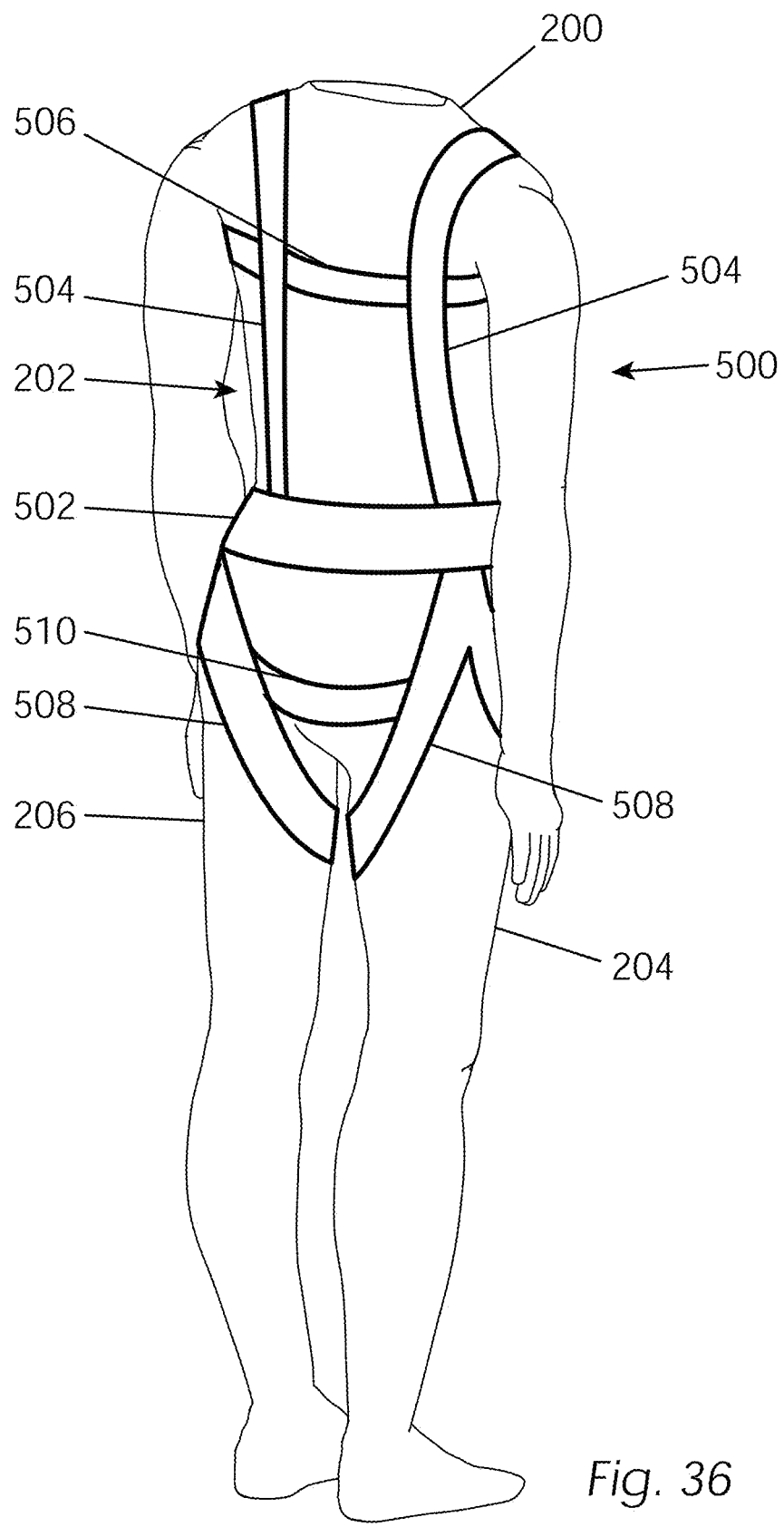
FIG. 36 depicts a posterior three-quarters view of the human machine interface and wearer of FIG. 35.

Trunk supporting exoskeleton 100 can be coupled to a human interface system 500 which is configured to be worn by wearer 200, as depicted in FIG. 35 and FIG. 36. In some embodiments, as shown in FIG. 35 and FIG. 36, human interface system 500 comprises a waist belt 502 which is worn on wearer's waist. In some embodiments, human interface system 500 comprises two shoulder straps 504 worn on shoulders of wearer 200. In some embodiments, human interface system 500 comprises a chest strap 506 worn on the chest of wearer 200. In some embodiments, human interface system 500 comprises two thigh straps 508 which are worn around the thighs of wearer 200. In some embodiments, human interface system 500 comprises a bridge strap 510 connecting two thigh straps 508 behind wearer 200. In some embodiments, human interface system is selected from a group comprising of safety harness, safety belt, tool belt harness, tool belt, climbing harness, construction worker fall protection safety harness and any combination thereof. The advantage of using a safety harness, a safety belt, a climbing harness, or a construction worker fall protection safety harness as human interface system 500 is that two functions are achieved simultaneously: securing safety of wearer 200, and coupling trunk supporting exoskeleton 100 to wearer 200.

In general, human interface system 500 is intended to couple trunk supporting exoskeleton 100 to wearer 200. In some embodiments, human interface system 500 comprises an element or a combination of elements selected from the group consisting of a waist belt 502 worn on the waist of said wearer, two shoulder straps 504 worn on the shoulders of wearer 200, two thigh straps 508 worn around the thighs of wearer 200, bridge strap 510 connecting two thigh straps 508, chest strap 506 and any combination thereof. Depending on the intended use, one of ordinary skill in the art can design human interface system 500 to comprise any element worn by a wearer of an exoskeleton, including but not limited to the elements described above, as for example, work overalls or other type of garment. These elements can be used, either individually or in combination, to couple trunk supporting exoskeleton 100 to wearer 200.

Figure 65:
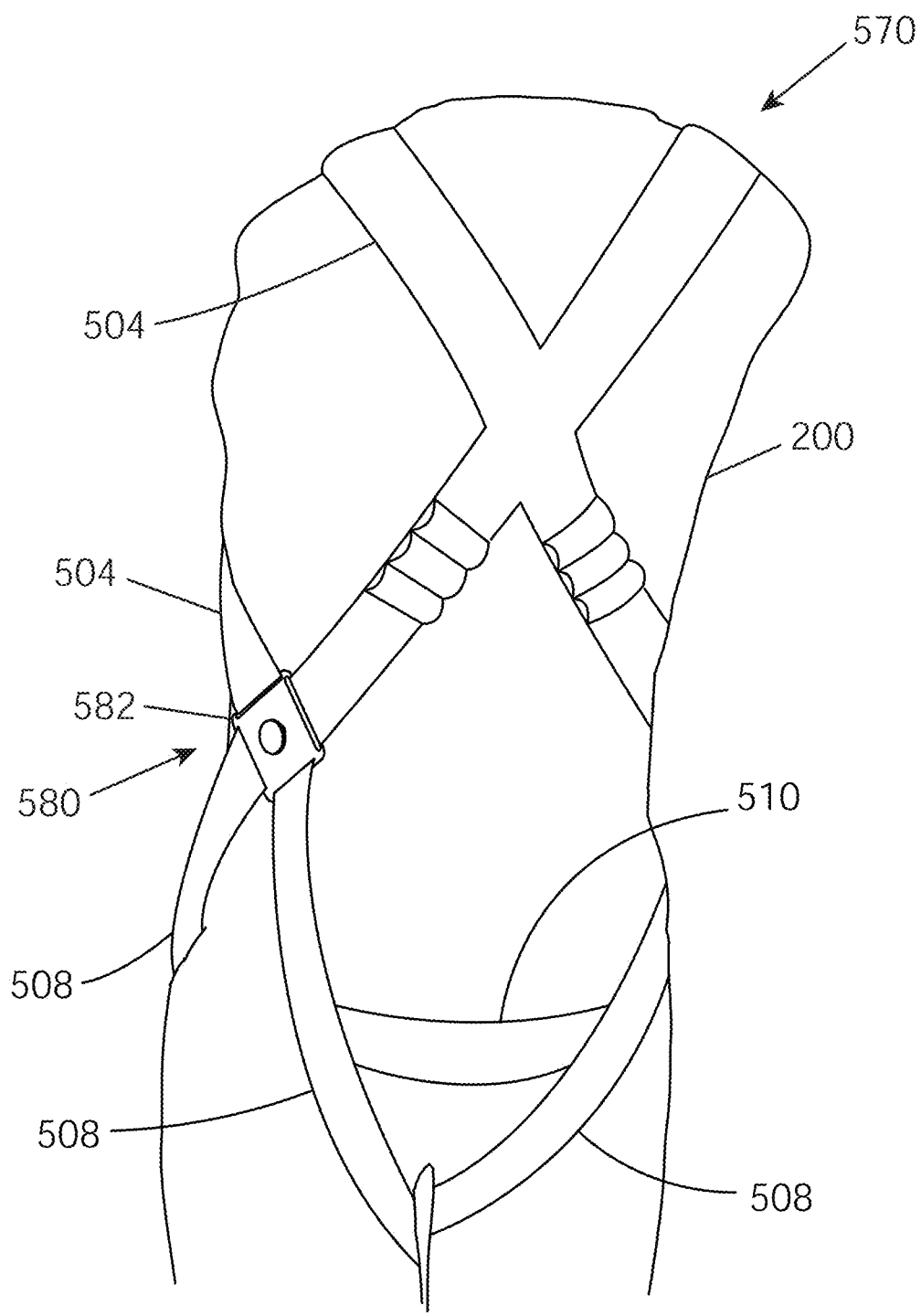

In some embodiments, human interface system 500 comprises belt 502 (such as a safety belt or tool belt) as shown, for example, in FIGS. 46-55. In other embodiments, safety harnesses used by workers in various environments may be deployed as human interface system 500. In some embodiments, as shown in FIG. 65, human interface system 500 comprises fall protection safety harness 570. In general, one of ordinary skill in the art will recognize that human interface system 500 can comprise any safety harness, such as, for example, a climbing harness or fall prevention safety harness, or any combination of safety harnesses capable of performing the indicated function of coupling trunk supporting an exoskeleton to a wearer, in addition to securing safety for the wearer. Thus, in some embodiments, human interface system 500 is selected from the group consisting of a safety harness, a safety belt, a construction worker fall protection safety harness, a climbing harness, a fall prevention safety harness, a tool belt, and any combination thereof.

In general, there are various methods of coupling trunk supporting exoskeleton 100 to human interface system 500. The important issue is to ensure trunk supporting exoskeleton 100 is coupled to human interface system 500 such that trunk supporting exoskeleton 100 robustly stays on wearer 200 during all kinds of maneuvers. In some embodiments, torque generators 108 and 110 are configured to be coupled to human interface system 500. In some embodiments, supporting trunk 102 is configured to be coupled to human interface system 500. In some embodiments, torque generators 108 and 110 are configured to be coupled to waist belt 502. In some embodiments, supporting trunk 102 is configured to be coupled to waist belt 502. In some embodiments, supporting trunk 102 is configured to be coupled to chest strap 506. In some embodiments, supporting trunk 102 is configured to be coupled to shoulder straps 504. The coupling in all embodiments described above can take place through the use of VELCRO®, buttons, lace, sewing, glue, buckles, and other coupling mechanisms. In fact, in some embodiments, trunk supporting exoskeleton 100 is configured to be coupled to human interface system 500 through the use of a release mechanism 530 depicted in FIG. 37, for example. This is especially useful when trunk support exoskeleton 100 is used with a fall protection safety harness 570 shown in FIG. 40. The trunk support exoskeleton 100 can be coupled to fall protection safety, harness 570 through release mechanism 530 described below.

Figure 37:
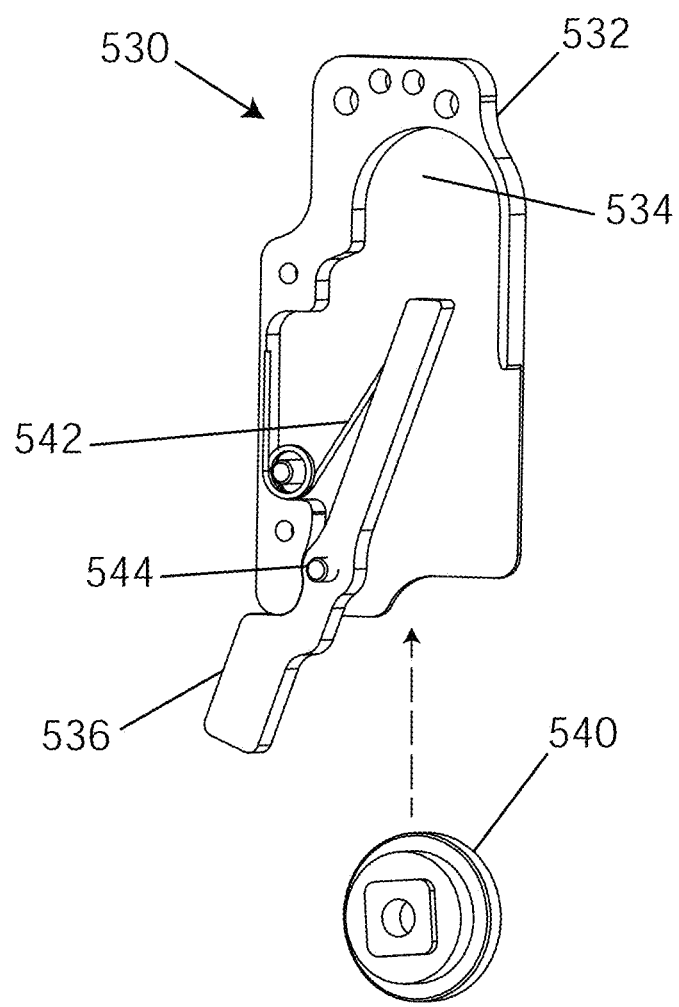
FIG. 37 depicts an embodiment of release mechanism.
Figure 38:
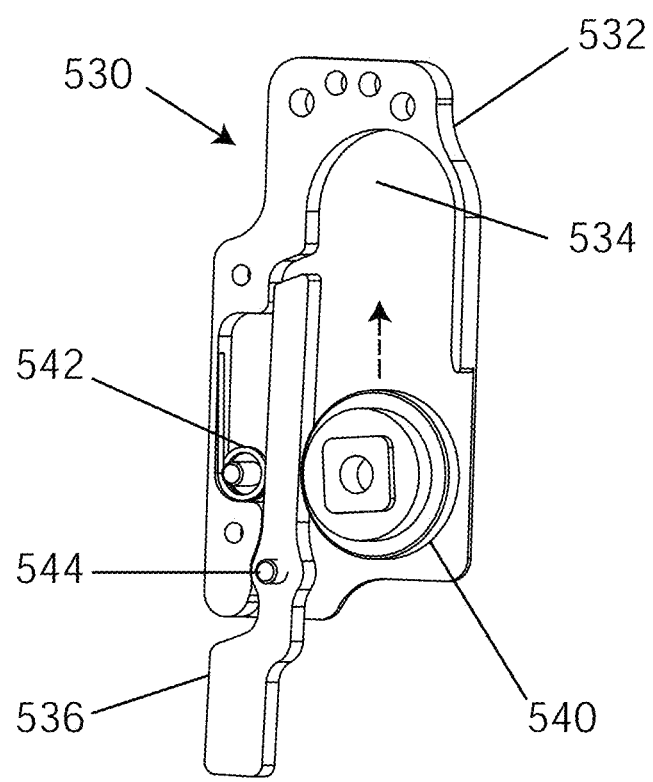
FIG. 38 depicts an embodiment of release mechanism.
Figure 39:
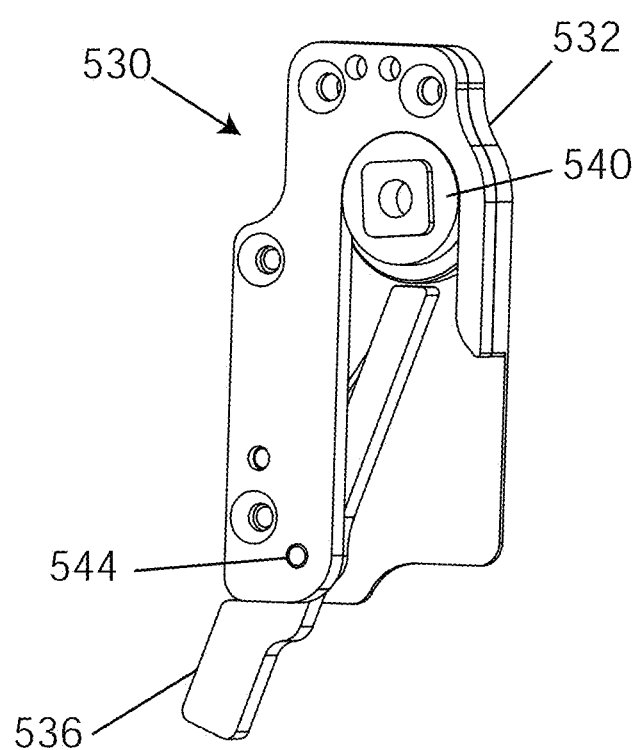
FIG. 39 depicts an embodiment of release mechanism.

FIG. 37 shows an embodiment of the release mechanism 530 which is used to couple torque generator 108 or supporting trunk 102 to waist belt 502. Release mechanism 530 comprises a holding bracket 532 and a button 540. Holding bracket 532 comprises a cavity 534 formed within holding bracket 532. Holding bracket 532 further comprises an unlocking lever 536, rotatable about a joint 544. Unlocking lever 536 has two positions: locked position and unlocked position. FIG. 38 shows release mechanism 530 where unlocking lever 536 is in unlocked position and button 540 is moving toward cavity 534. FIG. 39 shows release mechanism 530 where button 540 has moved to its final destination and unlocking lever 536 is in locked position. In some embodiments, unlocking lever 536 is spring loaded relative to holding bracket 532. This causes the unlocking level positions itself to locked position. FIG. 37 shows an embodiment where torsional spring 542 brings unlocking lever 536 to its locked position. In operation when button 540 has been placed in cavity 534, button 540 cannot be removed if unlocking lever 536 is in its locked position. However, button 540 is free to be removed from cavity 534 if unlocking lever 536 is in its unlocked position. In some embodiments, button 540 is coupled to waist belt 502 and holding bracket 532 is coupled to trunk supporting exoskeleton 100. In some embodiments, holding bracket 532 is coupled to waist belt 502 and button 540 is coupled to trunk supporting exoskeleton 100. In some embodiments, button 540 is coupled to waist belt 502 and holding bracket 532 is coupled to torque generator 108. In some embodiments, holding bracket 532 is coupled to waist belt 502 and button 540 is coupled to torque generator 108. In some embodiments, button 540 is coupled to waist belt 502 and holding bracket 532 is coupled to supporting trunk 102. In some embodiments, holding bracket 532 is coupled to waist belt 502 and button 540 is coupled to supporting trunk 102.

Figure 19:
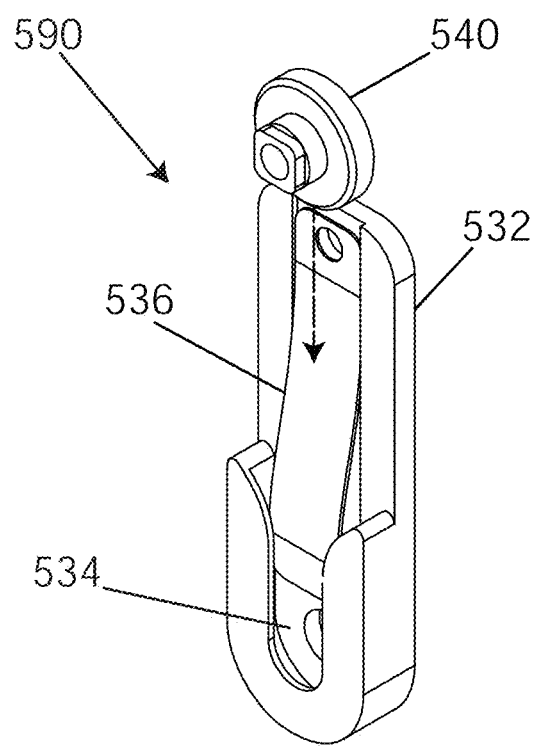
FIG. 19 depicts an embodiment of a release mechanism.
Figure 20:
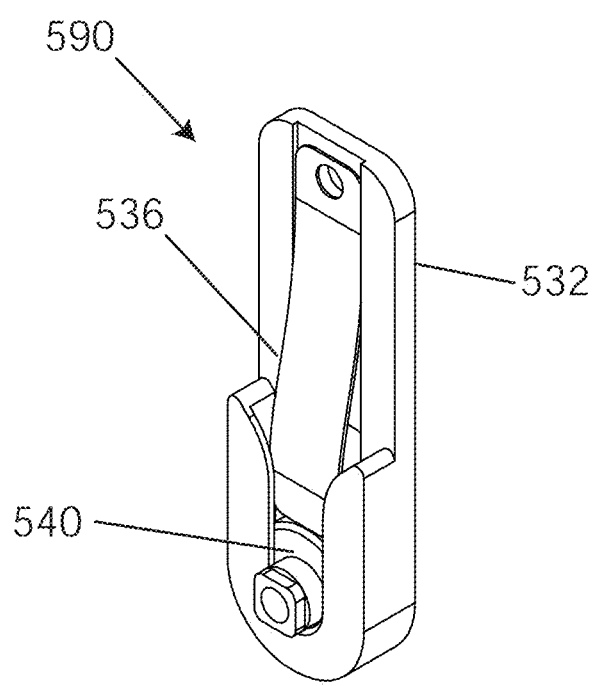
FIG. 20 depicts an embodiment of a release mechanism.

FIG. 19 shows another embodiment of the quick release mechanism 590 which is used to couple torque generator 108 or supporting trunk 102 to waist belt 502. Quick release mechanism 590 comprises a holding bracket 532 and a button 540. Holding bracket 532 comprises a cavity 534 formed within holding bracket 532. Holding bracket 532 further comprises an unlocking lever 536. Unlocking lever 536 has two positions: locked position and unlocked position. FIG. 19 shows quick release mechanism 590 where button 540 is moving toward cavity 534. FIG. 20 shows quick release mechanism 590 where button 540 has moved to its final destination and unlocking lever 536 is in locked position. In this embodiment unlocking lever 536 is a leaf spring and when it is pushed button 540 can be removed from cavity 534.

Figure 40:
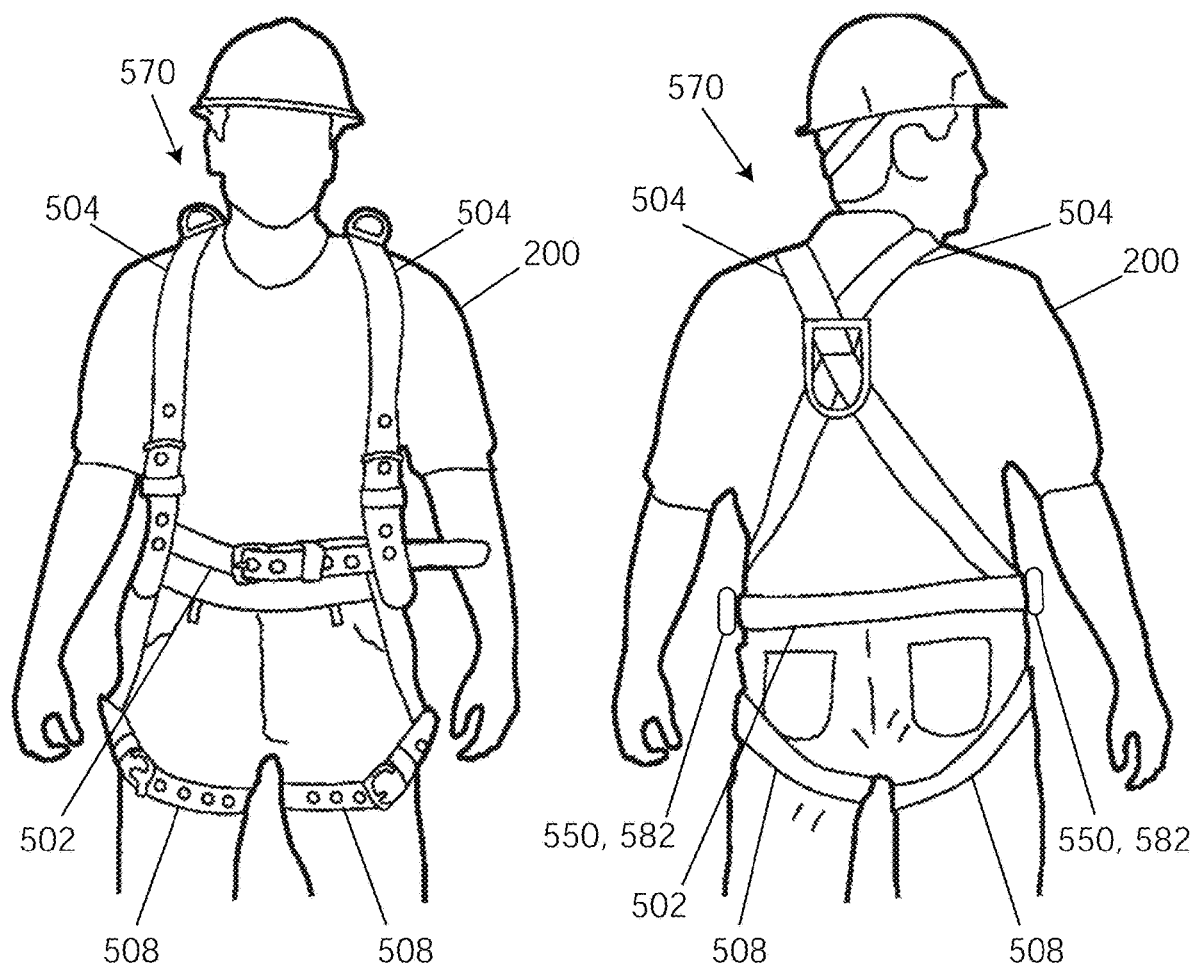
FIG. 40 depicts a fall protection safety harness.
Figure 41:
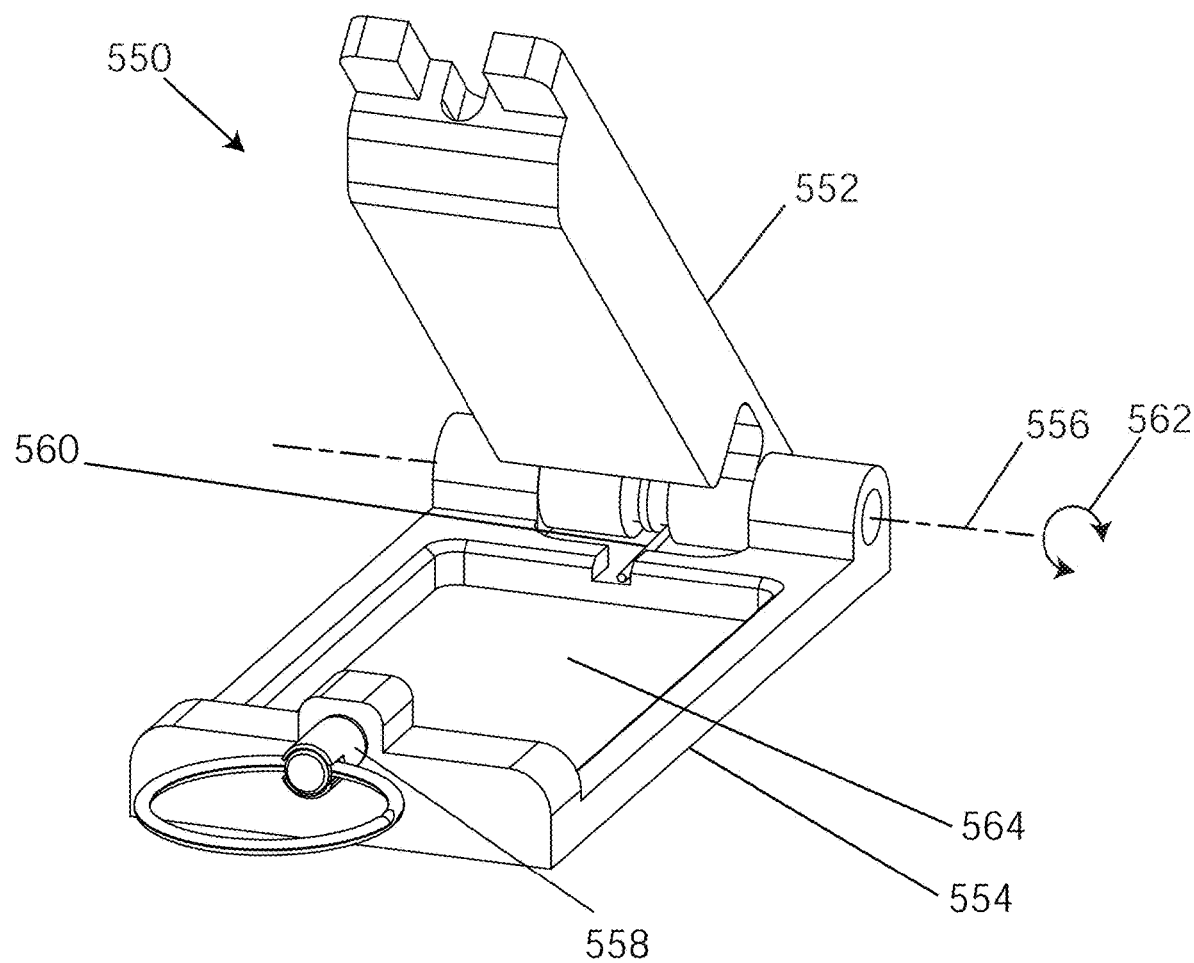
FIG. 41 depicts an embodiment of a coupling device.
Figure 42:
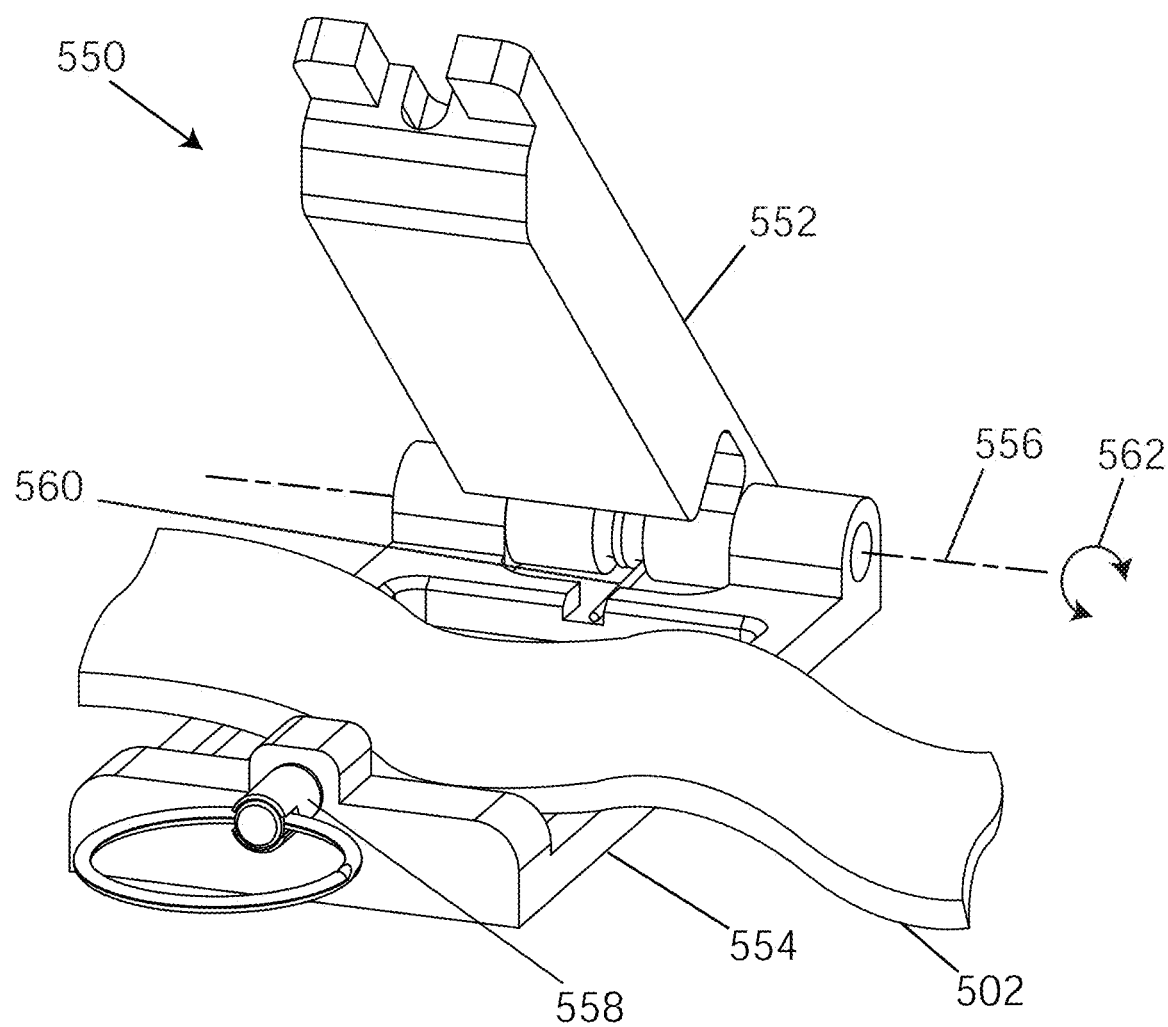
FIG. 42 depicts an embodiment of a coupling device.
Figure 43:
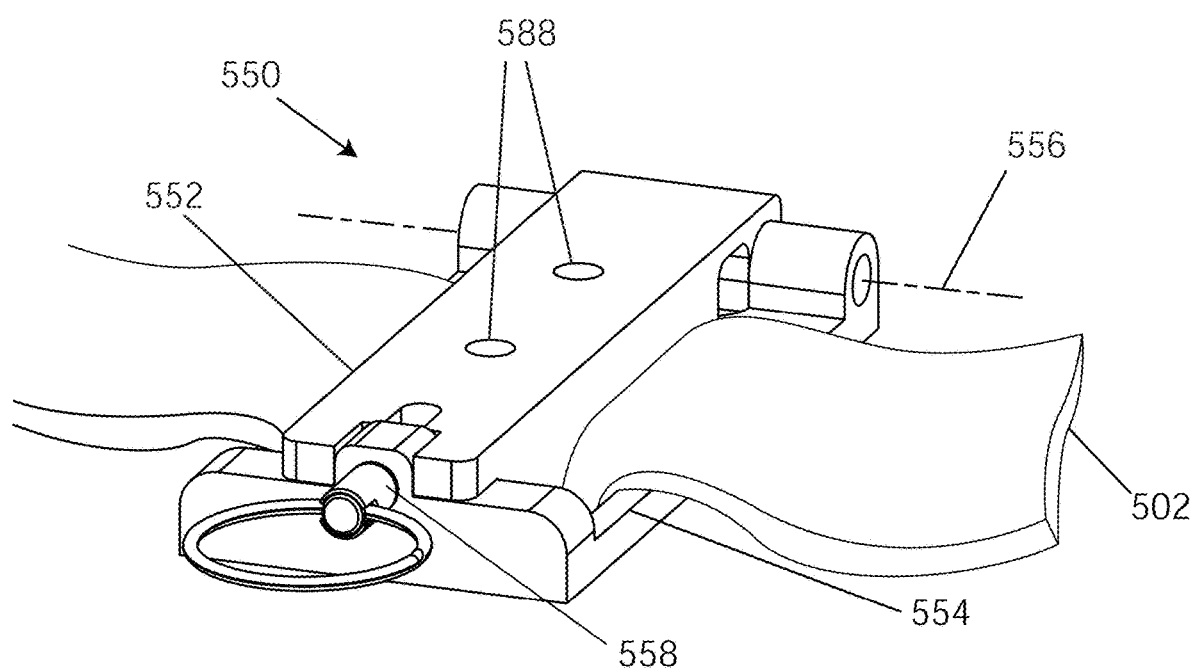
FIG. 43 depicts an embodiment of a coupling device.
Figure 44:
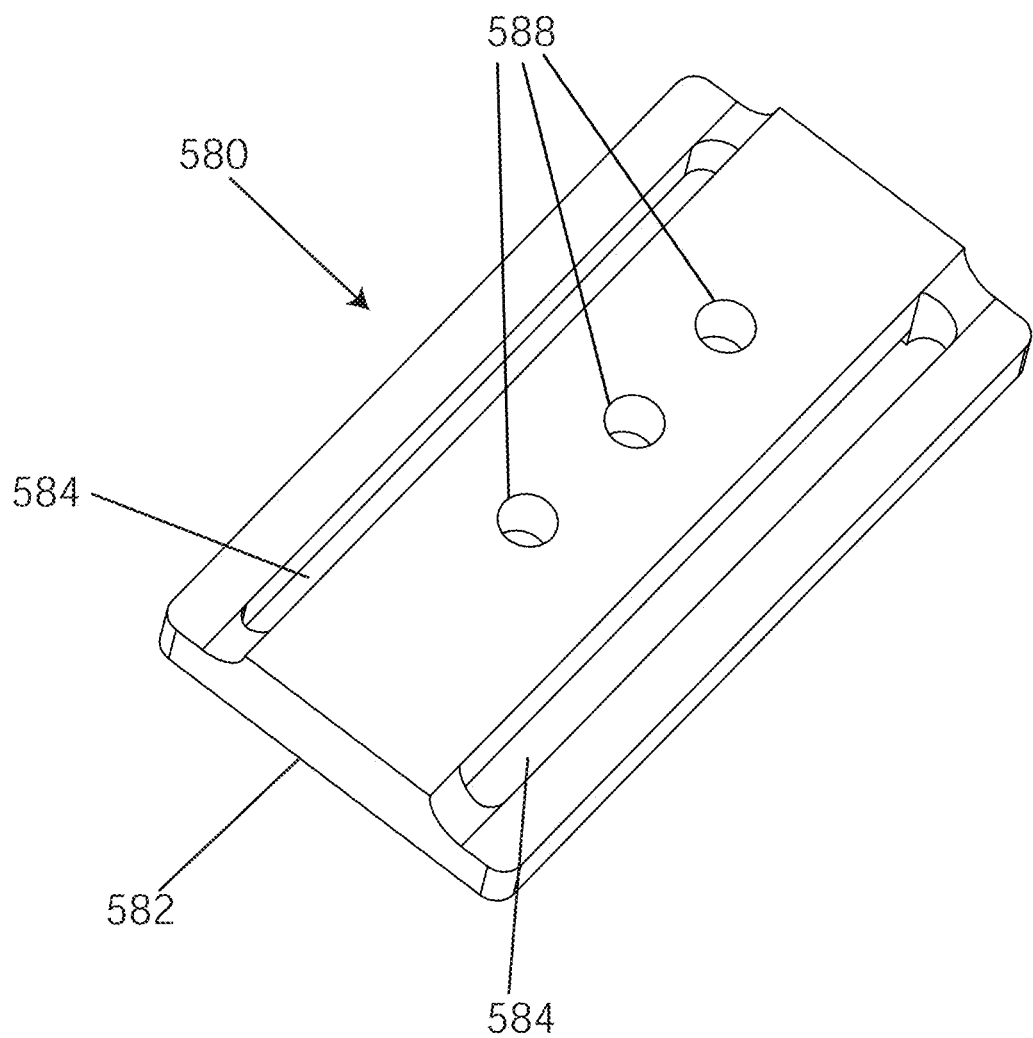
FIG. 44 depicts an embodiment of a coupling device.
Figure 45:
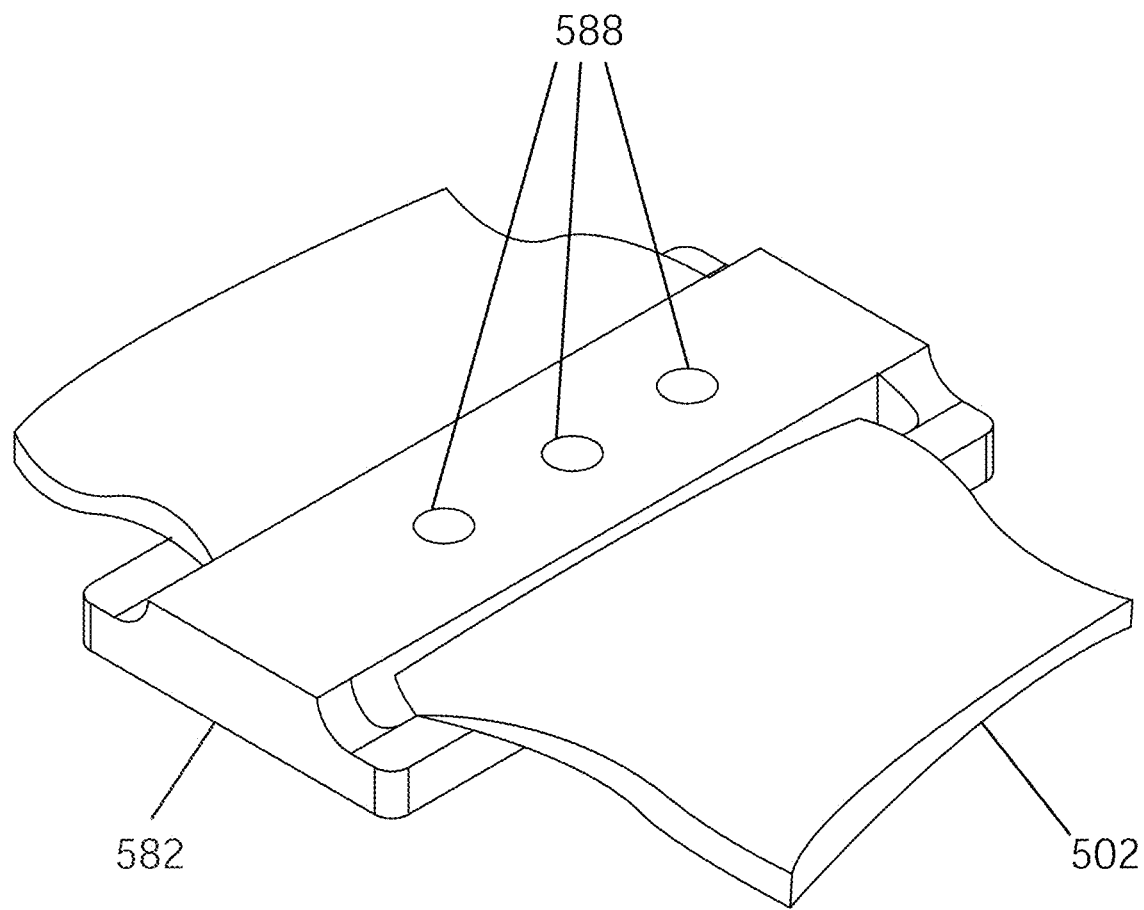
FIG. 45 depicts an embodiment of a coupling device.

There are many methods of coupling either button 540 or holding bracket 532 to waist belt 502 of human interface system 500 or fall protection safety harness 570. FIG. 41 shows an embodiment of a coupling device, clamping device 550, which that allows for such a safe coupling of button 540 or holding bracket 532 to any waist belt 502 of human interface system 500 or fall protection safety harness 570. Clamping device 550 comprises an outer plate 552 which is configured to be coupled to exoskeleton and in inner plate 554. Outer plate 552 has interface or coupling features such as threaded holes 588 to couple to a holding bracket 532 or button 540, as shown in FIG. 43. In some embodiments, inner plate 554 comprises cavity 564 to allow the belt to curve. In operation when inner plate 554 and outer plate 552 are pushed against each other, waist belt 502 is clamped between inner plate 554 and outer plate 552. In some embodiments, inner plate 554 and outer plate 552 rotate relative to each other along axis 556. Arrow 562 shows the direction of motion inner plate 554 and outer plate 552 relative to each other. In some embodiments, a torsion spring 560 can be used to keep two inner plate 554 and outer plate 552 either open or closed relative to each other. FIG. 42 shows the configuration where two inner plate 554 and outer plate 552 are in open position. FIG. 43 shows the situation where waist belt 502 of human interface system 500 or fall protection safety harness 570 is clamped in clamping device 550. Outer plate 552 has interface features such as threaded holes 588 to couple to a holding bracket 532 or a button 504. Spring plunger 558 is used to lock and release outer plate 552 from its clamping position. When spring plunger 558 is pulled out plate 552 gets released. In some embodiments, inner plate 554 and said outer plate 552 are pushed against each other by use of fasteners. FIG. 40 shows an embodiment where clamping device 550 is employed to couple an exoskeleton to fall protection safety harness 570. FIGS. 44 and 45 show another embodiment of coupling device 580 to couple an exoskeleton to a waist belt 502 worn by a wearer. Coupling device 580 comprises a block 582. Block 582 comprises two openings 584. When waist belt 502 passes through two openings 584, waist belt 502 is secured to block 582. Coupling features 588 are used to couple block 582 to an exoskeleton.

Figure 18:
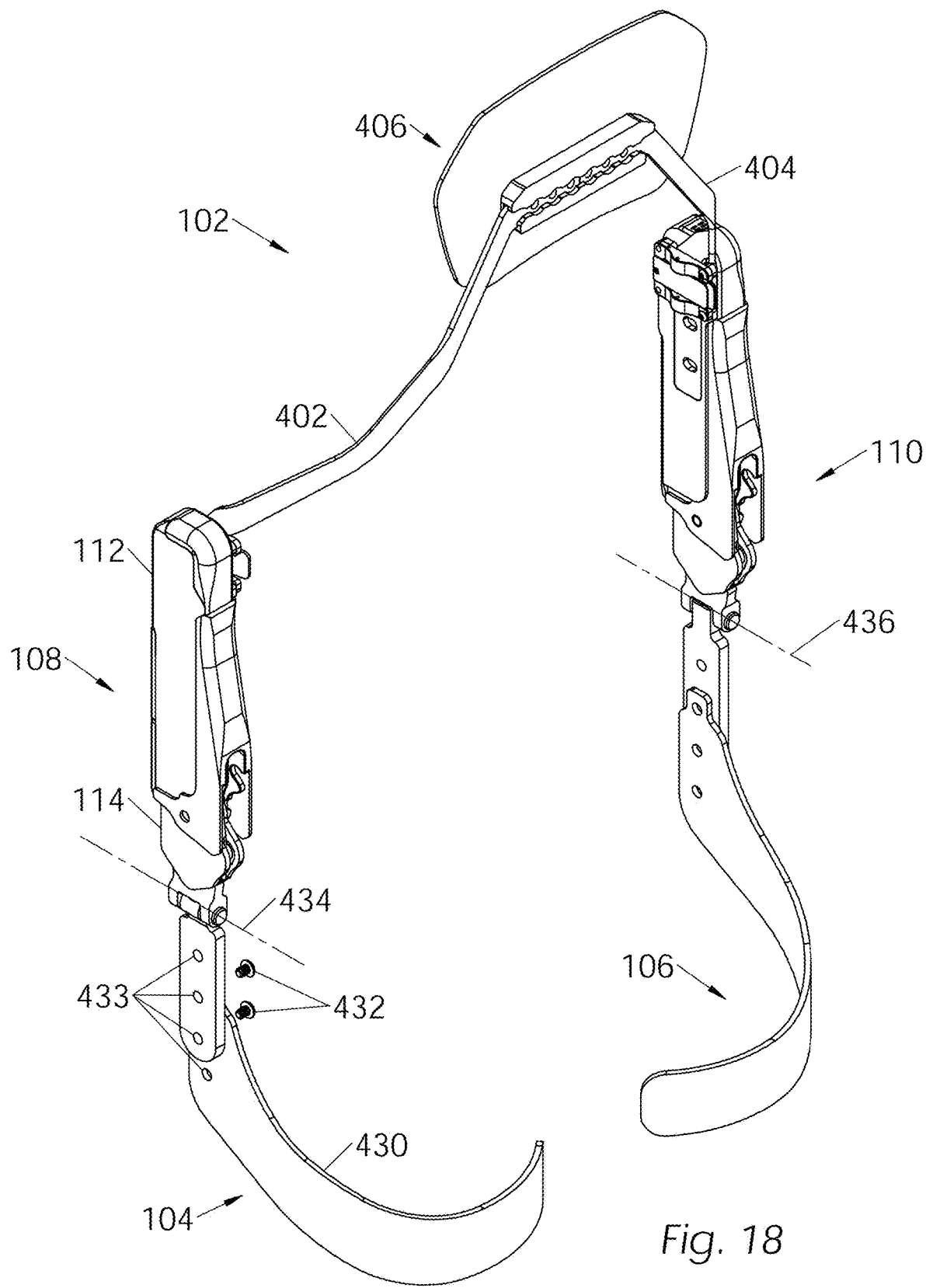
FIG. 18 depicts an embodiment of supporting trunk.

In some embodiments, as shown in FIG. 18, thigh links 104 and 106 further comprise two rotary abduction-adduction axes 434 and 436. Since thigh links 104 and 106 are mirrored, only thigh link 104 is described here. As shown in FIG. 18, thigh links 104 and 106 are able to rotate along axes 434 and 436. In some embodiments, thigh links 104 comprises at least one thigh brace 430 configured to couple to wearer's thigh. Thigh brace 430 comprises any material or combination of materials capable of performing the indicated functions. Examples of materials of thigh brace 430 includes, without limitation, fabric materials, plastic materials, leather materials, carbon fiber materials, metallic materials, and combinations thereof. In some embodiments, thigh links 104 and 106 are adjustable in length for to fit various wearers. As shown in FIG. 18, in some embodiments, thigh holes 433 and fasteners 432 are used to adjust the location of thigh brace 430.

In general, human interface system 500 is intended to couple trunk supporting exoskeleton 100 to wearer 200. In some embodiments, as for example shown in FIG. 35 and FIG. 36, human interface system 500 comprises waist belt 502, which is configured to be worn on the waist of wearer 200. In some embodiments, human interface system 500 comprises two shoulder straps 504, which are configured to be worn on the shoulders of wearer 200. In some embodiments, human interface system 500 comprises chest strap 506, which is configured to be worn on the chest of wearer 200. In some embodiments, human interface system 500 comprises two thigh straps 508, which are configured to be worn around the thighs of wearer 200. In some embodiments, human interface system 500 comprises bridge strap 510, connecting two thigh straps 508 behind wearer 200. In general, human interface system 500 is configured to couple trunk supporting exoskeleton 100 to wearer 200. Human interface system 500 may comprise any device or any combination of devices capable of performing the indicated function. In particular, human interface system 500 may comprise an element or a combination of elements selected from the group consisting of waist belt 502 (configured to be worn on the waist of wearer 200), two shoulder straps 504 (configured to be worn on the shoulders of wearer 200), two thigh straps 508 (configured to be worn around the thighs of wearer 200), bridge strap 510 (for connecting two thigh straps 508), chest strap 506, and any combination thereof. Depending on the work environment, an ordinary skilled in the art can design human interface system 500 to comprise an element or a combination of elements described above. These elements can be used as a human interface system, either individually or in combination, to couple trunk supporting exoskeleton 100 and wearer 200 to each other.

Figure 66:
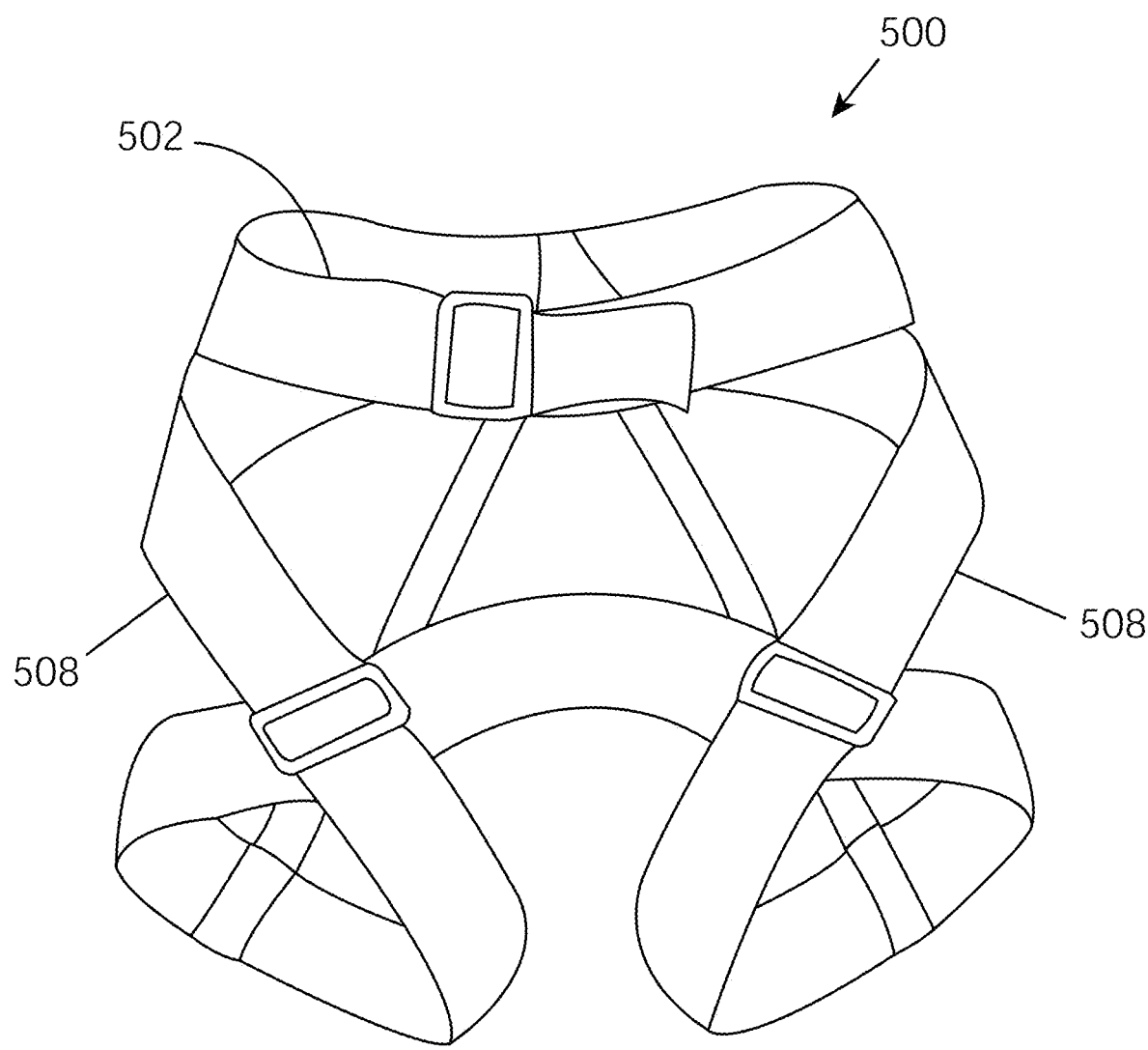
FIG. 66 depicts an embodiment in which the human interface system comprises a climbing harness.
Figure 67:
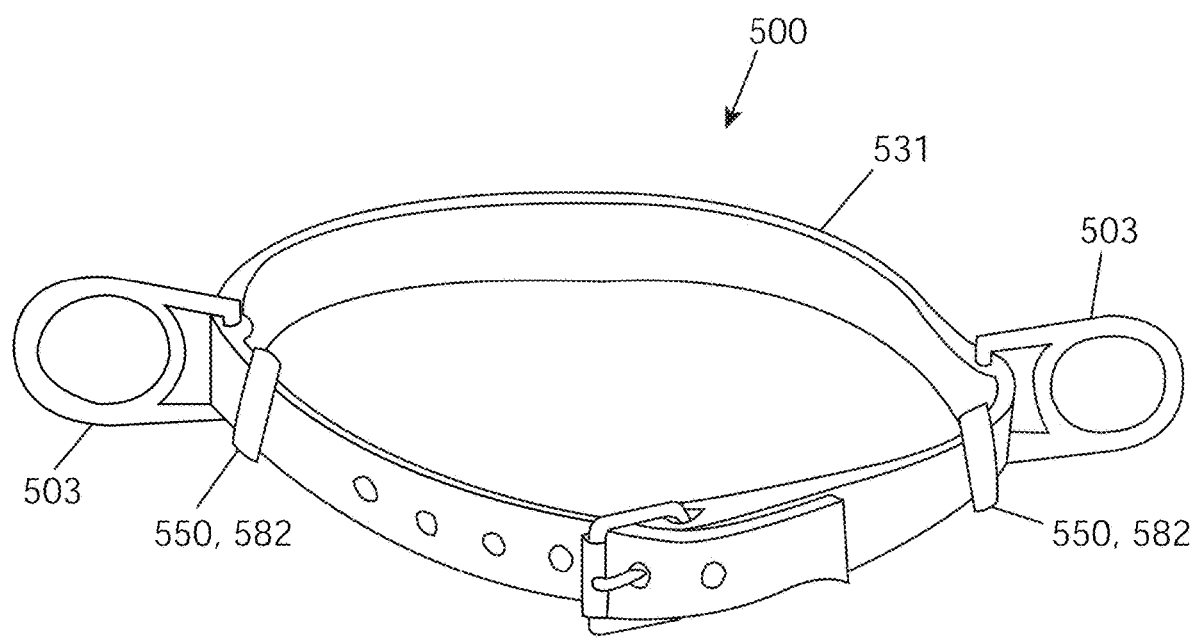
FIG. 67 depicts an embodiment in which the human interface system comprises a safety belt.
Figure 68:
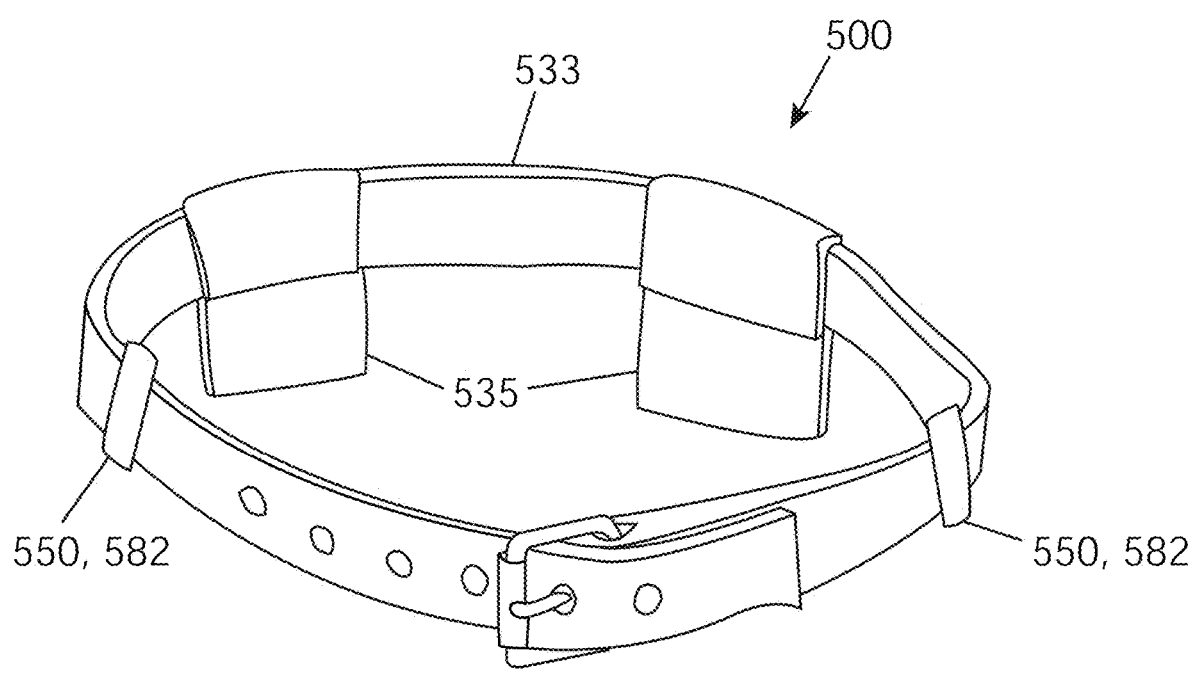
FIG. 68 depicts an embodiment in which the human interface system comprises a tool belt.

Also provided is a safety harnesses, which may be used by workers in various environments (e.g., construction sites and ship building facilities) and which may be deployed as human interface system 500. In some embodiments, as shown in FIG. 40, human interface system 500 comprises fall protection safety harness 570. In some embodiments, as shown in FIG. 66, human interface system 500 comprises a climbing harness. In some embodiments, human interface system 500 comprises a fall prevention safety harness. In general, an ordinary skilled in the art can recognize that human interface system 500 can comprise any safety harness or combination of safety harnesses capable of performing the indicated function of coupling trunk supporting exoskeleton 100 to wearer 200 in addition to securing safety for the wearer. It should be understood, human interface system 500 can be selected from the group comprising of a safety harness, a safety belt, a fall protection safety harness, a climbing harness, a fall prevention safety harness, and any combination thereof. In some embodiments, as shown in FIG. 68, human interface system 500 comprises tool belt 533. Tool belt 533, as shown in FIG. 68, may comprise holster 535 to keep various tools. In some embodiments, as shown in FIG. 67, human interface system 500 comprises safety belt 531. Safety belt 531, shown in FIG. 67, may comprise at least one hook 503, to secure wearer 200 to a structure for safety.

Provided are various methods of coupling trunk supporting exoskeleton 100 to human interface system 500. The important issue is to ensure trunk supporting exoskeleton 100 is coupled to human interface system 500 such that trunk supporting exoskeleton 100 robustly stays on wearer 200 during all kinds of maneuvers. The advantage of using a safety harness, a safety belt, a climbing harness, and/or a fall protection safety harness as human interface system 500 is that two functions are achieved simultaneously: the wearer's safety is secured, and trunk supporting exoskeleton 100 is coupled to wearer 200.

This disclosure teaches how trunk supporting exoskeleton 100 can be coupled to human interface system 500. One way is to ensure human interface system 500 is already coupled to the rest of trunk supporting exoskeleton 100 before wearing trunk supporting exoskeleton 100. Another way is to wear human interface system 500 first. After human interface system 500 is worn, wearer 200 will couple the rest of trunk supporting exoskeleton 100 to human interface system 500. To realize this feature, robust coupling device 613 may be used to couple human interface system 500 to the rest of trunk supporting exoskeleton 100. In general coupling device 613 may be designed to couple human interface system 500 and at least a component of trunk supporting exoskeleton 100 together. Various options are within the scope of this disclosure. In some embodiments, supporting trunk 102 can be coupled to human interface system 500. In some embodiments, torque generator 108 and 110 can be coupled to human interface system 500. In some embodiments, thigh links 104 and 106 can be coupled to human interface system 500. In general, human interface system 500 can be coupled to a component or combination of components selected from a set compromising supporting trunk 102, torque generators 108 and 110 and thigh links 104 and 106.

Figure 46:
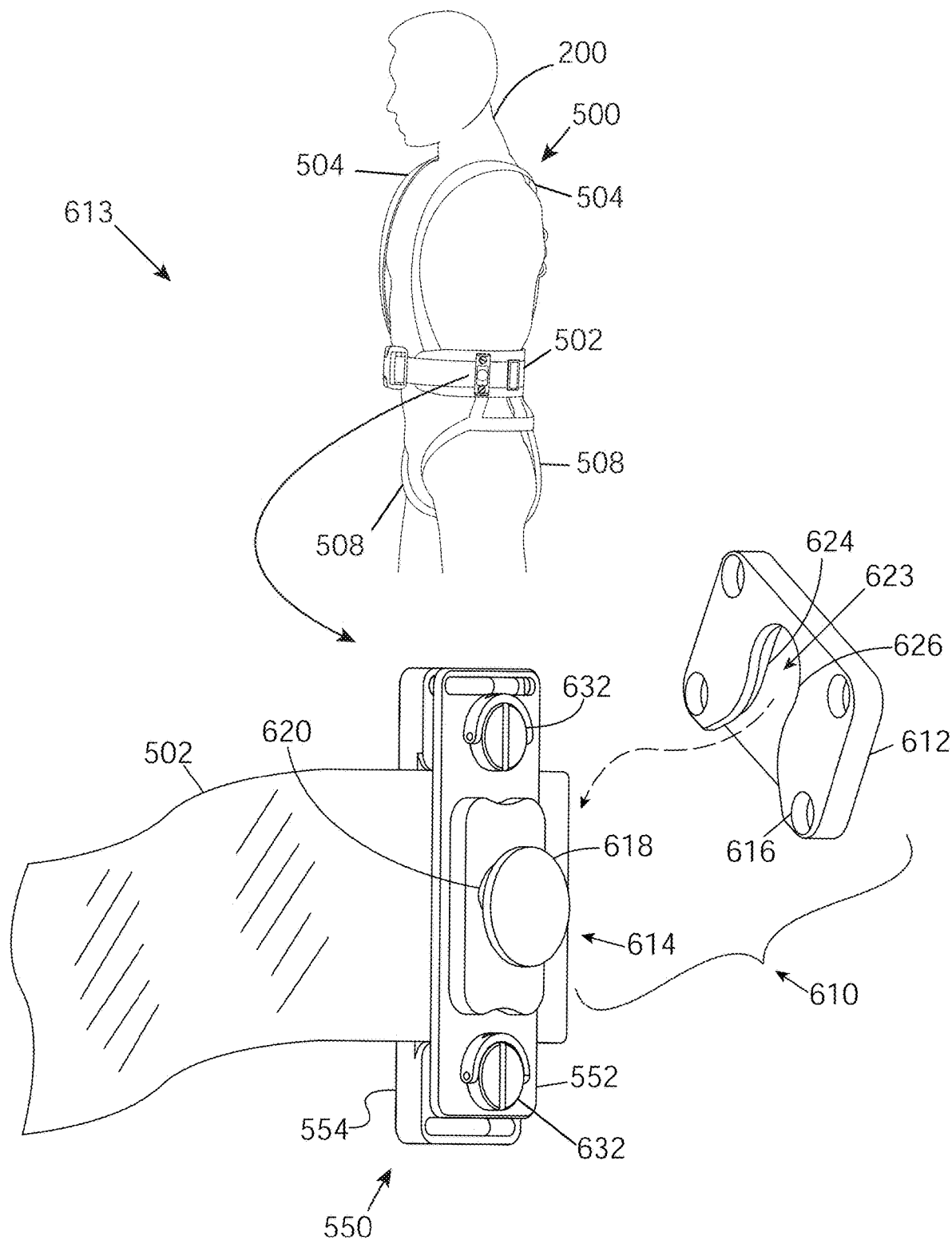
FIG. 46 depicts an embodiment of a quick release mechanism that is used to couple supporting trunk to a waist belt.

This disclosure teaches the general form of coupling device 613 that allows trunk supporting exoskeleton 100 to be coupled to its wearer 200. An embodiment of coupling device 613 is shown in FIG. 46 which comprises human interface system 500 and quick release mechanism 610. Human interface system 500, which may comprise waist belt 502 (as shown in FIG. 46), may be configured to be worn by wearer 200. Quick release mechanism 610, which may comprise at least a first configuration and a second configuration, for coupling and uncoupling human interface system 500 (comprising waist belt 502 in FIG. 46) to at least one component of trunk supporting exoskeleton 100. Trunk supporting exoskeleton 100 is not shown in FIG. 46. However, FIGS. 52, 53, 54 and 56 show trunk supporting exoskeleton 100 in conjunction with coupling device 613 (quick release mechanism 610 and human machine interface 500).

The operation of coupling device 613 is described below. When quick release mechanism 610 is in the first configuration, quick release mechanism 610 is configured to couple trunk supporting exoskeleton 100 to human interface system 500 in a manner that prevents trunk supporting exoskeleton 100 from becoming uncoupled from human interface system 500. When quick release mechanism 610 is in the second configuration, quick release mechanism 610 is configured in a manner to allow trunk supporting exoskeleton 100 to be uncoupled from human interface system 500. This allows the wearer wear human interface 500 first. After human interface 500 is worn, wearer 200 will couple the rest of trunk supporting exoskeleton 100 to human interface 500 through the use of quick release mechanism 610.

FIG. 46 shows an embodiment of quick release mechanism 610 for coupling trunk support exoskeleton 100 and human interface system 500 to each other. FIG. 46 specifically depicts the coupling of supporting trunk 102 (a component of trunk support exoskeleton 100) to waist belt 502, which may be also a tool belt, a safety belt or any kind of belt (or, more generally, a component of human interface system 500). Although this example is described in the context of trunk support exoskeleton 100, it will be understood that quick release mechanism 610 described below can be used to couple any exoskeleton to human interface system 500. Quick release mechanism 610 may comprise holding bracket 612 and button assembly 614. Button assembly 614 and holding bracket 612, each is operable to be coupled to either supporting trunk 102 or waist belt 502. For example, if holding bracket 612 is coupled to supporting trunk 102 (or torque generators 108 and 110, or thigh links 104 and 106), then button assembly 614 will be coupled to waist belt 502. (shown in FIG. 46). In another example, if holding bracket 612 is coupled to waist belt 502, then button assembly 614 will be coupled to supporting trunk 102 (or torque generators 108 and 110). For brevity, only the case where button assembly 614 is coupled to a waist belt 502 is described here.

Figure 52:
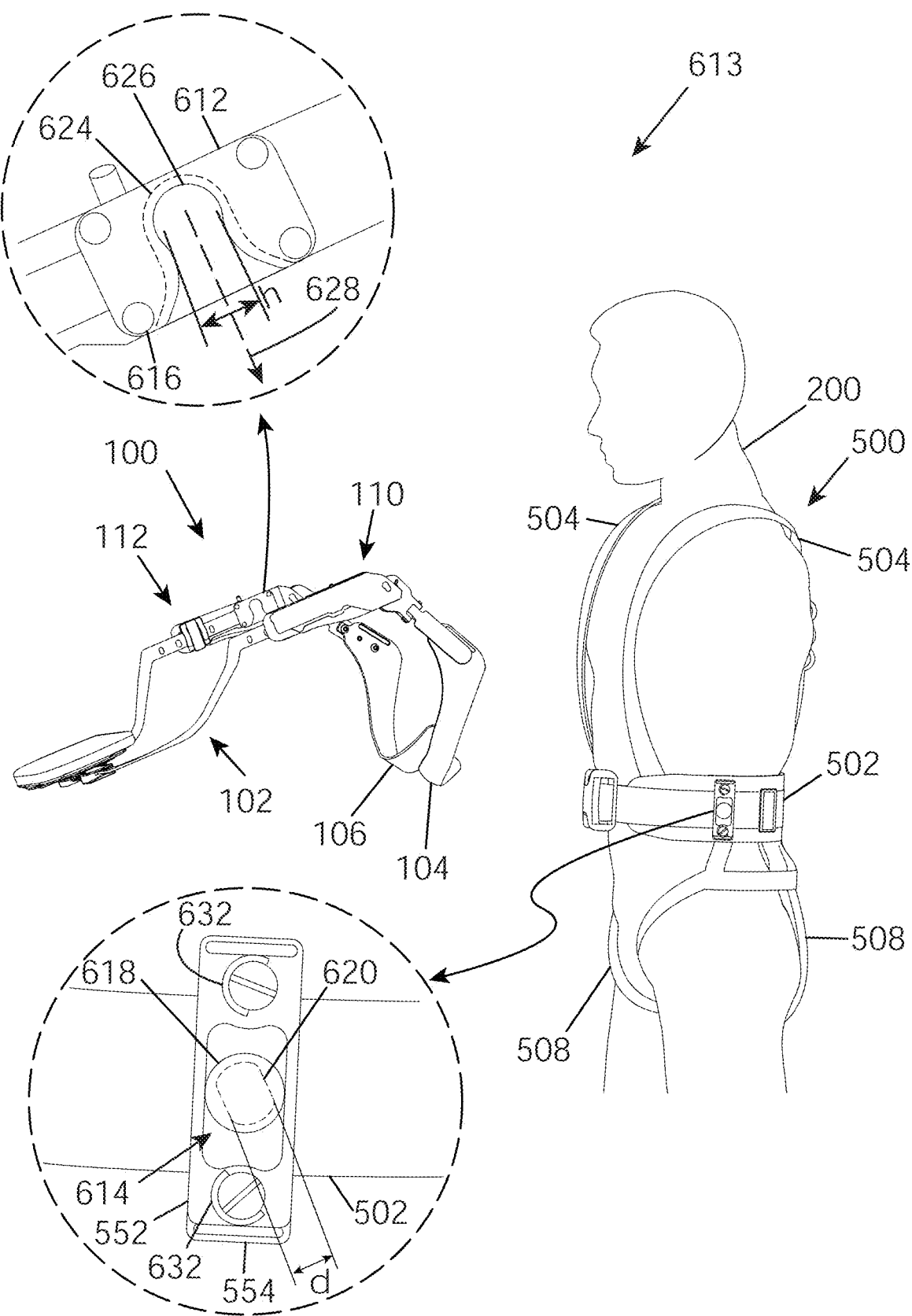
FIG. 52 depicts an embodiment in which the supporting trunk has a particular orientation such that the button assembly can be moved into the cavity.

FIG. 46 shows button assembly 614 is coupled to waist belt 502. Although not shown in FIG. 46, holding bracket 612 is coupled to at least one component of trunk supporting exoskeleton 100. FIG. 52 shows holding bracket 612 is coupled to torque generator 112. In some embodiments, holding bracket 612 is coupled to torque generators 108 and 110. In some embodiments, holding bracket 612 is coupled to supporting trunk 102. In some embodiments, holding bracket 612 is coupled to thigh links 104 and 106. Fastener holes 616 are created in holding bracket 612 to couple holding bracket 612 to at least one component of trunk supporting exoskeleton 100 (e.g. supporting trunk 102).

Figure 47:
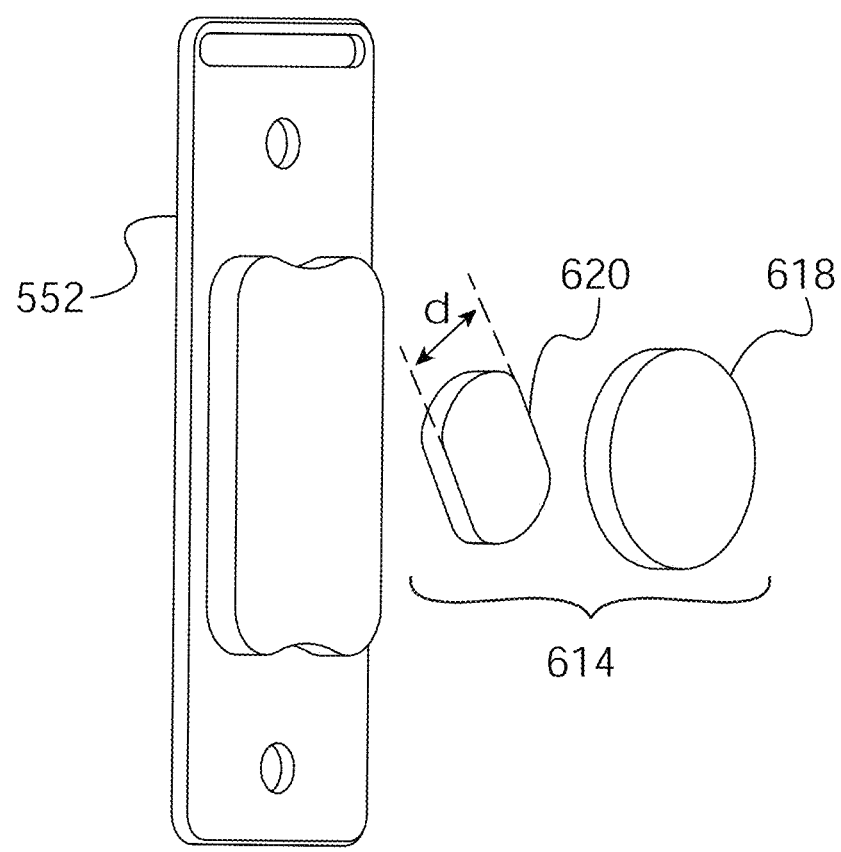
FIG. 47 depicts an embodiment of a button assembly.

In some embodiments, as shown in FIG. 47, button assembly 614 comprises button head 618 and button neck 620. Button neck 620 may be coupled to outer plate 552. Button neck 620, button head 618 and outer plate 552 are either made as one part or several parts coupled to each other. FIG. 47 shows button assembly 614, in which button neck 620, button head 618 and outer plate 552 are separated for clarity. One of ordinary skill in the art would be able to design all kinds of button assembly with the intended function described below.

Figure 48:
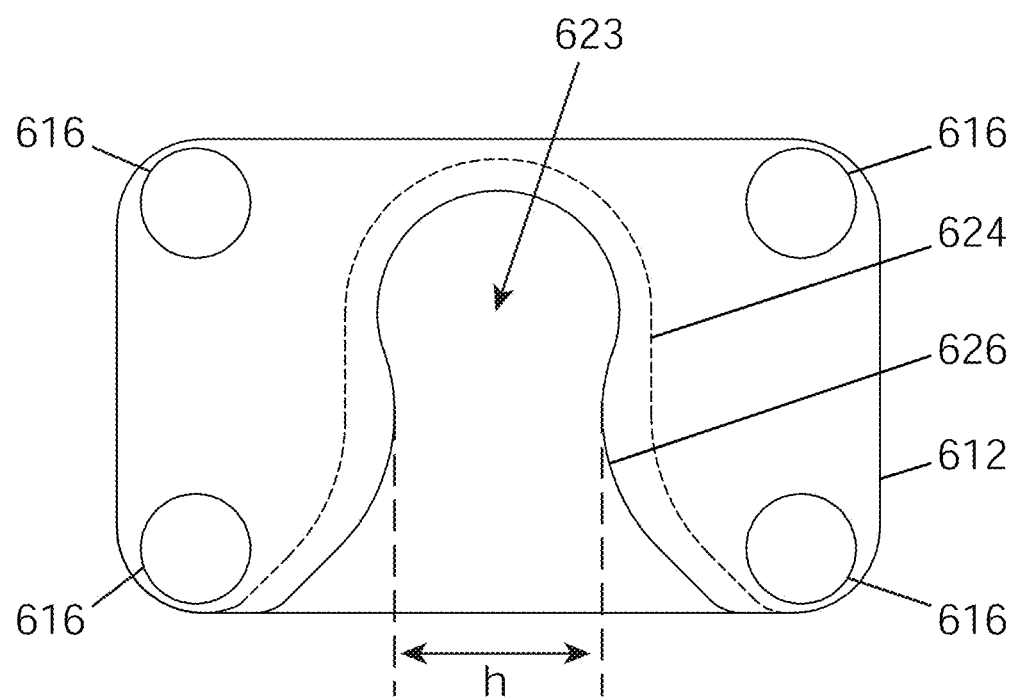
FIG. 48 depicts a cavity formed within holding bracket to accommodate a button assembly of one embodiment of a coupling device.

As shown in FIG. 46 and FIG. 48, in some embodiments, cavity 623 is formed within holding bracket 612. In some embodiments, cavity 623 comprises lower cavity 624 and upper cavity 626, which are formed within holding bracket 612 to accommodate button head 618 and button neck 620. In some embodiments, as shown in FIG. 46 and FIG. 48, lower cavity 624 has the same shape of button head 618 and button head 618 can easily slide into lower cavity 624. However, upper cavity 626 has a shape such that button neck 620 can be moved into upper cavity 626 only along a particular direction.

Figure 49:
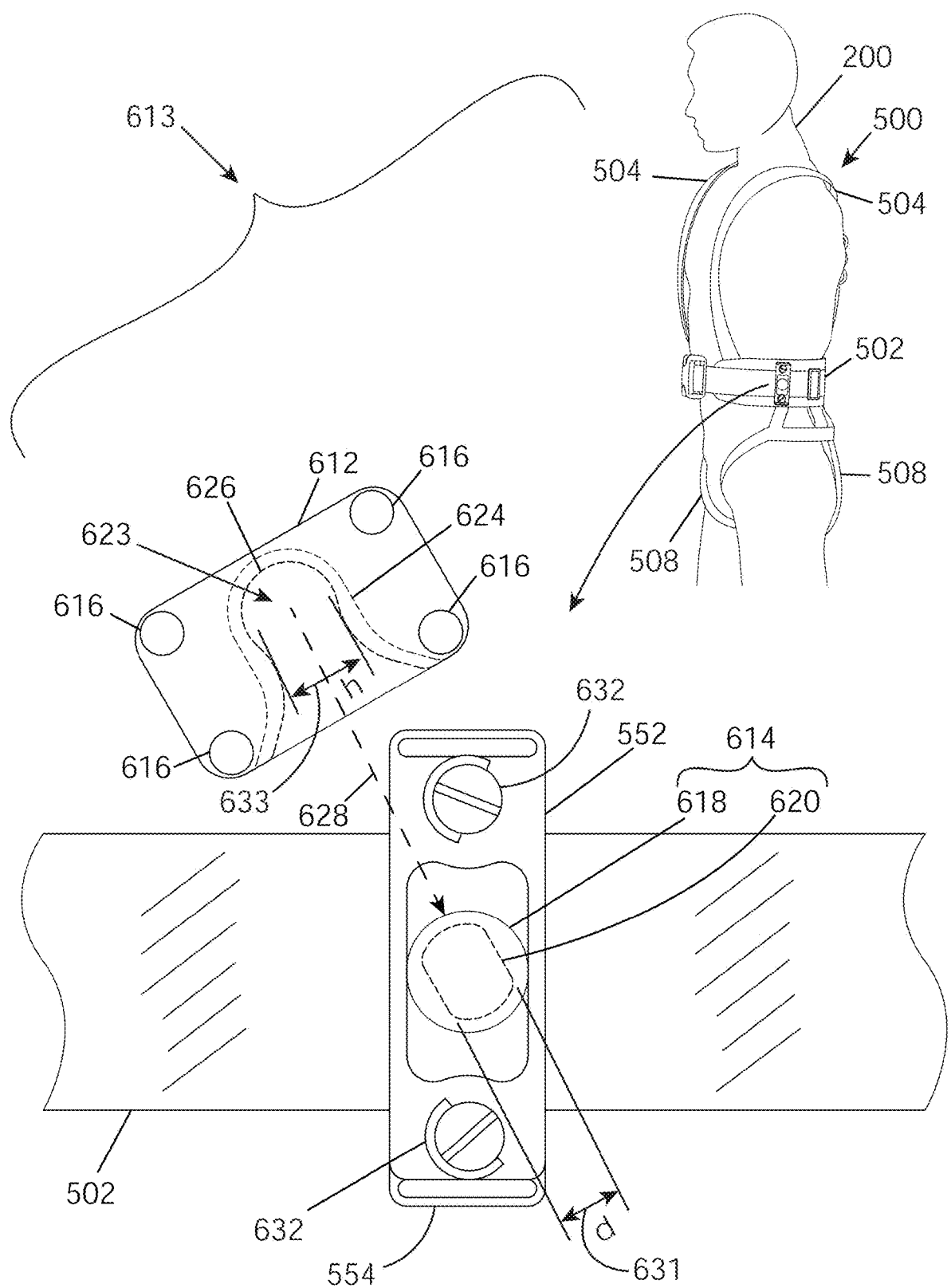
FIG. 49 depicts an embodiment of a button assembly and holding bracket, in which the button assembly and the holding bracket not coupled to each other.
Figure 50:
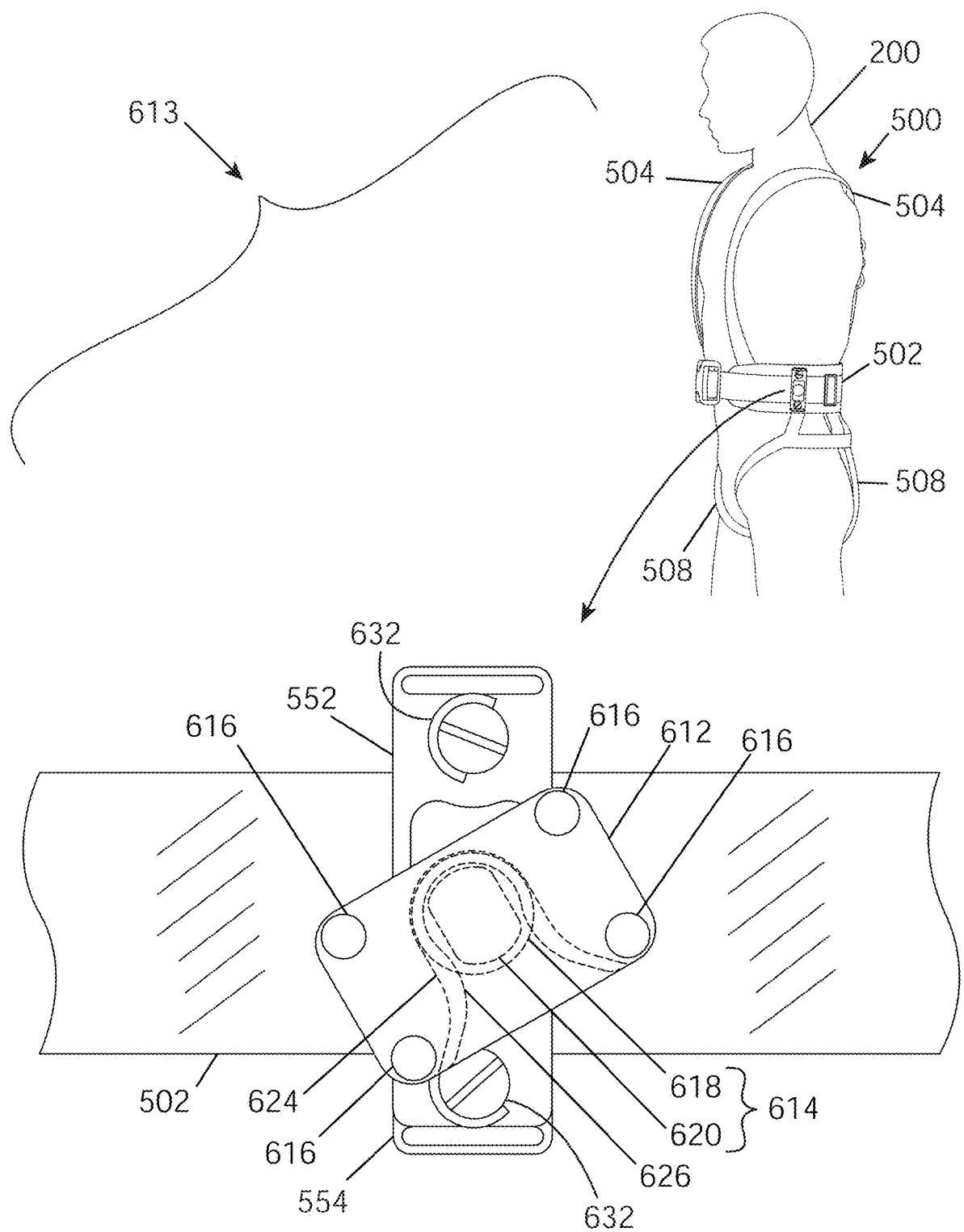
FIG. 50 depicts an embodiment in which the button neck and the button head have moved into the upper cavity and the lower cavity.

FIG. 49 shows button assembly 614 and holding bracket 612 when they are not coupled to each other. When holding bracket 612 is moved relative to button assembly 614 along arrow 628, button neck 620 and button head 618 move into upper cavity 626 and lower cavity 624. This is shown in FIG. 50. Button neck 620 has a minimum cross section profile 631 (measured as d) that can be moved into upper cavity 626 only along the direction shown in FIG. 49. This is true because upper cavity 626 has an opening profile 633 (measured as h) that can accommodate button neck 620 only along direction 628. It can be observed in FIGS. 47, 48 and 49 that button neck 620 has a minimum cross section profile 631 (measured by d) and upper cavity 626 has an opening 633 (measured by d). In this embodiment, d is smaller than h and therefore button assembly 614 can be moved into cavity 623 only when button assembly 614 and cavity 623 are aligned relative to each other as shown by arrow 628.

Once button assembly 614 is moved into holding bracket 612, then it can always come out along the same direction.

Figure 51:
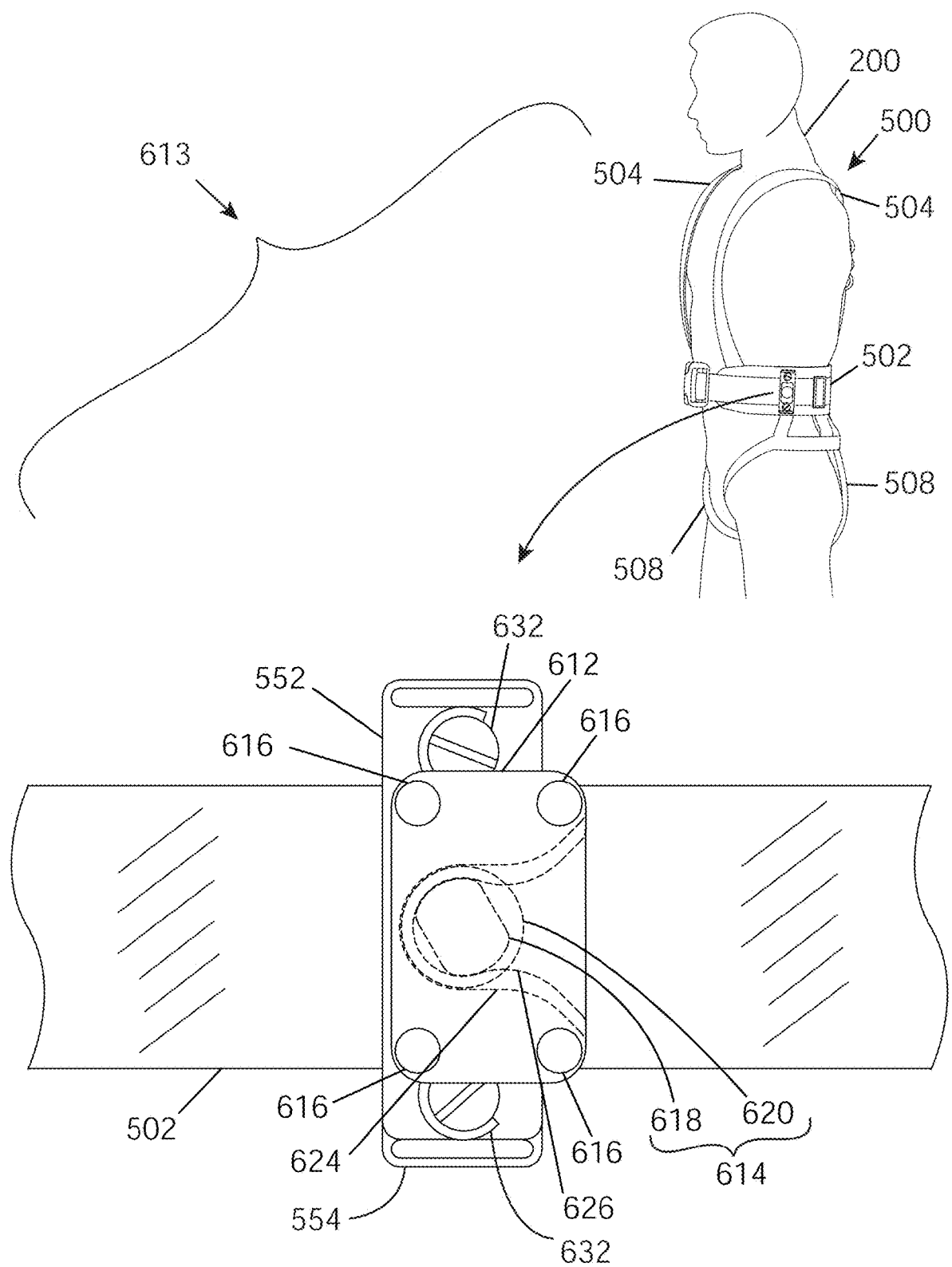
FIG. 51 depicts an embodiment in which the button assembly is rotated relative to the holding bracket, such that the button assembly and the holding bracket cannot be separated from each other.

However, if one rotates button assembly 614 relative to holding plate 612 (as shown in FIG. 51), button assembly 614 and holding bracket 612 cannot be separated from each other. In order to separate holding bracket 612 from button assembly 614, button assembly 614 and holding bracket 612 need to be rotated to be in the orientation shown in FIG. 50.

Figure 53:
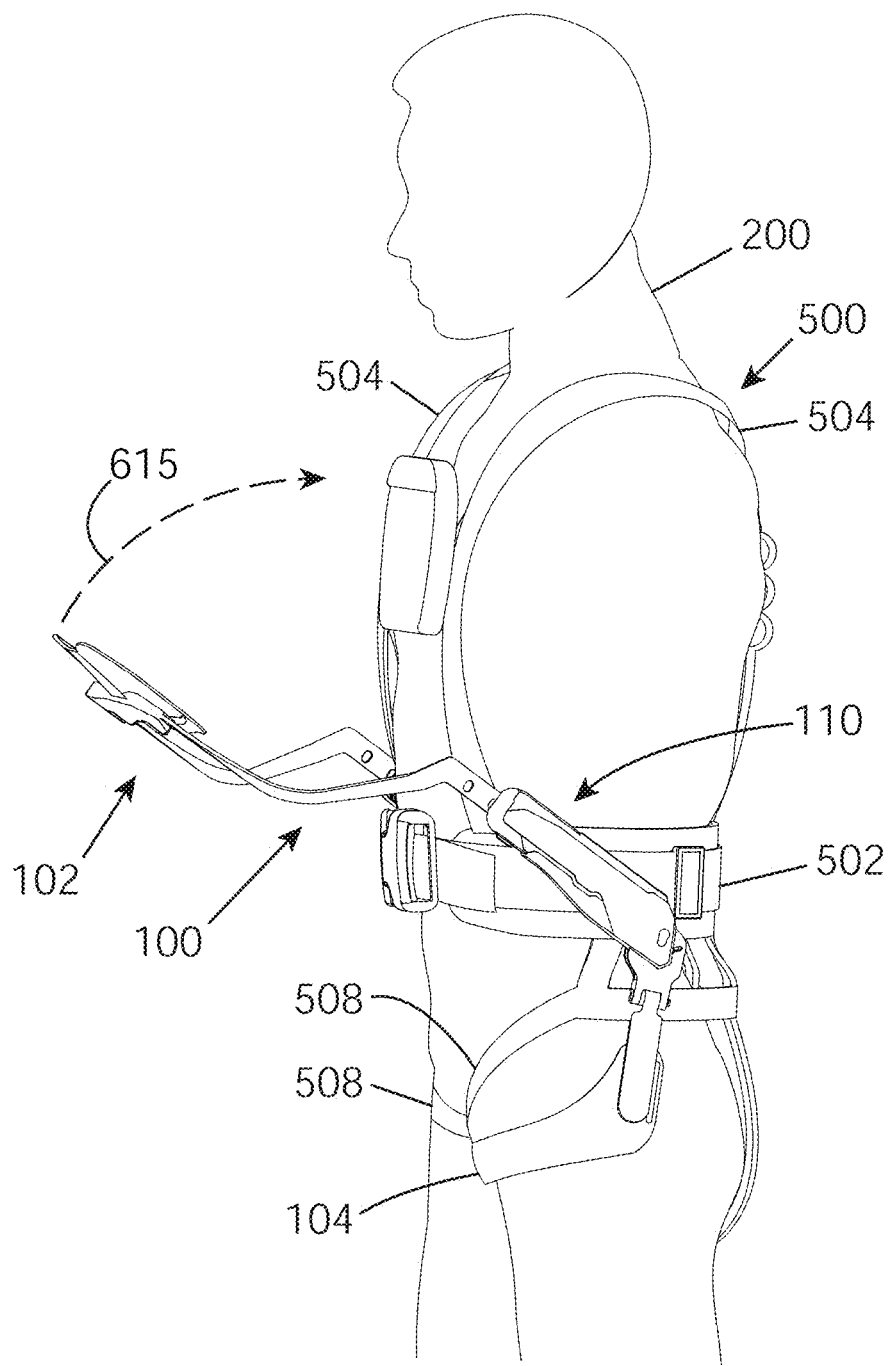
FIG. 53 depicts an embodiment in which the supporting trunk and its attached button assembly is about to rotate while the button assembly is inside the cavity.
Figure 54:
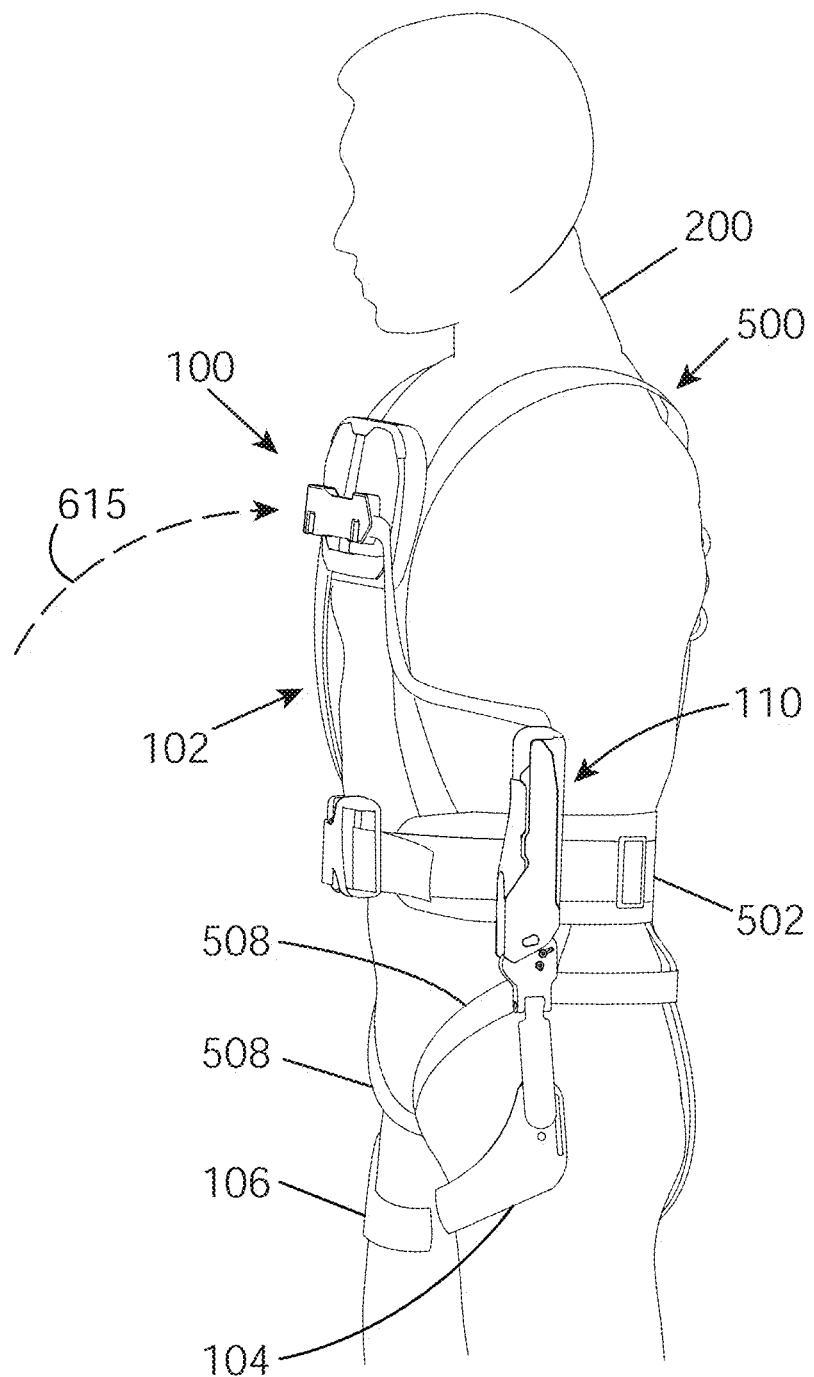
FIG. 54 depicts an embodiment in which a supporting trunk has been turned to fit the wearer.

FIG. 52 shows the situation where supporting trunk 102 has a particular orientation such that button assembly 614 can be moved into cavity 623. FIG. 53 shows the situation where supporting trunk 102 and its attached button assembly 614 is about to rotate along direction arrow 615 while button assembly 614 is inside cavity 623. FIG. 54 shows the situation where supporting trunk 102 has rotated along direction arrow 615 to fit wearer 200. In this situation (FIG. 54) supporting trunk 102 cannot be separated from human interface 500. One needs to rotate supporting trunk 102 such that button assembly 614 can be moved out of cavity 623.

For clarity, this disclosure demonstrates the concept by using the dimensions of minimum cross section profile 631 (measured by d) and opening profile 633 (measured by h.) However, it can be understood, one ordinary skilled in the art can arrive at various shapes of minimum cross section profile 631 and opening profile 633 such that button assembly 614 can be moved into and come out of cavity 623 only along a particular direction.

A teaching of this disclosure is that button assembly 614 comprises a minimum cross section profile 631 and cavity 623 comprises opening profile 633 such that minimum cross section profile 631 (shown by d in FIG. 52) is equal or smaller than the cavity profile 633 (shown by h in FIG. 52). In operation, when button assembly 614 is oriented such that minimum profile 631 is face to face with the cavity opening profile 633, button assembly 614 can be inserted into cavity 623 and moved out of cavity 623. When button assembly 614 is inserted into cavity 623 and aligned such that minimum cross section profile 631 is not face to face with said cavity opening profile 631, button assembly 614 cannot be removed out of cavity 623.

As shown in FIGS. 46 and 52, holding bracket is coupled to at least a component of trunk supporting exoskeleton 100 and button assembly 614 is coupled to at least a component of human interface 500. One can consider an inverse approach where holding bracket is coupled to at least a component of human interface system 500 and button assembly 614 is coupled to at least a component of trunk supporting exoskeleton 100 (e.g. torque generator 108 and 110 or supporting trunk 102).

Also note that although this coupling method is described here for the trunk support exoskeleton 100, it will be understood that the coupling method described above can be used to couple any exoskeleton to human interface system 500. One can consider a situation where holding bracket 612 is coupled to at least a component of human interface system 500 and button assembly 614 is coupled to at least a component of an exoskeleton. Alternatively, button assembly 614 can be coupled to at least a component of human interface system 500 and holding bracket 612 can be coupled to at least a component of an exoskeleton.

Figure 55:
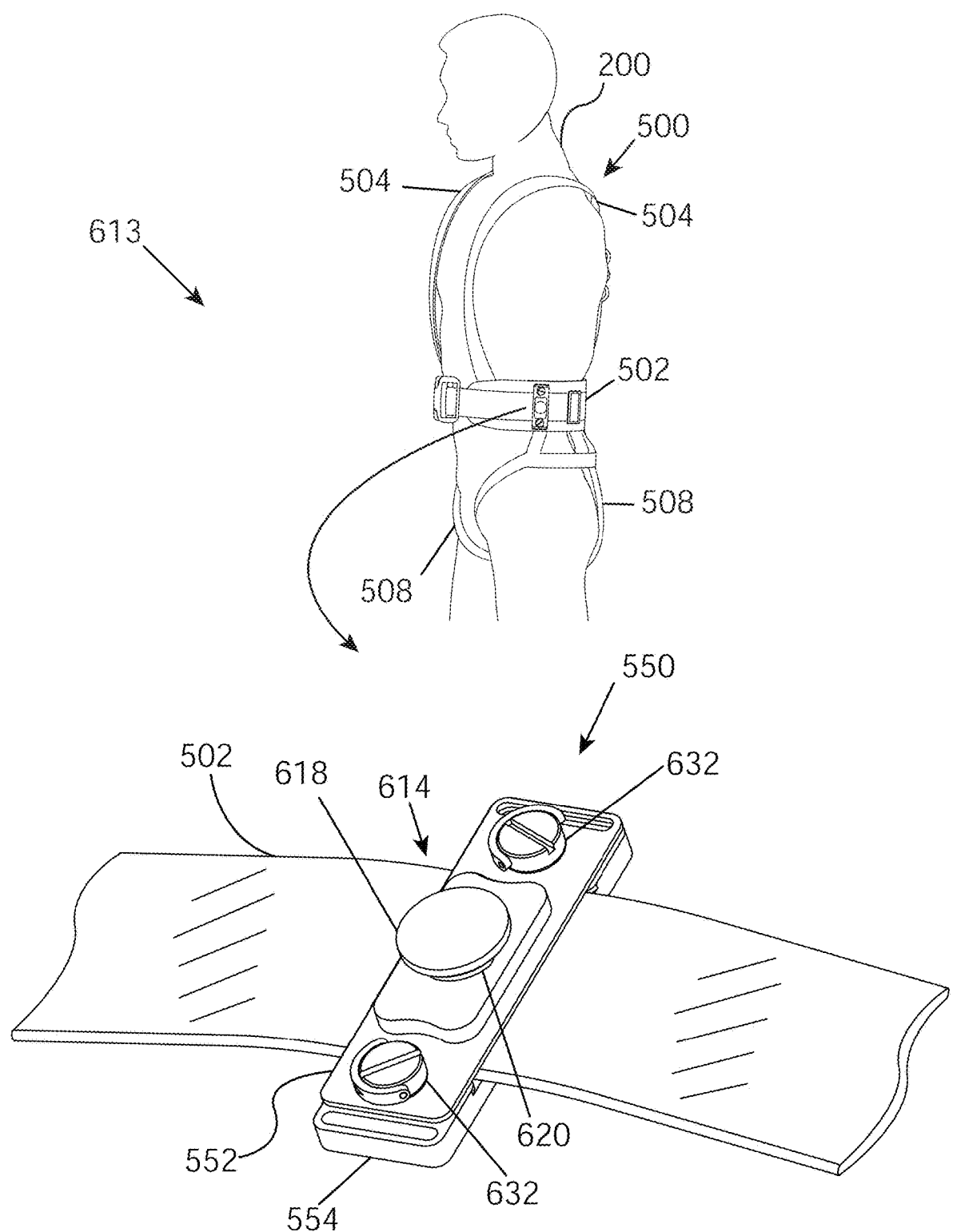
FIG. 55 depicts an embodiment n which the button assembly is coupled to a waist belt.
Figure 56:
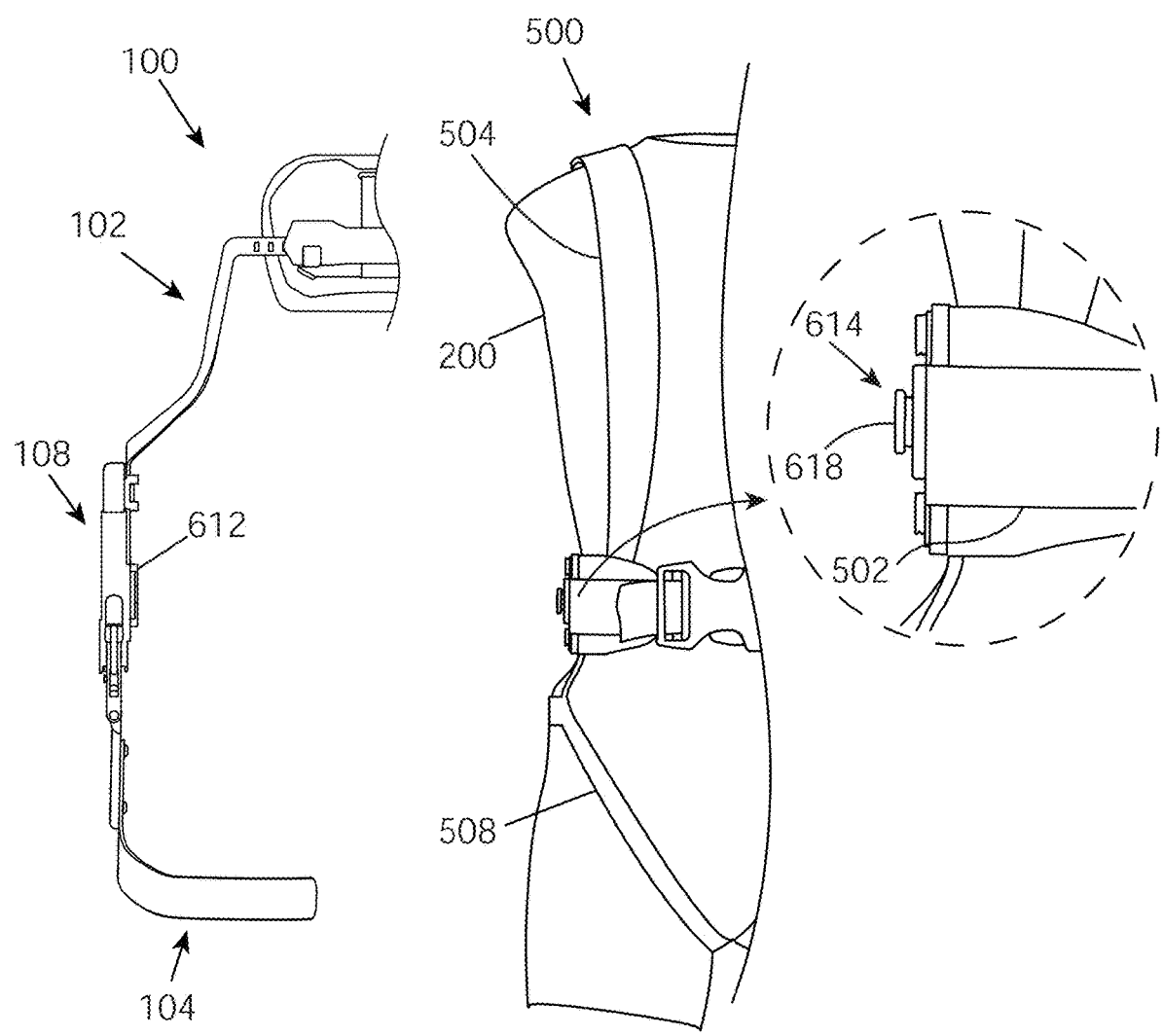
FIG. 56 depicts an embodiment in which two button assemblies are mounted onto two sides of a wearer, and two holding brackets are coupled to two sides of supporting trunk.

The connection of button assembly 614 or holding bracket 612 to human interface system 500 can be done through several methods. As shown in embodiment of FIG. 46, clamping device 550 can be used to couple human interface system 500 to trunk support exoskeleton 100. Clamping device 550 comprises outer plate 552 and inner plate 554. Outer plate 552 is configured to be coupled to trunk support exoskeleton 100. In operation, when inner plate 554 and outer plate 552 are pushed against each other, at least one component of human interface system 100 is clamped between inner plate 554 and outer plate 552. In some embodiments, outer plate 552 is pushed to inner plate 554 through two fasteners 632. In some embodiments waist belt 502 is clamped in between outer plate 552 and inner plate 554 by use of two fasteners 632. FIG. 55 shows the button assembly 614 is coupled to waist belt 502 through clamping device 550. FIG. 56 shows a view where two button assemblies 614 are mounted onto two sides of wearer 200 and two holding brackets 612 are coupled to two sides of supporting trunk 102 through the use of clamping devices 550.

Figure 57:
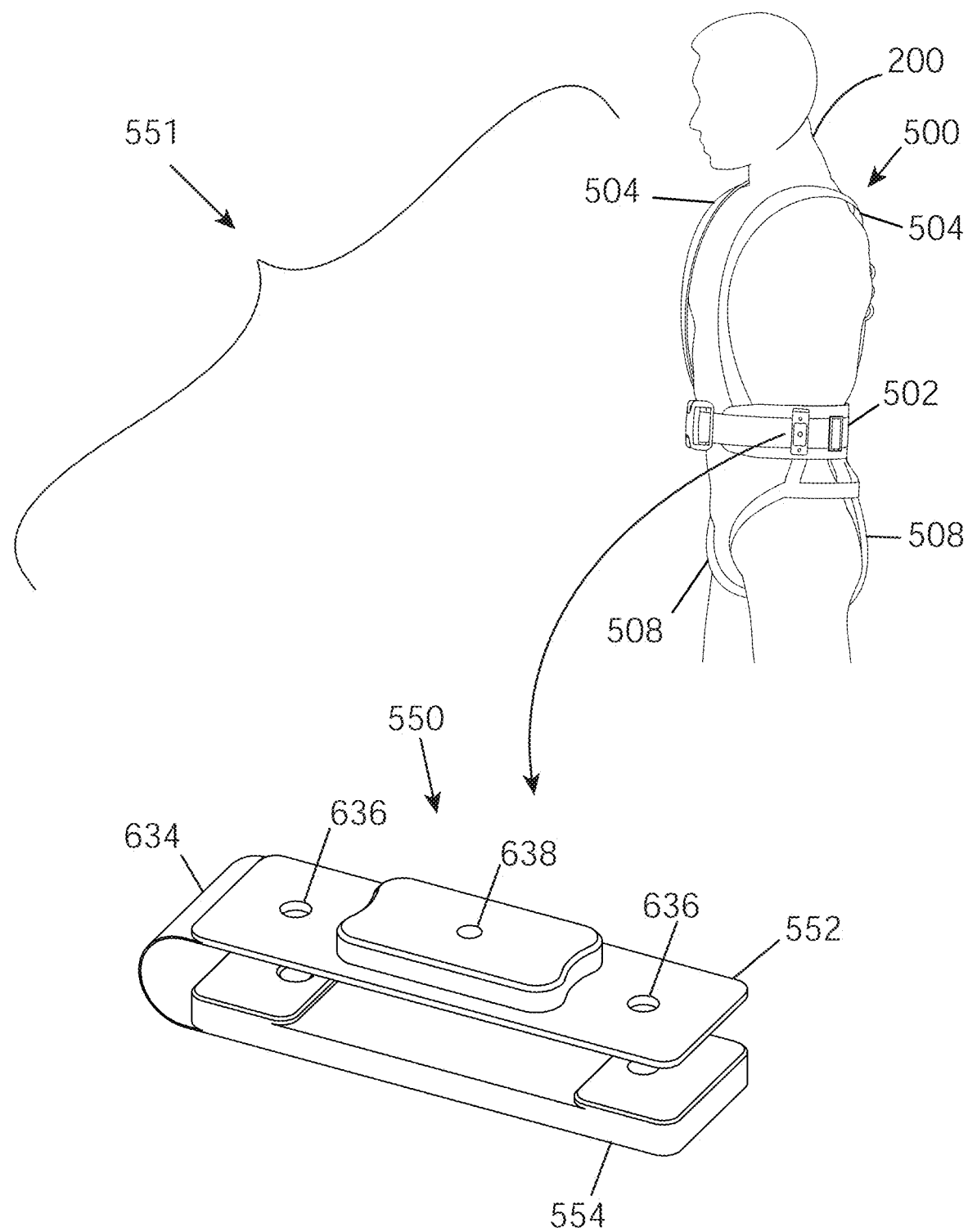
FIG. 57 depicts an embodiment of an outer plate and an inner plate being spring loaded together through a leaf spring.
Figure 58:
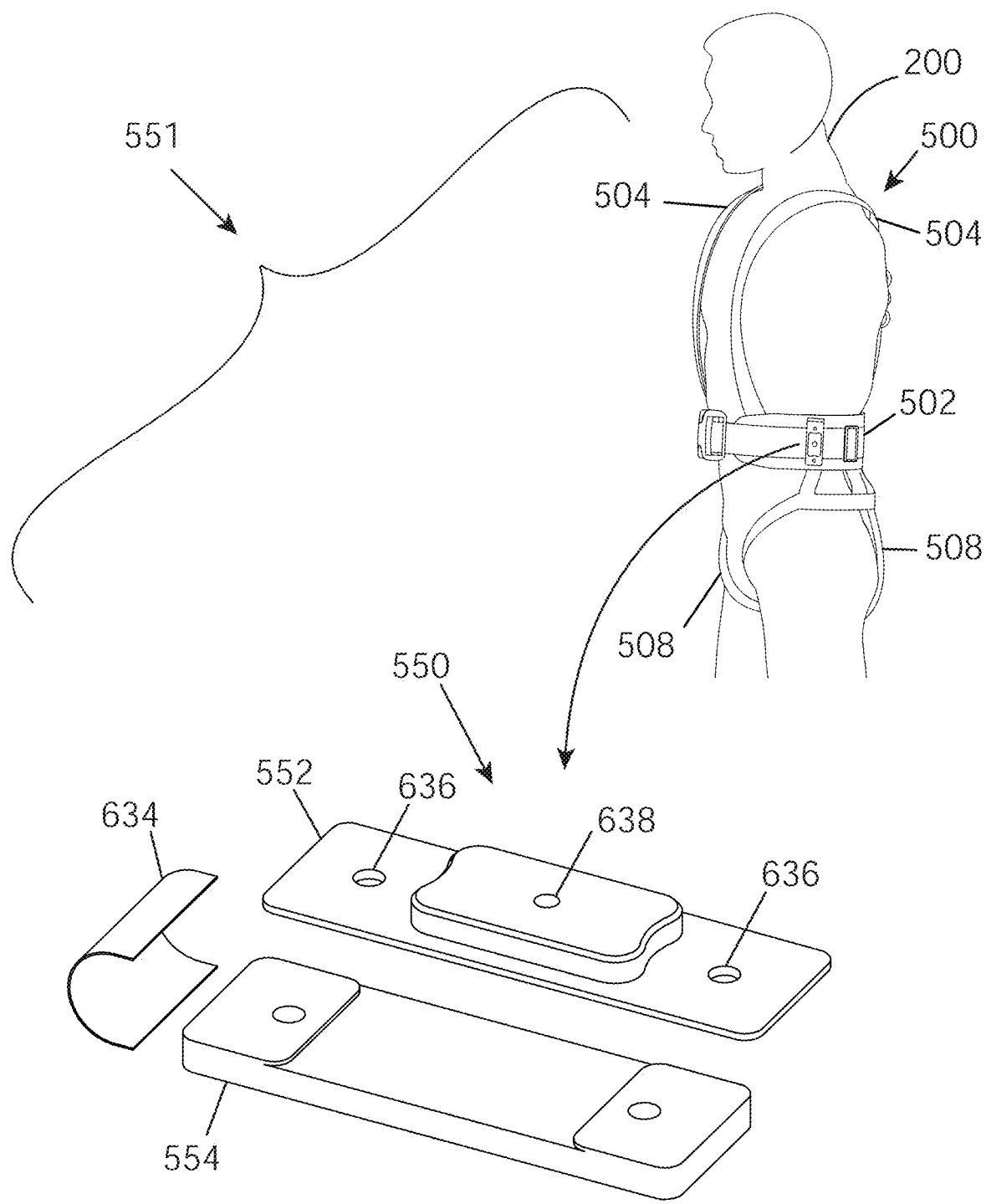
FIG. 58 depicts an exploded view of the embodiment of FIG. 57.

In some embodiments, as shown in FIG. 57, outer plate 552 and inner plate 554 are pushed toward each other through leaf spring 634. FIG. 58 is the exploded view of arrangement of FIG. 57 for more clarity. Holes 636 are provided for fasteners 632 if further clamping force is needed. Hole 638 is provided on outer plate 552 for connecting button assembly 614 to outer plate 552. Waist belt 502 can easily be clamped between outer plate 552 and inner plate 554. In some embodiments, as shown in FIG. 57, leaf spring 634 is used to keep inner plate 554 and outer plate 552 in an open position relative to each other. This allows the quick movement of clamping device 550 relative to human machine interface 500. In this case, holes 636 are provided for fasteners 632 to provide clamping force. In some embodiments, as shown in FIG. 42, inner plate 554 and outer plate 552 are capable of rotation relative to each other. In some embodiments, as shown in FIG. 42, inner plate 554 and outer plate 552 rotate relative to each other along axis 556. Arrow 562 shows the direction of motion inner plate 554 and outer plate 552 relative to each other.

In some embodiments, as shown in FIGS. 41, 42 and 43, clamping device 550 further comprises spring plunger 558 configured to lock and release outer plate 552 from its clamping position. When spring plunger 558 is pulled, outer plate 552 gets released. Although FIGS. 41, 42 and 43 show the coupling action to waist belt 502, one can clamp other components of human interface system 500. In some embodiments, clamping device 550 can be used to clamp shoulder strap 504. In some embodiments, clamping device 550 can be used to clamp thigh strap 508.

In some embodiments, (as shown in FIGS. 57 and 58) coupling device 551 may be used for coupling any type of exoskeleton to wearer 200. In general, this disclosure describes coupling device 551 that comprises human interface system 500 configured to be worn by the wearer, and a clamping device 550 for coupling and uncoupling exoskeleton 100 to and from human interface system 500 (FIG. 57 and FIG. 58). Clamping device 550 comprises an outer plate 552 and an inner plate 554. The outer plate 552 is configured to be coupled to exoskeleton. In operation, when inner plate 554 and outer plate 552 are pushed against each other, at least one component of human interface system 500 is clamped between inner plate 554 and outer plate 552.

Figure 59:
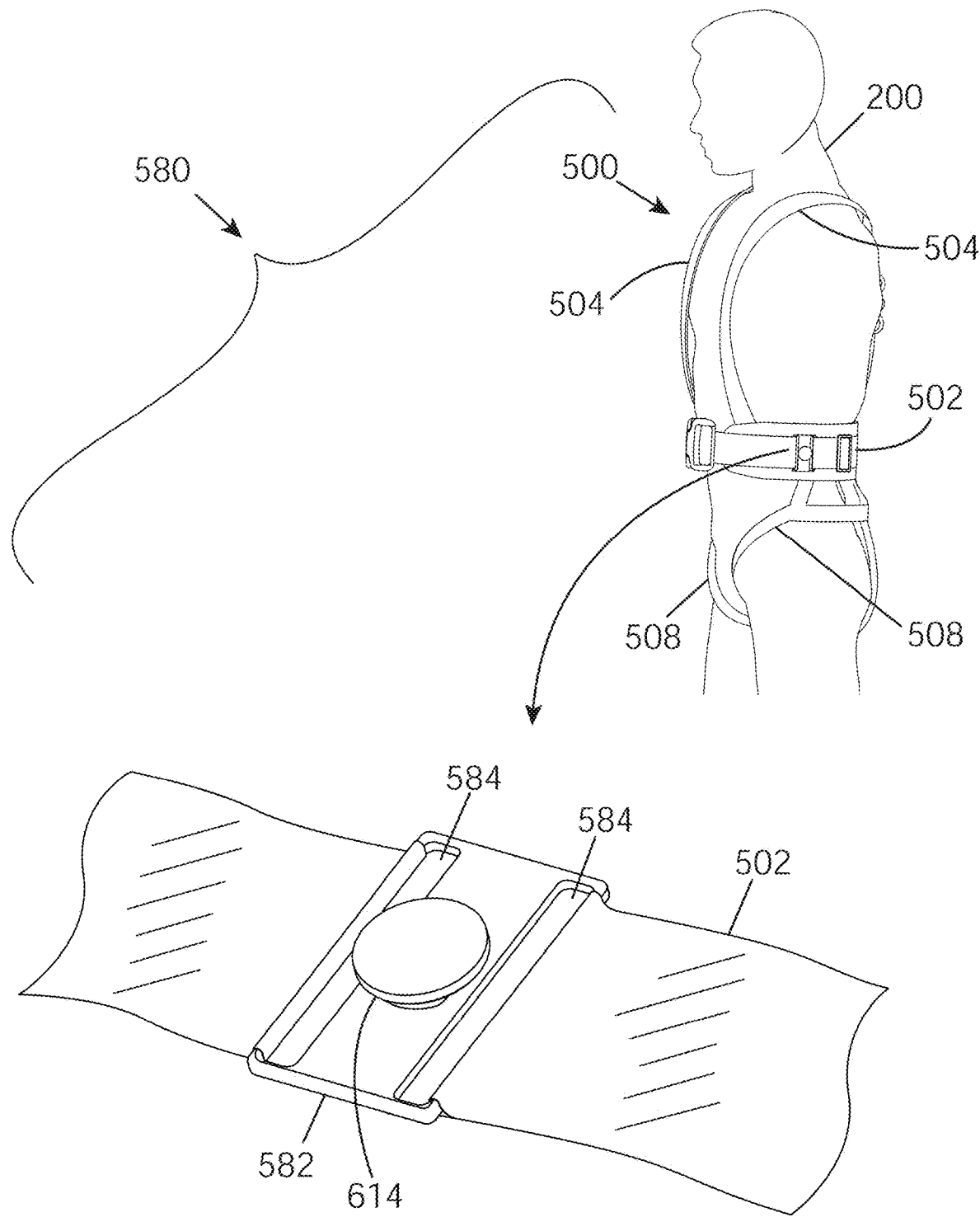
FIG. 59 depicts an embodiment of a block with two openings for coupling to a waist belt.
Figure 60:
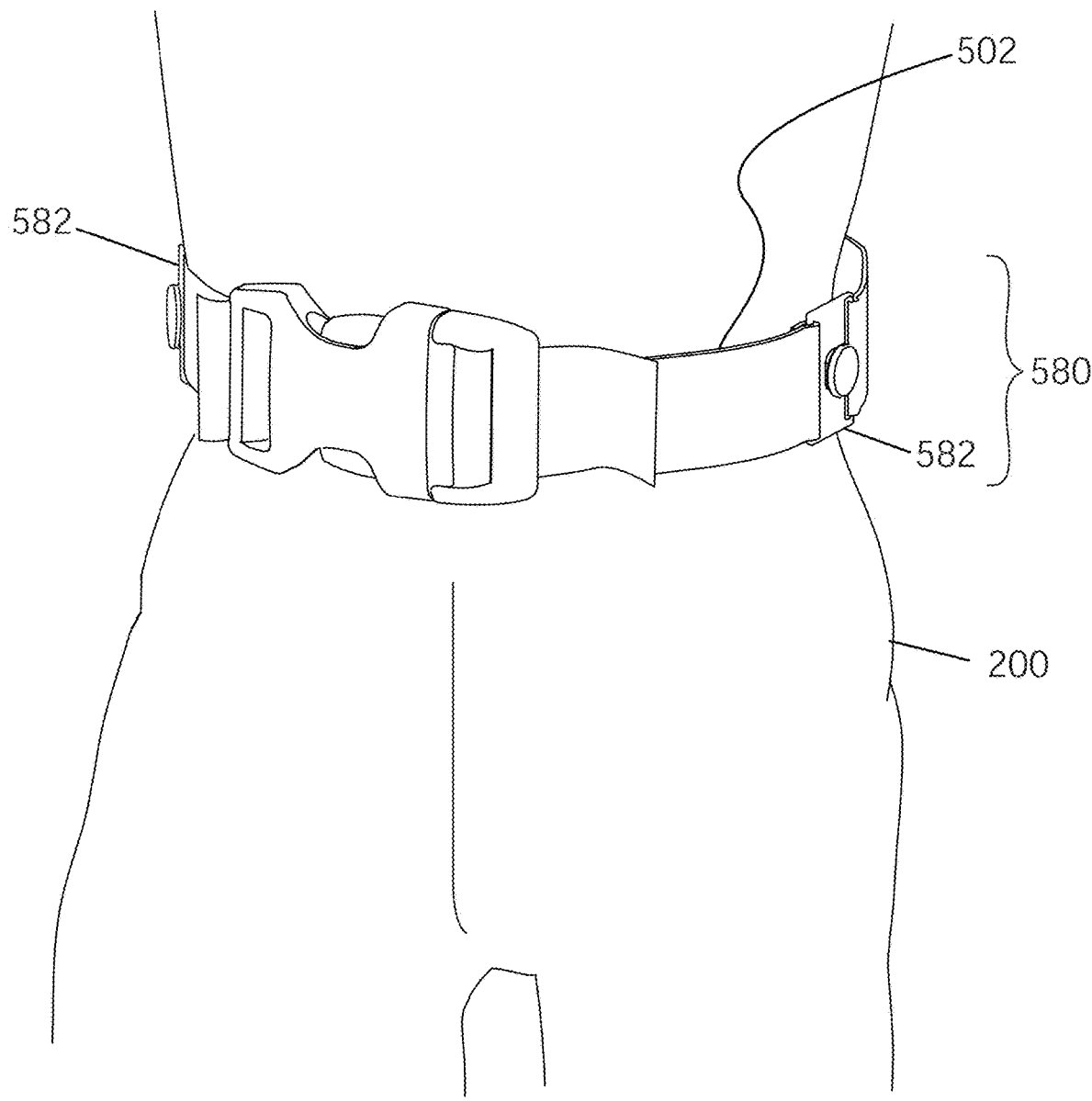
FIG. 60 depicts an embodiment of a two-button assembly mounted on two sides of a wearer.

FIGS. 59 and 60 shows another embodiment of the coupling device 580 for coupling trunk supporting exoskeleton 100 to wearer 200. Coupling device 580 comprises a human interface system 500 configured to be worn by the wearer. Coupling device 580 further comprises block 582. Block 582, as shown FIGS. 44, 45 and 59, has at least two openings 584. Block 582 is configured to be coupled to trunk support exoskeleton 100. Coupling features 588 (shown in FIG. 45) are used to couple block 582 to trunk supporting exoskeleton 100. At least one component of human interface 500 passes through two openings 584. As shown in FIGS. 45 and 60 when waist belt 502 (a component of human interface system 500) passes through two openings 584, waist belt 502 is secured to block 582.

FIG. 59 shows an embodiment of the coupling device 580 for coupling trunk supporting exoskeleton 100 to wearer 200. Coupling device 580 comprises human interface system 500 (waist belt 502 as shown in FIG. 59) configured to be worn by the wearer. As shown in FIG. 59, when waist belt 502 (a component of human interface system 500) is coupled to two openings 584, waist belt 502 is secured to block 582. As shown in FIG. 59, button assembly 614 is coupled to block 582 for coupling to a component of trunk supporting exoskeleton 100. Although above describes the coupling of button assembly 614 to waist belt 502, it is understood that one of ordinary skill in the art can develop various methods of coupling holding bracket 612 to block 582. It will further be understood that coupling device 580 shown in FIGS. 44, 45, 59 and 60 can be employed to couple any exoskeleton to human interface system 500.

Figure 61:
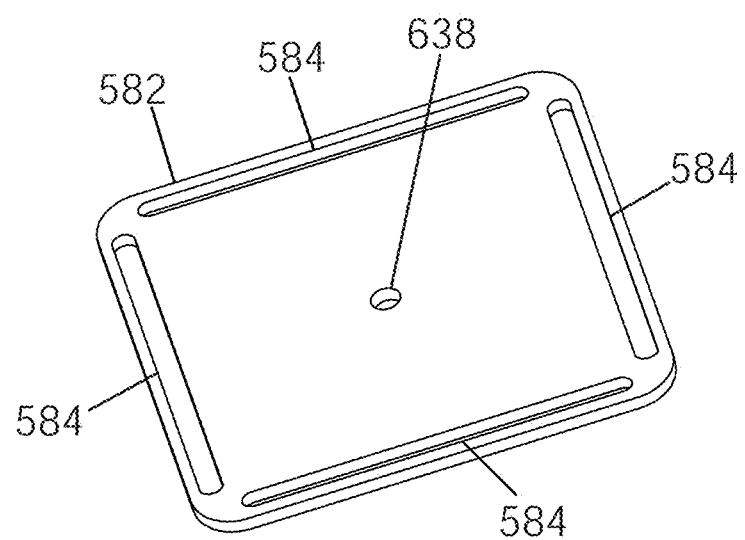
FIG. 61 depicts an embodiment of a block comprising at least four openings to allow for coupling of the block to two shoulder straps and two thigh straps.
Figure 62:
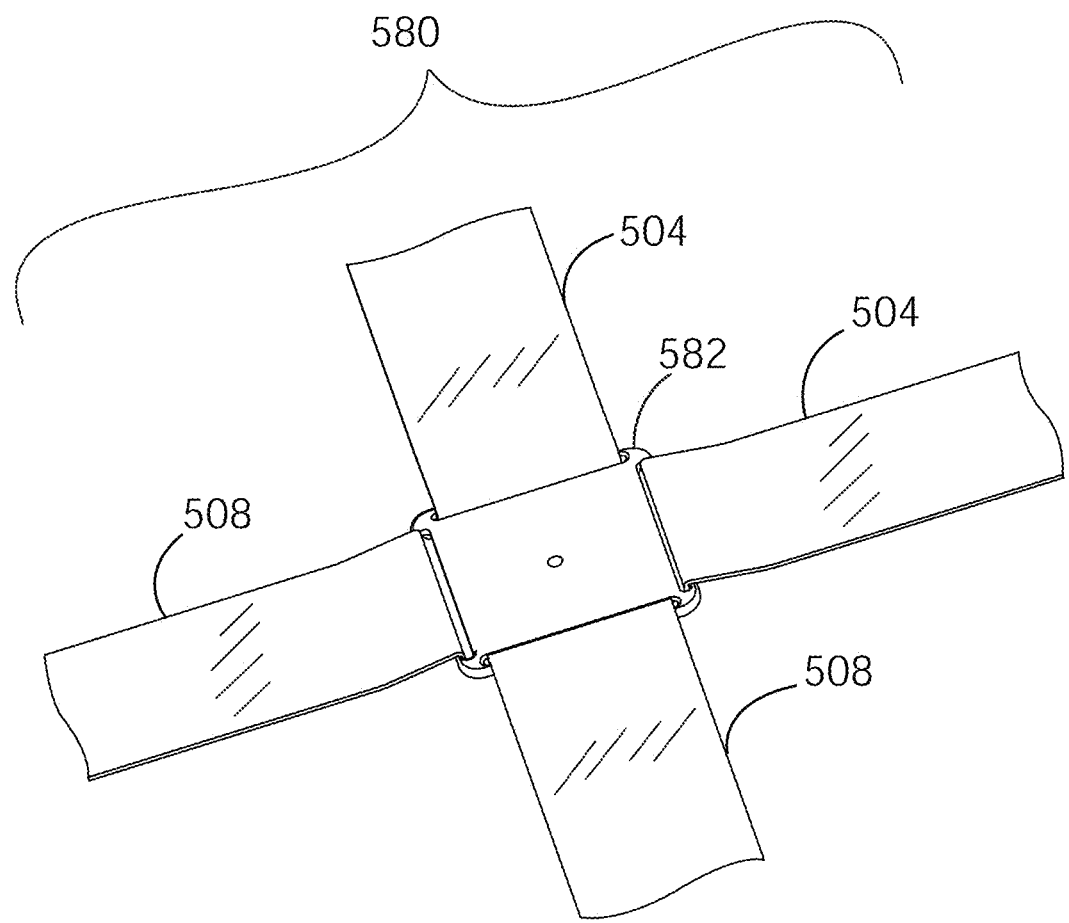
FIGS. 62 and 63 depict embodiments of shoulder straps passing through two openings opposite to each other to become thigh straps.
Figure 63:
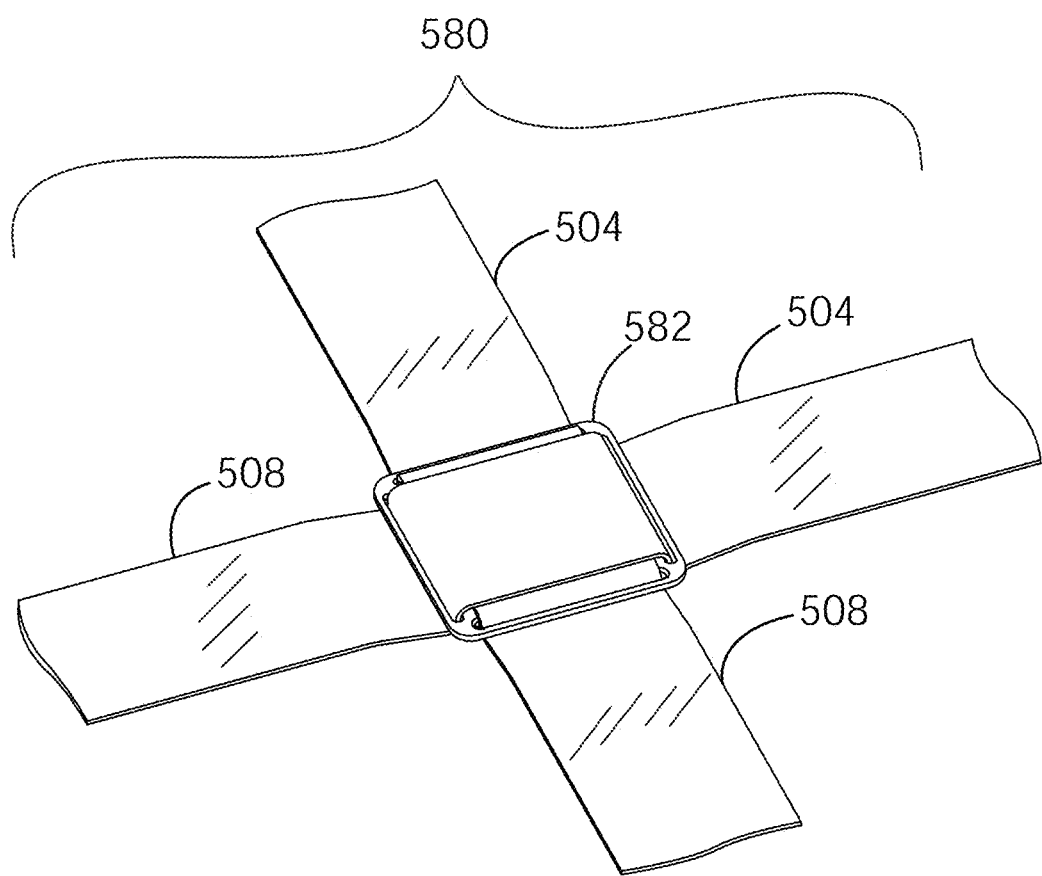
Figure 64:
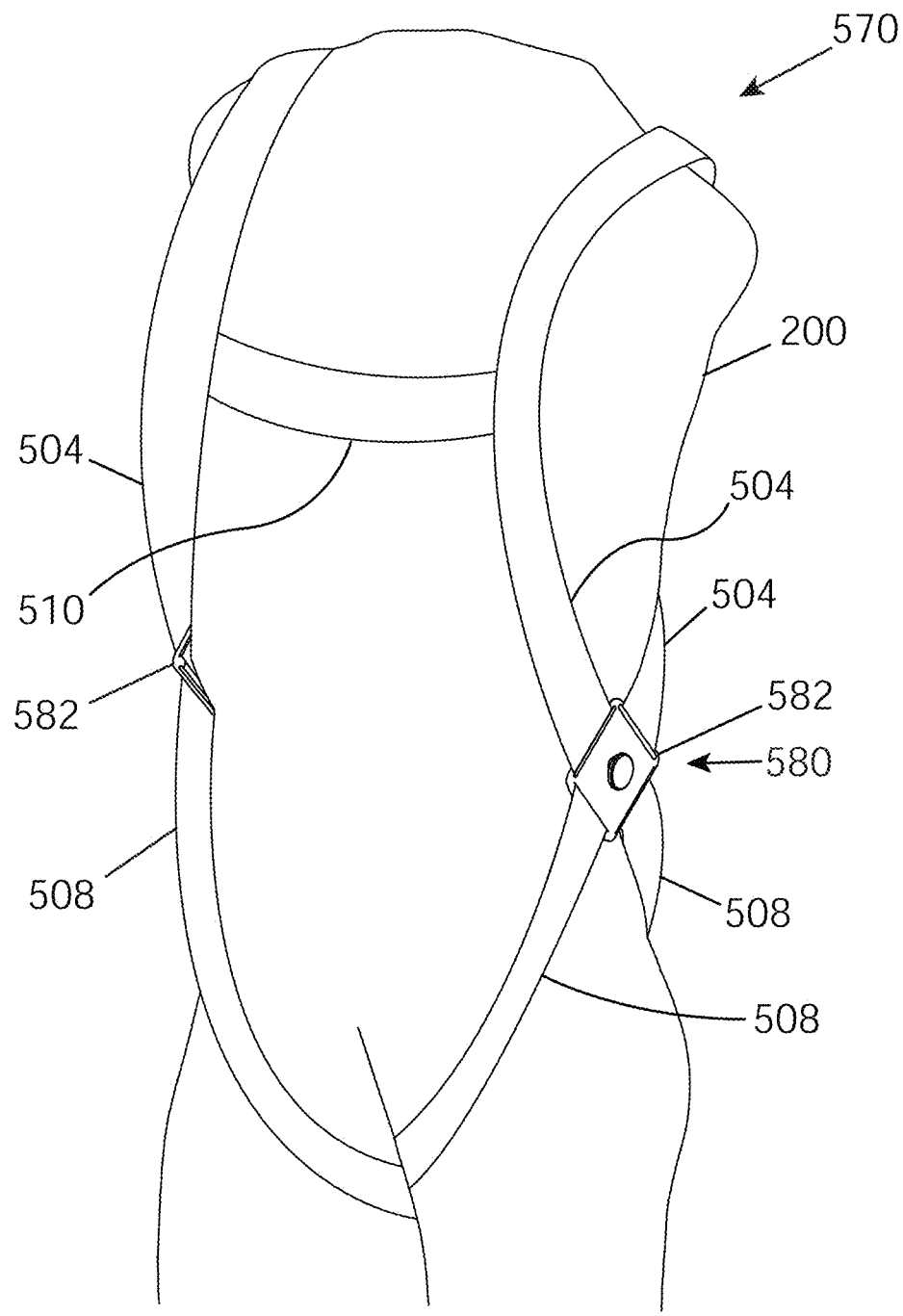
FIGS. 64 and 65 depict a front view and a rear view of the wearer where two button assemblies are coupled to a fall protection safety harness at two sides of the wearer.

FIG. 61 shows another embodiment of block 582 with four openings 584. These openings allow for coupling of block 582 to two shoulder straps 504 and two thigh straps 508 as shown in FIGS. 62 and 63. Shoulder strap 504 passes through two openings opposite to each other to become thigh strap 508 as shown in FIGS. 64 and 65. In operation when shoulder strap 504 passes through two opposite openings 584, block 582 is secured to shoulder strap 504. Additionally, when thigh strap 508 passes through two opposite openings 584, block 582 is secured to thigh strap 508. FIGS. 64 and 65 show an embodiment of coupling device 580 that comprises block 582 and fall protection safety harness 570 (a form of human interface system 500). FIGS. 64 and 65 show the front view and the rear view of wearer 200 where two button assemblies 614, are coupled to fall protection safety harness 570 on two sides of wearer 200 (Since all protection safety harness 570 is symmetrical, for brevity, only one side is shown). In general, one of ordinary skill in the art can couple either holding bracket 612 or button assembly 614 to human interface system 500 or a fall protection safety harness (shown in FIGS. 64 and 65) using the arrangement shown in FIGS. 61, 62 and 63.

In general FIGS. 44, 45 and FIGS. 59 to 65 teach coupling device 580 or coupling an exoskeleton to wearer 200. Coupling device 580 comprise human interface system 500 which is configured to be wont by the wearer 200. Coupling device 580 further comprises block 582 having at least two openings 584 and configured to be coupled to the exoskeleton. In operation when at least one component of human interface 500 passes through at least two openings or at least one component of human interface 500 is coupled to two openings, block 582 is secured to human interface system 500. As shown in FIGS. 45 and 60, when waist belt 502 passes through two openings, block 582 is secured to waist belt 502. FIG. 59 shows the situation where at least one component of human interface 500 (waist belt 502) is coupled to two openings 584. As shown in FIGS. 62-65, when shoulder strap 504 passes through two openings, block 582 is secured to shoulder strap 504. As shown in FIGS. 62-65, when thigh strap 508 passes through two openings, block 582 is secured to thigh strap 508.

What is claimed is:

1. A combination comprising:
a trunk supporting exoskeleton comprising:
a supporting trunk configured to be coupled to a trunk of a wearer;
first and second thigh links configured to move in unison with thighs of the wearer in a manner resulting in flexion and extension of the first and second thigh links relative to the supporting trunk; and
first and second torque generators configured to be located on both left and right halves of the wearer, coupling the supporting trunk to the first and second thigh links respectively and configured to generate torque between the first and second thigh links and the supporting trunk; and
a coupling device for coupling the trunk supporting exoskeleton to the wearer, the coupling device comprising:
a human interface system, configured to be worn by the wearer, and
a block, rotatably coupled to the trunk supporting exoskeleton, wherein when the block is secured to the human interface system the trunk supporting exoskeleton is able to freely rotate relative to the human interface system.

2. The combination of claim 1, wherein at least one component of the human interface system comprises a waist belt.

3. The combination of claim 1, wherein at least one component of the human interface system comprises a shoulder strap.

4. The combination of claim 1, wherein at least one component of the human interface system comprises a thigh strap.

5. The combination of claim 1,
wherein the trunk supporting exoskeleton is coupled to the block through a quick release mechanism, and
wherein the quick release mechanism comprises:
a button assembly coupled to one of the human interface system and at least a component of the trunk supporting exoskeleton,
a cavity formed in another one of the block and at least a component of the trunk supporting exoskeleton such that the button assembly can be moved into and removed out of the cavity when the button assembly and the cavity are oriented along a first orientation relative to each other.

6. The combination of claim 5, wherein:
for coupling the trunk supporting exoskeleton and the human interface system to each other, after the button assembly is moved into the cavity, at least one component of the trunk supporting exoskeleton is configurable to be aligned to a second orientation in which the button assembly cannot be removed from the cavity, and
for uncoupling the trunk supporting exoskeleton and the human interface system from each other, the at least one component of the trunk supporting exoskeleton is configurable to be aligned to the first orientation in which the button assembly can be removed from the cavity.

7. The combination of claim 1, wherein the human interface system is selected from the group consisting of a safety harness, a fall protection safety harness, a fall prevention harness, a waist belt, a safety belt, a fall protection safety belt, a tool belt harness, a tool belt, a climbing harness, and combinations thereof.

8. The combination of claim 1, wherein each of the first and second torque generators is configured such that:
when the wearer bends forward in a sagittal plane such that a predetermined portion of the supporting trunk passes beyond a predetermined angle from a vertical, at least one of the first and second torque generators imposes a resisting torque between the supporting trunk and at least one of the first and second thigh links, causing the supporting trunk to impose a force against the trunk of the wearer and at least one of the first and second thigh links to impose a force onto at least one of the thighs of the wearer, and when the predetermined portion of the supporting trunk does not pass beyond the predetermined angle from the vertical, the first and second torque generators through and an entire range of motion of the first and second thigh links, impose no resisting torques between the supporting trunk and the respective first and second thigh links.

9. The combination of claim 8, wherein each of the first and second torque generators further comprises an angle adjustment mechanism configured to adjust the predetermined angle.

10. The combination of claim 8, wherein each of the first and second torque generators is configured to automatically transition, independently of one another, between
   a neutral position where no torque is generated and
   an engaged position where the resisting torque is generated between the respective first and second thigh links and the supporting trunk.

11. The combination of claim 8, wherein each of the first and second torque generators further comprises a compression spring configured to provide the resisting torque.

12. The combination of claim 11, wherein the compression spring is a gas spring.

13. The combination of claim 11, wherein each of the first and second torque generators further comprises an override mechanism configured to deactivate the compression spring so that the compression spring does not act between the supporting trunk and the first and second thigh links.

14. The combination of claim 1,
   wherein the supporting trunk further comprises a chest plate and two opposing side brackets, and
   wherein a horizontal distance between the two opposing side brackets is adjustable to adjust a width of the supporting trunk.

15. The combination of claim 1,
   wherein the supporting trunk further comprises a chest plate and two opposing side brackets, and
   wherein a location of each of the two side brackets is adjustable with respect to the first and second torque generators to adjust a position of the chest plate on the wearer.

16. The combination of claim 1 further comprising a chest plate and a chest pad, wherein the chest pad is capable of moving or rotating relative to the chest plate.

17. The combination of claim 1, wherein supporting trunk further comprises:
   a lower frame coupled to the first and second torque generators located substantially behind the wearer, and
   an upper frame configured to be in contact with the trunk of the wearer to impose a supporting force, wherein the upper frame can pivot about multiple axes relative to the lower frame.

18. The combination of claim 1, wherein each of the first and second torque generators further comprises:
   an upper bracket coupled to the supporting trunk, and
   a lower bracket coupled to the first and second thigh links and rotatably coupled to the upper bracket at an exoskeleton joint.

19. The combination of claim 1, wherein the block is configured to couple to one of the first and second torque generators.

* * * * *